United States Patent [19]
de Laszlo et al.

[11] Patent Number: 5,837,719
[45] Date of Patent: Nov. 17, 1998

[54] 2,5-SUBSTITUTED ARYL PYRROLES, COMPOSITIONS CONTAINING SUCH COMPOUNDS AND METHODS OF USE

[75] Inventors: Stephen E. de Laszlo, Rumson, N.J.; Nigel J. Liverton, Harleysville, Pa.; Gerald S. Ponticello, Lansdale, Pa.; Harold G. Selnick, Ambler, Pa.; Nathan B. Mantlo, Lafayette, Colo.

[73] Assignee: Merck & Co., Inc., Rahway, N.J.

[21] Appl. No.: 694,143

[22] Filed: Aug. 8, 1996

Related U.S. Application Data

[60] Provisional application No. 60/002,094 Aug. 10, 1995 and provisional application No. 60/014,182 Mar. 26, 1996.

[51] Int. Cl.$^6$ ............................ A01N 43/40; C07D 401/00
[52] U.S. Cl. .................. 514/343; 546/276.4; 546/278.4
[58] Field of Search ............................ 546/276.4, 278.4; 514/343

[56] References Cited

U.S. PATENT DOCUMENTS

| | | | |
|---|---|---|---|
| 4,267,184 | 5/1981 | Cherkofsky | 424/263 |
| 5,286,742 | 2/1994 | Henegar et al. | 514/423 |
| 5,442,060 | 8/1995 | Jikihara et al. | 544/106 |
| 5,502,051 | 3/1996 | Scharfenberg et al. | 514/235.5 |

FOREIGN PATENT DOCUMENTS

| | | |
|---|---|---|
| 0 025 884 | 4/1981 | European Pat. Off. . |
| 0 287 890 A1 | 10/1988 | European Pat. Off. . |
| 0 300 688 A1 | 1/1989 | European Pat. Off. . |
| 300688 | 1/1989 | European Pat. Off. . |
| 0 320 628 A1 | 6/1989 | European Pat. Off. . |
| 298 913 A5 U | 10/1983 | Germany . |
| 298 915 A5 U | 10/1983 | Germany . |
| 1099500 | 1/1968 | United Kingdom . |
| 1099500 | 11/1969 | United Kingdom . |
| WO 91/02731 | 3/1991 | WIPO . |
| WO 94/15932 | 7/1994 | WIPO . |
| WO 95/00501 | 1/1995 | WIPO . |
| WO96/17841 | 6/1996 | WIPO . |

OTHER PUBLICATIONS

Heterocycles, vol. 35, No. 2, pp. 1171–1184 (1993), by Konakahara, et al.
Journal of Heterocyclic Chemistry, vol. 26, No. 2, pp. 489–492 (1989), by Silverstri, et al.
Journal of Heterocyclic Chemistry, vol. 29, No. 7, pp. 1847–1850 (1992) by Silvestri, et al.
Journal of the Chemical Society, J.C.S. Perkin 1, vol. 10, pp. 2642–2646 (1981), by Petruso, et al.
Konakahara et. al., "One–Pot Synthesis of Pyrroles . . . ", Heterocycles, vol. 35, No. 2, May 1993, pp. 1171–1184.
Chem. Ber., vol. 122, pp. 295–300 (1989), by F. Clerici, et al.
J. of Heter. Chem., vol. 28, pp. 793–796 (1991), by S. Petruso, et al.

*Primary Examiner*—Mukund J. Shah
*Assistant Examiner*—Tamthom T. Ngo
*Attorney, Agent, or Firm*—Elliott Korsen; Mark R. Daniel

[57] ABSTRACT

The present invention addresses 2, 5-substituted aryl pyrroles of the formula:

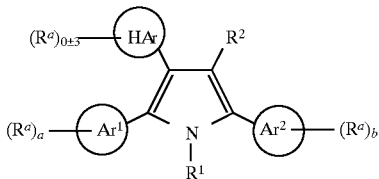

or a pharmaceutically acceptable salts thereof, as well as compositions containing such compounds and methods of treatment. The compounds are useful for treating Cytokine mediated diseases, which refers to diseases or conditions in which excessive or unregulated production or activity of one or more cytokines occurs. Interleukin-1 (IL-1), Interleukin-6 (IL-6), Interleukin-8 (IL-8) and Tumor Necrosis Factor (TNF) are cytokines which are involved in immunoregulation and other physiological conditions, such as inflammation. The compounds also have glucagon antagonist activity.

25 Claims, No Drawings

2,5-SUBSTITUTED ARYL PYRROLES, COMPOSITIONS CONTAINING SUCH COMPOUNDS AND METHODS OF USE

CROSS REFERENCE TO RELATED APPLICATIONS

This application is based upon provisional U.S. application Ser. No. 60/002,094 filed on Aug. 10, 1995 and upon provisional U.S. application Ser. No. 60/014,182 filed on Mar. 23, 1996, priority of which is claimed hereunder.

BACKGROUND OF THE INVENTION

The present invention addresses 2,5-substituted aryl pyrroles, as well as compositions containing such compounds and methods of treatment.

Cytokine mediated diseases refers to diseases or conditions in which excessive or unregulated production of one or more cytokines occurs. Interleukin-1 (IL-1) and Tumor Necrosis Factor (TNF) are cytokines produced by a variety of cells, which are involved in immunoregulation and other physiological conditions, such as inflammation.

IL-1 has been demonstrated to mediate a variety of biological activities thought to be important in immunoregulation and other physiological conditions. [See, e.g., Dinarello et al., Rev. Infect. Disease, 6, 51 (1984)]. The myriad of known biological activities of IL-1 include the activation of T-helper cells, induction of fever, stimulation of prostaglandin or collagenase production, neutrophil chemotaxis, induction of acute phase proteins and the suppression of plasma iron levels.

There are many disease states in which IL-1 is implicated. Included among these diseases are rheumatoid arthritis, osteoarthritis, endotoxemia, toxic shock syndrome, other acute or chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis. Recent evidence also links IL-1 activity to diabetes and pancreatic β cells.

Excessive or unregulated TNF production has been implicated in mediating or exacerbating rheumatoid arthritis, rheumatoid spondylitis, osteoarthritis, gouty arthritis, and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS related complex (ARC), keloid formation, scar tissue formation, Crohn's disease, ulcerative colitis and pyresis.

Monokines, such as TNF, have been shown to activate HIV replication in monocytes and/or macrophages [See Poli, et al., Proc. Natl. Acad. Sci., 87:782–784 (1990)]. Therefore, inhibition of monokine production or activity aids in limiting HIV progression as stated above for T-cells. TNF has also been implicated in various roles with other viral infections, such as the cytomegalovirus (CMV), influenza virus and the herpes virus.

IL-6 is a cytokine effecting the immune system, hematopoiesis and acute phase reactions. It is produced by several mammalian cell types in response to agents such as IL-1 and is correlated with disease states such as angiofollicular lymphoid hyperplasia.

Interleukin-8 (IL-8) is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like L-1, IL-8 is produced by several cell types, including mononuclear cells, fibroblasts, and endothelial cells. Its production is induced by IL-1, TNF and by lipopolysaccharide (LPS). IL-8 stimulates a number of cellular functions in vitro. It is a chemoattractant for neutrophils, T-lymphocytes and basophils. It induces histamine release from basophils. It causes lysozomal enzyme release and respiratory burst from neutrophils, and it has been shown to increase the surface expression of Mac-1 (CD 11b/CD 18) on neutrophils without de novo protein synthesis. There remains a need for treatment, in this field, for compounds which are cytokine suppressive or antagonistic, i.e., compounds which are capable of inhibiting or antagonizing cytokines such as IL-1, IL-6, IL-8 and TNF.

The compounds of formula I are also useful in treating diseases characterized by excessive IL-8 activity. There are many disease states in which excessive or unregulated IL-8 production is implicated in exacerbating and/or causing the disease. These diseases include psoriasis, inflammatory bowel disease, asthma, cardiac and renal reperfusion injury, adult respiratory distress syndrome, thrombosis and glomerulonephritis.

SUMMARY OF THE INVENTION

The present invention is directed to a compound represented by formula I:

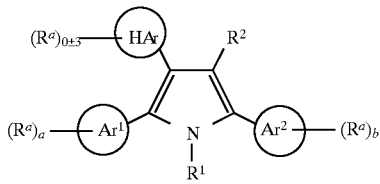

or a pharmaceutically acceptable salt thereof, wherein:

and

each independently represent a 5–10 membered aryl or heteroaryl group substituted with $R^a$ groups;

wherein a and b represents integers, 0, 1, 2 or 3, such that the sum of a plus b is 1, 2, 3 or 4;

represents a heteroaryl group containing from 5 to 10 atoms, 1–4 of which are heteroatoms, 0–4 of which heteroatoms are N and 0–1 of which are O or S, said heteroaryl group being unsubstituted or substituted with 0–3 $R^a$ groups; each $R^a$ independently represents a member selected from the group consisting of: halo; CN, $NO_2$, $R^{21}$; $OR^{23}$; $SR^{23}$; $S(O)R^{21}$; $SO_2R^{21}$; $NR^{20}R^{23}$; $NR^{20}COR^{21}$; $NR^{20}CO_2R^{21}$; $NR^{20}CONR^{20}R^{23}$; $NR^{20}SO_2R^{21}$; $NR^{20}C(NR^{20})NHR^{20}$, $CO_2R^{23}$; $CONR^{20}R^{23}$; $SO_2NR^{20}R^{23}$; $SO_2NR^{20}COR^{21}$; $SO_2NR^{20}CONR^{20}R^{23}$; $SO_2NR^{20}CO_2R^{21}$; $OCONR^{20}R^{23}$; $OCONR^{20}SO_2R^{20}$, $C(O)OCH_2OC(O)R^{20}$; $C(NR^{20})NR^{20}R^{23}$ and $CONR^{20}SO_2R^{21}$;

$R^1$ is selected from the group consisting of: H, aryl, $C_{1-15}$ alkyl, $C_{3-15}$ alkenyl, $C_{3-15}$ alkynyl and heterocyclyl, said alkyl, aryl, alkenyl, alkynyl and heterocyclyl being optionally substituted with from one to three members selected from the group consisting of: aryl, heteroaryl, heterocyclyl, $OR^{20}$, $SR^{20}$, $N(R^{20})_2$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$; $OCONR^{20}R^{23}$ and $C(O)OCH_2OC(O)R^{20}$;

$R^2$ is selected from the group consisting of: H, $C_{1-15}$ alkyl, $C_{2-15}$ alkenyl, $C_{2-15}$ alkynyl, halo, $NO_2$, heterocyclyl, CN, $S(O)R^{21}$, $SO_2R^{21}$, $SO_2N(R^{20})_2$, $SO_2NR^{20}COR^{21}$, $SO_2NR^{20}CON(R^{20})_2$, $COR^{20}$, $CO_2R^{20}$, $CONR^{20}R^{23}$, $CONR^{20}SO_2R^{21}$ and $SO_2NR^{20}CO_2R^{21}$, said alkyl, alkenyl, alkynyl and heterocyclyl being optionally substituted with from one to three members selected from the group consisting of: halo, heterocyclyl, CN, aryl, heteroaryl, $R^{20}$, $OR^{20}$, $SR^{20}$, $NR^{20}R^{23}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $NR^{20}C(NR^{20})NHR^{20}$, $CO_2R^{20}$, $CONR^{20}R^{23}$, $CONR^{20}SO_2R^{22}$, $NR^{20}SO_2R^{21}$, $SO_2NR^{20}CO_2R^{22}$, $OCONR^{20}SO_2R^{21}$ and $OCONR^{20}R^{23}$;

$R^{20}$ represents a member selected from the group consisting of: H, $C_{1-15}$ alkyl, $C_{2-15}$ alkenyl, $C_{2-15}$ alkynyl, heterocyclyl, aryl and heteroaryl, said alkyl, alkenyl, alkynyl, heterocyclyl, aryl and heteroaryl being optionally substituted with 1–3 groups selected from halo, aryl and heteroaryl;

$R^{21}$ represents a member selected from the group consisting of: $C_{1-15}$ alkyl, $C_{2-15}$ alkenyl, $C_{2-15}$ alkynyl, heterocyclyl, aryl and heteroaryl, such alkyl, alkenyl and alkynyl being optionally interrupted with oxo and/ or 1–2 heteroatoms selected from O, S, S(O), $SO_2$ and $NR^{20}$, said alkyl, alkenyl, alkynyl, aryl and heteroaryl being optionally substituted with from 1–3 of halo, heterocyclyl, aryl, heteroaryl, CN, $OR^{20}$, $O((CH_2)_nO)_mR^{20}$, $NR^{20}((CH_2)_nO)_mR^{20}$ wherein n represents an integer of from 2 to 4, and m represents an integer of from 1 to 3; $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}OC(O)R^{20}$, $C(O)OCH_2OC(O)R^{20}$ and $OCON(R^{20})_2$;

$R^{22}$ is selected from the group consisting of: $C_{1-15}$ alkyl, $C_{2-15}$ alkenyl, $C_{2-15}$ alkynyl, heterocyclyl, aryl and heteroaryl, said alkyl, alkenyl, and alkynyl being optionally substituted with 1–3 halo, aryl or heteroaryl groups;

$R^{23}$ is $R^{21}$ or H;

$R^{24}$ is selected from $COR^{22}$, $CO_2R^{22}$, $CON(R^{20})_2$, $SO_2R^{22}$ and $R^{23}$;

and when two $R^{20}$ groups are present, when $R^{20}$ and $R^{21}$ are present, or when $R^{20}$ and $R^{23}$ are present, said two $R^{20}$ groups, $R^{20}$ and $R^{21}$ or said $R^{20}$ and $R^{23}$ may be taken in combination with the atoms to which they are attached and any intervening atoms and represent heterocyclyl containing from 5–10 atoms, at least one atom of which is a heteroatom selected from O, S or N, said hetercyclyl optionally containing 1–3 additional N atoms and 0–1 additional O or S atom.

Also included in the invention is a pharmaceutical composition which is comprised of a compound of formula I in combination with a pharmaceutically acceptable carrier.

The invention includes a method of treating psoriasis, inflammatory bowel disease, asthma, cardiac and renal reperfusion injury, adult respiratory distress syndrome, thrombosis and glomerulonephritis, in a mammal in need of such treatment which comprises administering to said mammal a compound of formula I in an amount which is effective for treating said disease or condition.

Also included in the invention is a method of treating a cytokine mediated disease in a mammal, comprising administering to a mammalian patient in need of such treatment an amount of a compound of formula I which is effective to treat said cytokine mediated disease.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

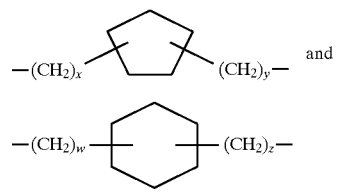

wherein:

x plus y=from 0–10 and w plus z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl and naphthyl substituted with one or two groups.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three $R^a$ groups.

Heteroaryl thus includes aromatic and partially aromatic groups which contain one or more heteroatoms. Examples of this type are thiophene, purine, imidazopyridine, pyridine, oxazole, thiazole, pyrazole, tetrazole, imidazole, pyrimidine, pyrazine and triazine.

The groups

and represent

represent 5–10 membered aryl or heteroaryl, each of which is substituted with 0–3 groups selected from $R^a$ such that a total of 1 to 4 groups is attached to

and

Preferred are phenyl, naphthyl, pyridyl, pyrimidinyl, thiophenyl, furanyl, imidazolyl, thiazolyl, isothiazolyl, oxazolyl, and isoxazolyl.

The group

represents a heteroaryl group which contains from 5 to 10 atoms. One to four atoms are heteroatoms which are selected from O, S and N. The heteroaryl group may be unsubstituted or substituted with 0–3 $R^a$ groups.

Preferred heteroaryl groups represented by

are as follows: pyridyl, quinolyl, purinyl, imidazolyl, imidazopyridine, and pyrimidinyl.

The terms "heterocycloalkyl" and "heterocyclyl" refer to a cycloalkyl group (nonaromatic) in which one of the carbon atoms in the ring is replaced by a heteroatom selected from O, S, SO, $SO_2$ or N, and in which up to three additional carbon atoms may be optionally replaced by heteroatoms.

Heterocyclyl is carbon or nitrogen linked; if carbon linked and contains a nitrogen, then the nitrogen may be substituted by $R^{24}$. Examples of heterocyclyls are piperidinyl, morpholinyl, pyrrolidinyl, tetrahydrofuranyl, tetrahydroimidazo[4,5-c]pyridinyl, imidazolinyl, piperazinyl, pyrolidin-2-onyl, piperidin-2-onyl and the like.

The term "TNF mediated disease or disease state" refers to any and all disease states in which TNF plays a role, either by production of TNF itself, or by TNF causing another monokine to be released, such as but not limited to IL-1 or IL-6. A disease state in which IL-1, for instance, is a major component, and whose production or action, is exacerbated or secreted in response to TNF, would therefore be considered a disease state mediated by TNF.

The term "cytokine" as used herein means any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor-beta (TNF-β).

By the term "cytokine interfering or cytokine suppressive amount" is mean an effective amount of a compound of formula I which will, cause a decrease in the in vivo levels of the cytokine or its activity to normal or sub-normal levels, when given to the patient for the prophylaxis or therapeutic treatment of a disease state which is exacerbated by, or caused by, excessive or unregulated cytokine production or activity.

The compounds of the present invention may contain one or more asymmetric carbon atoms and may exist in racemic and optically active forms. All of these compounds are contemplated to be within the scope of the present invention.

Throughout the instant application, the following abbreviations are used with the following meanings:

Bu butyl
Bn benzyl
BOC, Boc t-butyloxycarbonyl
calc. calculated
CBZ, Cbz Benzyloxycarbonyl
CDI N,N'-carbonyl diimidazole
FAB-MS Fast atom bombardment-mass spectroscopy
HPLC High pressure liquid chromatography
KHMDS Potassium bis(trimethylsilyl)amide
LAH Lithium aluminum hydride
LHMDS Lithium bis(trimethylsilyl)amide
Me methyl
MeOH methanol
MPLC Medium pressure liquid chromatography
NMR Nuclear Magnetic Resonance
Ph phenyl
Pr propyl
prep. prepared
Pyr. pyridyl
TMS Tetramethylsilane One subset of compounds of the invention includes compounds of formula I wherein $Ar^1$ and $Ar^2$ are independently selected from:

a) phenyl,
b) pyridyl,
c) pyrimidinyl,
d) thiophenyl,
e) furanyl,
f) imidazolyl,
g) thiazolyl,
h) isothiazolyl, i) oxazolyl,
j) isoxazolyl, and
k) napthyl.

Within this subset of compounds, all other variables are as previously defined with respect to formula I.

Another subset of compounds of the invention includes compounds of formula I wherein HAr is selected from:
a) pyridyl,
b) quinolyl,
c) purinyl,
d) imidazolyl,
e) imidazopyridine, and
f) pyrimidinyl.

Within this subset of compounds, all other variables are as originally defined with respect to formula I.

Another subset of compounds of formula I includes compounds wherein $R^1$ is hydrogen. Within this subset of compounds, all other variables are as originally defined with respect to formula I.

Another subset of compounds of formula I includes compounds wherein $R^1$ represents $C_{1-15}$ alkyl, unsubstituted or substituted, as originally defined. Within this subset of compounds, all other variables are as originally defined with respect to formula I.

Another subset of compounds of formula I includes compounds wherein $R^2$ represents a member selected from the group consisting of:
a) H;
b) alkyl;
c) halo;
d) CN;
e) $C(O)C_{1-6}$ alkyl;
f) $C(O)C_{1-6}$ alkylphenyl;
g) $CO_2H$;
h) $CO_2C_{1-6}$ alkyl
i) $CO_2C_{1-6}$ alkylphenyl;
j) $CONH_2$;
k) $CONHC_{1-6}$ alkyl;
l) $C(O)N(C_{1-6}$ alkyl$)_2$;
m) $SO_2NH_2$;
n) $SO_2NHC_{1-6}$ alkyl and
o) $SO_2N(C_{1-6}$ alkyl$)_2$.

Within this subset of compounds, all other variables are as originally defined with respect to formula I.

Preferred compounds of formula I are realized when: $Ar^1$ and $Ar^2$ are independently selected from:
a) phenyl,
b) pyridyl,
c) pyrimidinyl,
d) thiophenyl,
e) furanyl,
f) imidazolyl,
g) thiazolyl,
h) isothiazolyl,
i) oxazolyl,
j) isoxazolyl and
k) napthyl;

one, two or three $R^a$ groups are present and attached to $Ar^1$ and $Ar^2$, and each $R^a$ is independently selected from the group consisting of: halo, $R^{21}$, $OR^{23}$, $NR^{20}R^{23}$, $CO_2R^{23}$, $CONR^{20}R^{23}$, $SO_2R^{21}$ and $S(O)R^{21}$, $R^{20}$, $R^{21}$ and $R^{23}$ are as originally defined;

HAr is selected from:
a) pyridyl,
b) quinolyl,
c) purinyl,
d) imidazolyl,
e) imidazopyridinyl and
f) pyrimidinyl;

$R^1$ is:
a) H or
b) substituted or unsubstituted alkyl; and $R^2$ is selected from the group consisting of:
a) H,
b) alkyl,
c) halo,
d) CN,
e) $C(O)C_{1-6}$ alkyl,
f) $C(O)C_{1-6}$ alkylphenyl,
g) $CO_2H$,
h) $CO_2C_{1-6}$ alkyl,
i) $CO_2C_{1-6}$ alkylphenyl,
j) $CONH_2$,
k) $CONHC_{1-6}$ alkyl,
l) $C(O)N(C_{1-6}$ alkyl$)_2$,
m) $SO_2NH_2$,
n) $SO_2NHC_{1-6}$ alkyl and
o) $SO_2N(C_{1-6}$ alkyl$)_2$.

A more preferred subset of compounds of formula I is realized when: $(R^a)_a$—$Ar^1$ is selected from the group consisting of:
a) phenyl,
b) 4-fluorophenyl,
c) 4-chlorophenyl,
d) 3-fluorophenyl,
e) 3-chlorophenyl,
f) thiophen-2-yl,
g) thiophen-3-yl,
h) 4-fluorothiophen-2-yl,
i) 4-fluorothiophen-3-yl,
j) 5-fluorothiophen-2-yl,
k) 5-fluorothiophen-3-yl,
l) 4-chlorothiophen-2-yl,
m) 4-chlorothiophen-3-yl,
n) 5-chlorothiophen-2-yl,
o) 5-chlorothiophen-3-yl,
p) 3-methylphenyl,
q) 3,4-dichlorophenyl,
r) 3-hydroxyphenyl,
s) 4-hydroxyphenyl,
t) 3,4-dihydroxyphenyl,
u) 3-methyl-2-thiophenyl,
v) 5-methyl-2-thiophenyl,
w) 4-carboxymethylphenyl,
x) 3-cyanophenyl,
y) 4-cyanophenyl,
z) 2-pyridyl,
aa) 2-furoyl,
bb) 3-furoyl,
cc) 4-methylsulfinylphenyl,
dd) 4-trifluoromethylphenyl,
ee) 3-trifluoromethylphenyl,
ff) 4-methylphenyl,
gg) 4-t-butoxyphenyl,
hh) 3,4-dibenzyloxyphenyl, ii) 3-quinolinyl,
jj) 3-pyridyl,
kk) 4-pyridyl,
ll) 2,4-difluorophenyl,
mm) 3,4-difluorophenyl,
nn) 4-methylsulfinylphenyl,
oo) 4-methylsulfonylphenyl,
pp) 2-methoxyphenyl,
qq) 3-methoxyphenyl,
rr) 4-nitrophenyl,
ss) 4-aminomethylphenyl, and
tt) 2-chlorophenyl.

$(R^a)_b$—$Ar^2$ is selected from the group consisting of:
a) 4-(methylthio)-phenyl,
b) 4-(ethylthio)-phenyl,
c) 3-(methylthio)-phenyl,
d) 2-(methylthio)-phenyl,
e) 3-(ethylthio)-phenyl,
f) 4-methylsulfonylphenyl,
g) 4-ethylsulfonylphenyl,
h) 3-methylsulfonylphenyl,
i) 2-methylsulfonylphenyl,
j) 4-methylsulfinylphenyl,
k) 4-ethylsulfonylphenyl,
l) 3-methylsulfinylphenyl,
m) 4-(N-methyl-N-benzyl)aminomethylphenyl,
n) 3-(N-methyl-N-benzyl)aminomethylphenyl,
o) 4-methoxyphenyl,
p) 4-hydroxyphenyl,
q) 3-methoxyphenyl,
r) 2-benzyloxyphenyl,
s) 4-methylthiophen-2-yl,
t) 4-methylthiophen-3-yl,
u) 4-acetylaminophenyl,
v) 2-pyrimidinyl,
w) phenyl,
x) 4-aminomethylphenyl,
y) 4-cyanophenyl,
z) 4-fluorophenyl,
aa) 4-chlorophenyl,
bb) 4-bromophenyl,
cc) 4-carboxyethylphenyl,
dd) 2-fluorophenyl,
ee) 3-nitrophenyl,
ff) 4-nitrophenyl,
gg) 3-fluorophenyl,
hh) 4-carboxyphenyl,
ii) 4-aminophenyl,
jj) 3-aminophenyl,
kk) 4-(O(CH$_2$)$_3$NMe$_2$)-phenyl,
ll) 4-(O(CH$_2$)$_2$-piperidin-1-yl)-phenyl,
mm) 2-methoxyphenyl,
nn) 3-chlorophenyl,
oo) 4-((4-N-COCH$_3$)piperazin-1-yl)-phenyl,
pp) 4-trifluoromethylphenyl,
qq) 4-bromothiophen-2-yl,
rr) 5-methylthiophen-2-yl,
ss) 2-benzoxazolyl,
tt) 2-benzofuranyl,
uu) 2,5-dimethoxyphenyl and
vv) 4-morpholinylphenyl;
with the proviso that when $(R^a)_a$—$Ar^1$ represents a), f), g), z), aa), bb), jj) or kk), $Ar^2$—$(R^a)_b$ does not represent v), w), ss) or tt);

$(R^a)_{0-3}$—HAr is selected from the group consisting of:
a) 4-pyridyl,
b) 4-(2-methylpyridyl),
c) 4-(2-aminopyridyl),
d) 4-(2-methoxypyridyl),
e) 4-quinolinyl,
f) 4-pyrimidinyl,
g) 9-purinyl,
h) 7-(imidazo[4,5-b]pyridinyl),
i) 4-(3-methylpyridyl),
j) 2-pyridyl,
k) 3,5-dimethyl-4-pyridyl,
l) 3-quinolinyl,
m) 3-pyridazinyl,
n) 4-(2-aminobenzyl)pyridyl, and
o) 4-(2-amino)pyrimidinyl;

$R^1$ is
H; and
$R^2$ is selected from the group consisting of:
a) H,
b) F,
c) Cl,
d) Br,
e) CN,
f) C(O)C$_{1-6}$ alkyl,
g) C(O)C$_{1-6}$ alkylphenyl,
h) CO$_2$H,
i) CO$_2$C$_{1-6}$ alkyl,
j) CO$_2$C$_{1-6}$ alkylphenyl,
k) CONH$_2$,
l) CONHC$_{1-6}$ alkyl,
m) C(O)N(C$_{1-6}$ alkyl)$_2$,
n) SO$_2$NH$_2$,
o) SO$_2$NHC$_{1-6}$ alkyl and
p) SO$_2$N(C$_{1-6}$ alkyl)$_2$.

Another more preferred subset of compounds of formula I is realized when: $R^a)_a$—$Ar^1$ is selected from the group consisting of:
a) phenyl,
b) 4-fluorophenyl,
c) 4-chlorophenyl,
d) 3-fluorophenyl,
e) 3-chlorophenyl,
f) thiophen-2-yl,
g) thiophen-3-yl,
h) 4-fluorothiophen-2-yl,
i) 4-fluorothiophen-3-yl,
j) 5-fluorothiophen-2-yl,
k) 5-fluorothiophen-3-yl,
l) 4-chlorothiophen-2-yl,
m) 4-chlorothiophen-3-yl,
n) 5-chlorothiophen-2-yl,
o) 5-chlorothiophen-3-yl,
p) 3-methylphenyl,
q) 3,4-dichlorophenyl,
r) 3-hydroxyphenyl,
s) 4-hydroxyphenyl, t) 3,4-dihydroxyphenyl,
u) 3-methyl-2-thiophenyl,
v) 5-methyl-2-thiophenyl,
w) 4-carboxymethylphenyl,
x) 3-cyanophenyl,
y) 4-cyanophenyl,
z) 2-pyridyl,
aa) 2-furoyl,
bb) 3-furoyl,
cc) 4-methylsulfinylphenyl,
dd) 4-trifluoromethylphenyl,
ee) 3-trifluoromethylphenyl,
ff) 4-methylphenyl,
gg) 4-t-butoxyphenyl,
hh) 3,4-dibenzyloxyphenyl,
ii) 3-quinolinyl,
jj) 3-pyridyl,
kk) 4-pyridyl,
ll) 2,4-difluorophenyl,
mm) 3,4-difluorophenyl,
nn) 4-methylsulfinylphenyl,
oo) 4-methylsulfonylphenyl,
pp) 2-methoxyphenyl,
qq) 3-methoxyphenyl,
rr) 4-nitrophenyl,
ss) 4-aminomethylphenyl, and
tt) 2-chlorophenyl.

$(R^a)_b$—Ar$^2$ is selected from the group consisting of:
a) 4-(methylthio)-phenyl,
b) 4-(ethylthio)-phenyl,
c) 3-(methylthio)-phenyl,
d) 2-(methylthio)-phenyl,
e) 3-(ethylthio)-phenyl,
f) 4-methylsulfonylphenyl,
g) 4-ethylsulfonylphenyl,
h) 3-methylsulfonylphenyl,
i) 2-methylsulfonylphenyl,
j) 4-methylsulfinylphenyl,
k) 4-ethylsulfonylphenyl,
l) 3-methylsulfinylphenyl,
m) 4-(N-methyl-N-benzyl)aminomethylphenyl,
n) 3-(N-methyl-N-benzyl)aminomethylphenyl,
o) 4-methoxyphenyl,
p) 4-hydroxyphenyl,
q) 3-methoxyphenyl,
r) 2-benzyloxyphenyl,
s) 4-methylthiophen-2-yl,
t) 4-methylthiophen-3-yl,
u) 4-acetylaminophenyl,
v) 2-pyrimidinyl,
w) phenyl,
x) 4-aminomethylphenyl,
y) 4-cyanophenyl,
z) 4-fluorophenyl,
aa) 4-chlorophenyl,
bb) 4-bromophenyl,
cc) 4-carboxyethylphenyl,
dd) 2-fluorophenyl,
ee) 3-nitrophenyl,
ff) 4-nitrophenyl,
gg) 3-fluorophenyl,
hh) 4-carboxyphenyl,
ii) 4-aminophenyl,
jj) 3-aminophenyl,
kk) 4-(O(CH$_2$)$_3$NMe$_2$)-phenyl,
ll) 4-(O(CH$_2$)$_2$-piperidin-1-yl)-phenyl,
mm) 2-methoxyphenyl,
nn) 3-chlorophenyl,
oo) 4-((4-N—COCH$_3$)piperazin-1-yl)-phenyl,
pp) 4-trifluoromethylphenyl,
qq) 4-bromothiophen-2-yl,
rr) 5-methylthiophen-2-yl,
ss) 2-benzoxazolyl,
tt) 2-benzofuranyl,
uu) 2,5-dimethoxy-phenyl and
vv) 4-morpholinylphenyl;
with the proviso that when $(R^a)_a$—Ar$^1$ represents a), f), g), z), aa), bb), jj) or kk) Ar$^2$—$(R^a)_b$ does not represent v), w), ss) or tt);

$(R^a)_{0-3}$—HAr is selected from the group consisting of:
a) 4-pyridyl,
b) 4-(2-methylpyridyl),
c) 4-(2-aminopyridyl),
d) 4-(2-methoxypyridyl),
e) 4-quinolinyl,
f) 4-pyrimidinyl,
g) 9-purinyl,
h) 7-(imidazo[4,5-b]pyridinyl),
i) 4-(3-methylpyridyl),
j) 2-pyridyl,
k) 3,5-dimethyl-4-pyridyl,
l) 3-quinolinyl,
m) 3-pyridazinyl,
n) 4-(2-aminobenzyl)pyridyl, and
o) 4-(2-amino)pyrimidinyl;

R$^1$ is:
a) substituted or unsubstituted C$_{1-15}$ alkyl; and

R$^2$ is selected from the group consisting of:
a) H,
b) F,
c) Cl,
d) Br,
e) CN;
f) C(O)C$_{1-6}$ alkyl;
g) C(O)C$_{1-6}$ alkylphenyl;
h) CO$_2$H;
i) CO$_2$C$_{1-6}$ alkyl
j) CO$_2$C$_{1-6}$ alkylphenyl;
k) CONH$_2$;
l) CONHC$_{1-6}$ alkyl;
m) C(O)N(C$_{1-6}$ alkyl)$_2$;
n) SO$_2$NH$_2$;
o) SO$_2$NHC$_{1-6}$ alkyl and
p) SO$_2$N(C$_{1-6}$ alkyl)$_2$.

A further subset of compounds of the invention includes compounds represented by formula I:

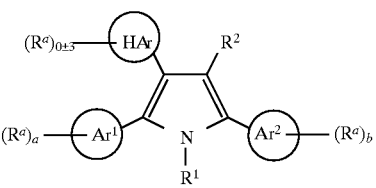

wherein:

and

each independently represent a 5–10 membered aryl or heteroaryl group;
a and b represents integers, 0, 1, 2 or 3, such that the sum of a plus b is 1, 2, 3 or 4;

represents a heteroaryl group containing from 5 to 10 atoms, 1–3 of which are heteroatoms, 0–3 of which heteroatoms are N and 0–1 of which are O or S, said heteroaryl group being unsubstituted or substituted with 1–3 $R^a$ groups;

each $R^a$ independently represents a member selected from the group consisting of: halo; CN, $NO_2$, $R^{21}$; $OR^{23}$; $SR^{23}$; $S(O)R^{21}$; $SO_2R^{21}$; $NR^{20}R^{23}$; $NR^{20}COR^{21}$; $NR^{20}CO_2R^{21}$; $NR^{20}CONR^{20}R^{23}$; $NR^{20}SO_2R^{21}$; $NR^{20}C(NR^{20})NHR^{20}$, $CO_2R^{23}$; $CONR^{20}R^{23}$; $SO_2NR^{20}R^{23}$; $SO_2NR^{20}COR^{21}$; $SO_2NR^{20}CONR^{20}R^{23}$; $SO_2NR^{20}CO_2R^{21}$; $OCONR^{20}R^{23}$; $OCONR^{20}SO_2R^{20}$, $C(O)OCH_2OC(O)R^{20}$ and $C(NR^{20})NR^{20}R^{23}$;

$R^1$ is selected from the group consisting of: H, aryl, $C_{1-15}$ alkyl, $C_{2-15}$ alkenyl, $C_{2-15}$ alkynyl, and heterocyclyl, said alkyl, aryl, alkenyl, alkynyl and heterocyclyl being optionally substituted with from one to three members selected from the group consisting of: aryl, heteroaryl, heterocyclyl, $OR^{20}$, $SR^{20}$, $N(R^{20})_2$, $S(O)R^{21}$, $SO_2R^{21}$, $SO_2N(R^{20})_2$, $SO_2NR^{20}COR^{21}$, $SO_2NR^{20}CON(R^{20})_2$, $NR^{20}COR^{21}$, $NR^{20}CO_2R^{21}$, $NR^{20}CON(R^{20})_2$, $N(R^{20})C(NR^{20})NHR^{20}$, $CO_2R^{20}$, $CON(R^{20})_2$, $CONR^{20}SO_2R^{21}$, $NR^{20}SO_2R^{21}$, $SO_2NR^{20}CO_2R^{21}$, $OCON(R^{20})_2$, $OCONR^{20}SO_2R^{21}$ and $OCONR^{20}R^{23}$;

$R^2$ is selected from the group consisting of: H, $C_{1-15}$ alkyl, $C_{2-15}$ alkenyl, $C_{2-15}$ alkynyl, halo, $NO_2$ and heterocyclyl, said alkyl, alkenyl, alkynyl and heterocyclyl being optionally substituted with from one to three members selected from the group consisting of: halo, heterocyclyl, CN, aryl, heteroaryl, $R^{20}$, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$ and $OCONR^{20}R^{23}$;

$R^{20}$ represents a member selected from the group consisting of: H, $C_{1-15}$ alkyl, $C_{2-15}$ alkenyl, $C_{2-15}$ alkynyl, heterocyclyl, aryl and heteroaryl, said alkyl, alkenyl and alkynyl being optionally substituted with 1–3 groups selected from halo, aryl and heteroaryl;

$R^{21}$ represents a member selected from the group consisting of: $C_{1-15}$ alkyl, $C_{2-15}$ alkenyl, $C_{2-15}$ alkynyl, heterocyclyl, aryl and heteroaryl, said alkyl, alkenyl, alkynyl, aryl and heteroaryl being optionally substituted with from 1–3 of halo, heterocyclyl, aryl, heteroaryl, CN, $OR^{20}$, $O((CH_2)_nO)_mR^{20}$, $NR^{20}((CH_2)_nO)_mR^{20}$ wherein n represents an integer of from 2 to 4, and m represents an integer of from 1 to 3; heterocyclyl, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}OC(O)R^{20}$, $C(O)OCH_2OC(O)R^{20}$ and $OCON(R^{20})_2$;

$R^{22}$ is selected from the group consisting of: $C_{1-15}$ alkyl, $C_{2-15}$ alkenyl, $C_{2-15}$ alkynyl, heterocyclyl, aryl and heteroaryl, said alkyl, alkenyl, and alkynyl being optionally substituted with 1–3 halo, aryl or heteroaryl groups;

$R^{23}$ is $R^{21}$ or H;

$R^{24}$ is selected from $COR^{22}$, $CO_2R^{22}$, $CON(R^{20})_2$, $SO_2R^{22}$ and $R^{23}$;

and when two $R^{20}$ groups are present, when $R^{20}$ and $R^{21}$ are present, or when $R^{20}$ and $R^{23}$ are present, said two $R^{20}$ groups, $R^{20}$ and $R^{21}$ or said $R^{20}$ and $R^{23}$ may be taken in combination with the atoms to which they are attached and any intervening atoms and represent heterocyclyl containing from 5–10 atoms, at least one atom of which is a heteroatom selected from O, S or N, said hetercyclyl optionally containing 1–3 additional N atoms and 0–1 additional O or S atom.

Another subset of compounds of the invention includes compounds wherein $Ar^1$ and $Ar^2$ are independently selected from:
a) phenyl,
b) pyridyl,
c) pyrimidinyl,
d) thiophenyl,
e) furanyl,
f) imidazolyl,
g) thiazolyl,
h) isothiazolyl,
i) oxazolyl,
j) isoxazolyl and
k) napthyl;

HAr is selected from the group consisting of:
a) pyridyl,
b) quinolyl,
c) purinyl,
d) imidazolyl,
e) imidazopyridine and
f) pyrimidinyl;

$R^1$ is:
a) H or
b) substituted alkyl; and $R^2$ is selected from the group consisting of:
a) H, or
b) alkyl and
c) halo.

Still another subset of compounds of the invention includes compounds wherein $Ar^1$ is selected from the group consisting of:
a) phenyl,
b) 4-fluorophenyl,
c) 4-chlorophenyl, d) 3-fluorophenyl,
e) 3-chlorophenyl,
f) thiophen-2-yl,
g) thiophen-3-yl,
h) 4-fluorothiophen-2-yl,
i) 4-fluorothiophen-3-yl,
j) 5-fluorothiophen-2-yl,
k) 5-fluorothiophen-3-yl,
l) 4-chlorothiophen-2-yl,
m) 4-chlorothiophen-3-yl,
n) 5-chlorothiophen-2-yl,
o) 5-chlorothiophen-3-yl,
p) 3-methyl phenyl,
q) 3,4 dichlorophenyl and
r) 3-hydroxyphenyl;

$(R^a)_b$—$Ar^2$ is selected from the group consisting of:
a) 4-(methylthio)-phenyl,
b) 4-(ethylthio)-phenyl,
c) 3-(methylthio)-phenyl,
d) 2-(methylthio)-phenyl,
e) 3-(ethylthio)-phenyl,
f) 4-methylsulfonylphenyl,
g) 4-ethylsulfonylphenyl,
h) 3-methylsulfonylphenyl,
i) 2-methylsulfonylphenyl,
j) 4-methylsulfinylphenyl,
k) 4-ethylsulfonylphenyl,
l) 3-methylsulfinylphenyl,
m) 4-(N-methyl-N-benzyl)aminomethylphenyl,
n) 3-(N-methyl-N-benzyl)aminomethylphenyl,
o) 4-methoxyphenyl,
p) 4-hydroxyphenyl,
q) 3-methoxyphenyl,
r) 2-benzyloxyphenyl,
s) 4-methylthiophen-2-yl,
t) 4-methylthiophen-3-yl,
u) 4-acetylaminophenyl and
v) 2-pyrimidinyl;

$(R^a)_{0-3}$—HAr is selected from the group consisting of:
a) 4-pyridyl,
b) 4-(2-methylpyridyl),
c) 4-(2-aminopyridyl),
d) 4-(2-methoxypyridyl),
e) 4-quinolinyl,
f) 4-pyrimidinyl,
g) 9-purinyl,
h) 7-(imidazo[4,5-b]pyridinyl), and
i) 4-(3-methylpyridyl)

$R^1$ is:
H and
$R^2$ is selected from the group consisting of:
a) H,
b) F,
c) Cl and
d) Br.

The pharmaceutically acceptable salts of the compounds of formula I include the conventional non-toxic salts or the quarternary ammonium salts of the compounds of formula I formed e.g. from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic and the like.

The pharmaceutically acceptable salts of the present invention can be synthesized from the compounds of formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The compounds of the present invention may have asymmetric centers and occur as racemates, racemic mixtures, and as individual diastereomers, with all possible isomers, including optical isomers, being included in the present invention.

This invention also relates to a method of antagonizing or inhibiting the production or activity of cytokines in a mammal in need thereof which comprises administering to said mammal an effective amount of a compound of formula I to antagonize or inhibit cytokine production or activity such that it is regulated down to normal levels, or in some cases to subnormal levels, so as to ameliorate or prevent the disease state.

The compounds of formula 1 can be used in the manufacture of a medicament for the prophylactic or therapeutic treatment of disease states in mammals, which are exacerbated or caused by excessive or unregulated cytokines production, more specifically IL-1, IL-6, IL-8 or TNF, by such mammal's cells, such as but not limited to monocytes and/or macrophages.

Compounds of formula I inhibit cytokines, such as IL-1, IL-6, IL-8 and TNF and are therefore useful for treating inflammatory diseases, such as rheumatoid arthritis, rheumatoid spondylitis, osteoarthritis, gouty arthritis and other arthritic conditions.

The compounds of formula I may be used to treat other disease states mediated by excessive or unregulated cytokine production or activity. Such diseases include, but are not limited to sepsis, e.g., gram negative sepsis, septic shock, endotoxic shock, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft vs. host reaction, allograft rejection, fever and myalgia due to infection, such as influenza, cachexia secondary to infection or malignancy, cachexi, secondary to acquired immune deficiency syndrome (AIDS), AIDS and other viral infections, ARC (AIDs related complex), keloid formation, scar tissue formation, Crohn's disease, ulcerative colitis, pyresis, such as cytomegalovirus (CMV), influenza virus and the herpes family of viruses such, as Herpes Zoster or Simplex I and II.

The compounds of formula I may also be used in the treatment of inflammation such as for the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds of formula I are normally formulated as pharmaceutical compositions, which are comprised of a compound of formula I and a pharmaceutically acceptable carrier. The compounds of formula I may also be administered in combination with a second therapeutically active compound. These procedures may involve mixing, granulating and compressing or dissolving the ingredients as appropriate to the desired preparation.

The pharmaceutical carrier employed may be, for example, solid or liquid. Solid carriers include lactose, terra alba, sucrose, talc, gelatin, agar, pectin, acacia, magnesium stearate, stearic acid and the like. Liquid carriers include syrup, peanut oil, olive oil, water and the like. Similarly, the carrier may include time delay material, such as glyceryl monostearate or glyceryl distearate, alone or with a wax.

A wide variety of pharmaceutical forms can be employed. Thus, if a solid dosage form is used, the preparations typically be in the form of a tablet, hard gelatin capsule, a troche or lozenge. The amount of solid will vary widely but preferably will be from about 0.025 mg to about 1 g. When a liquid dosage form is used, the preparation is typically in the form of a syrup, emulsion, soft gelatin capsule, sterile injectable liquid or nonaqueous liquid suspension.

The compounds of formula I may also be administered topically in the form of a liquid, solid or semi-solid. Liquids include solutions, suspensions and emulsions. Solids include powders, poultices and the like. Semi-solids include creams, ointments, gels and the like.

The amount of a compound of formula I, for the methods of use disclosed herein, vary with the compound chosen, the nature and severity of the condition, and other factors. A representative, topical dose of a compound of formula I is from about 0.01 mg to about 1500 mg, administered one to four, preferably one to two times daily.

While it is possible for an active ingredient to be administered alone as the raw chemical, it is preferable to present it as a pharmaceutical formulation. The active ingredient typically comprises about 0.001% to about 90% w/w.

Drops according to the present invention may comprise sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98°–100° C. for half an hour. Alternatively, the solution may be sterilized by filtration and transferred to the container by aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as steric or oleic acid together with an alcohol such as propylene glycol or macrogels. The formulation may incorporate any suitable surface active agent such as an anionic, cationic or non-ionic surfactant such as sorbitan esters or poly-oxyethylene derivatives thereof. Suspending agents such as natural gums, cellulose derivatives or inorganic materials such as silicas, and other ingredients such as lanolin may also be included.

The methods of the instant invention may also be carried out by delivering the agent parenterally. The term 'parenteral' as used herein includes intravenous, intramuscular, or intradermal and subcutaneous administration. The intravenous and intramuscular forms of administration are preferred. Appropriate dosage forms for such administration may be prepared as described above. The instant invention can also be carried out by delivering the compounds of formula I intranasally, rectally, transdermally or vaginally.

The compounds of formula I may be administered by inhalation. By 'inhalation' is meant intranasal and oral inhalation administration. Appropriate dosage forms for such administration, include an aerosol formulations and metered dose inhalers.

Compounds of formula I are prepared (see Scheme I) by the reaction of compound 1, or a protected version thereof with an acetophenone (commercially available) in the presence of potassium cyanide followed by treatment with an alkyl or aryl amine, ammonia or equivalent thereof (ammonium acetate) at elevated temperature.

SCHEME I

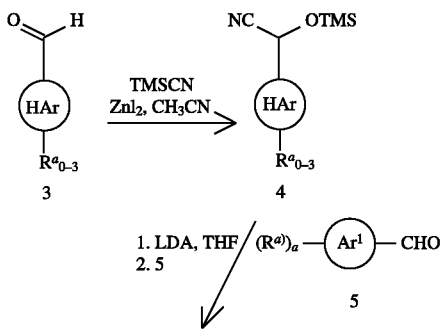

-continued
SCHEME I

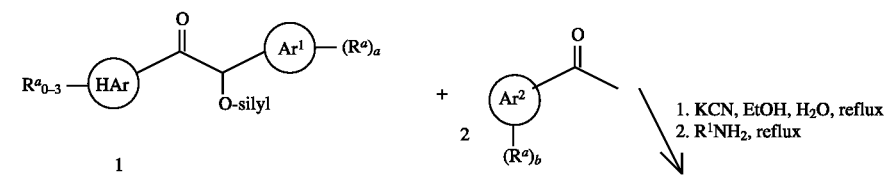

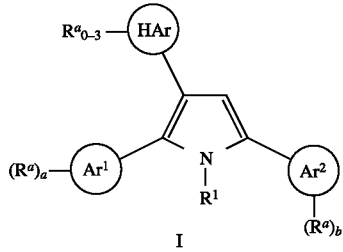

Heteroaromatic aldehydes 3 may be converted to their trimethylsilyl cyanohydrins 4. Deprotonation and reaction with an aldehyde 5 will provide trimethyl silyl protected benzoins 1. (See, e.g., Hunig, S.et al., Chem. Ber. 112, 2062 (1979)).

SCHEME II

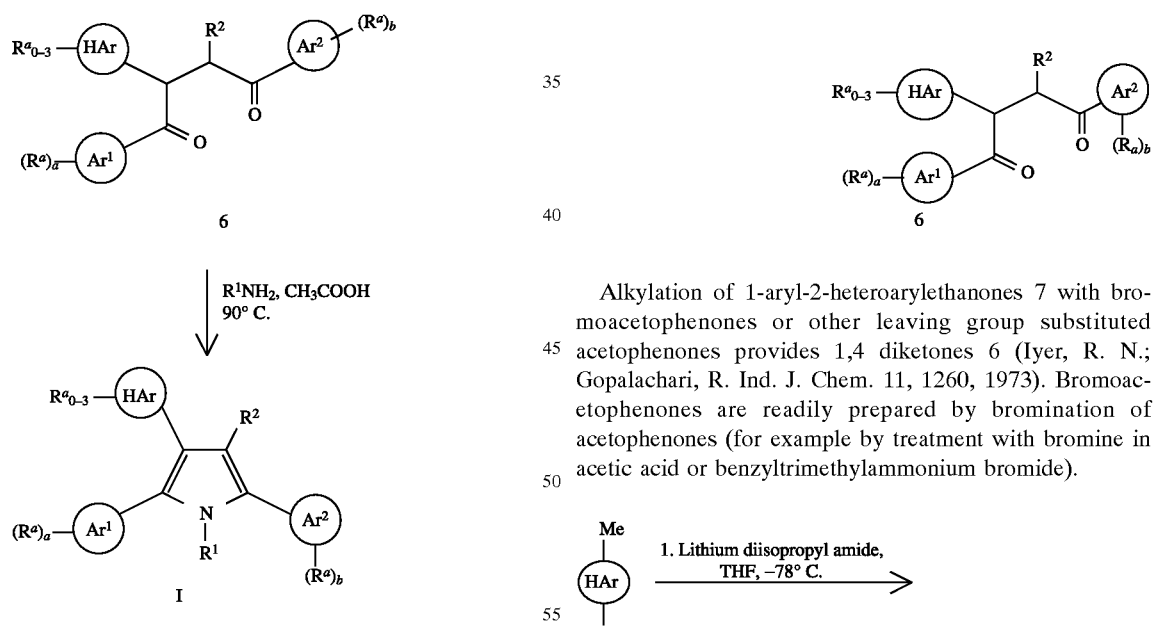

Condensation of the 1,4-diketone 6 with ammonia or an amine gives rise to pyrroles (Paal Knor Synthesis). Compound 6, a 1,4-diketone, (see Scheme II) is reacted with ammonia, or a compound that gives rise to ammonia such as ammonium acetate or a primary amine, to provide compounds of formula I. This reaction can be conducted in the presence of an acid catalyst, such as acetic acid, or titanium tetrachloride at an elevated temperature. 1,4-diketone 6 is thus regioselectively constructed so that the appropriate groups are present on the pyrrole ring.

Alkylation of 1-aryl-2-heteroarylethanones 7 with bromoacetophenones or other leaving group substituted acetophenones provides 1,4 diketones 6 (Iyer, R. N.; Gopalachari, R. Ind. J. Chem. 11, 1260, 1973). Bromoacetophenones are readily prepared by bromination of acetophenones (for example by treatment with bromine in acetic acid or benzyltrimethylammonium bromide).

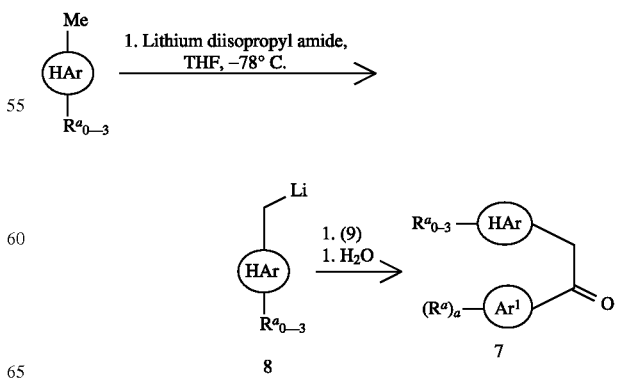

-continued

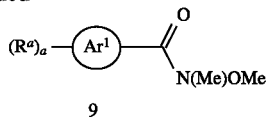
9

Ethanone 7 is prepared by the addition of a heteroaryl methyl anion 8 to an activated benzoic acid 9 (for example esters, acid chlorides, nitriles and N-methoxy-N-methyl amides) (see: Wolfe, J. F. et al *J. Org. Chem.* 39, 2006 1974 and Kaiser, E. M. et al *Synthesis* 705 1975 and Ohsawa A. *Chem. Pharm. Bull.* 26, 3633, 1978).

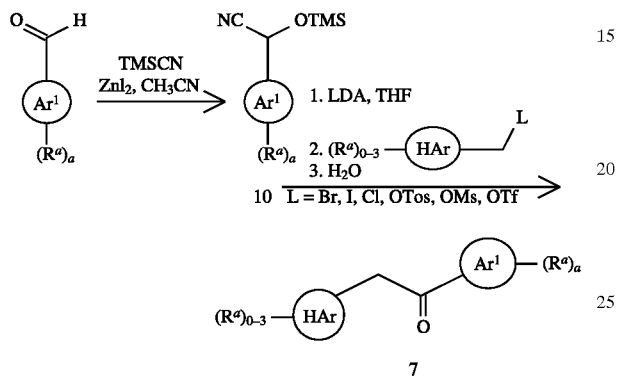

Compound 7 may also be prepared by alkylation of aryl trimethyl silyl protected cyanohydrins 10. Treatment of 10 with lithium diisopropyl amide in THF and addition of a heteroaryl methyl group functionalized with a leaving group L (for example: Br, I, Cl, tosylate, mesylate) followed by acid catalyzed hydrolysis of the silyl cyanohydrin group provides ethanone 7 (Deuchert, K.; Hertenstein, U.; Hunig, S.; Wehner, G. Chem. Ber. 112, 2045, 1979).

SCHEME III

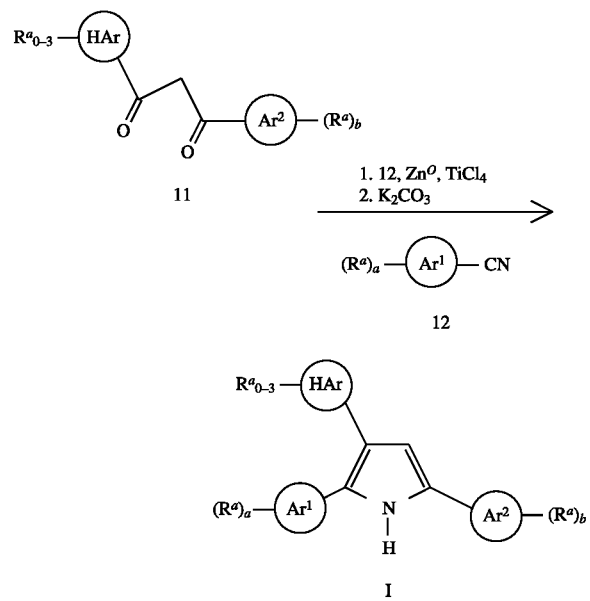

The reductive cross coupling of a 1,3 diketone 11 with a nitrile 12 in the presence of zinc and titanium tetrachloride also gives rise to compounds of formula I, See Scheme III, (Gao, J. Hu, M.; Chen, J.; Yuan, S.; Chen, W. Tet Lett. 34, 1617, 1993). The 1,3 diketone 11 may be prepared by alkylation of 4 with bromoacetophenones.

SCHEME IV

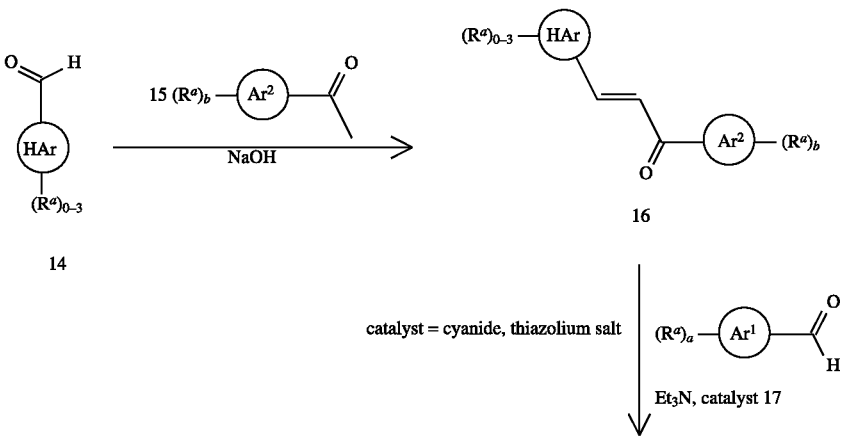

SCHEME IV

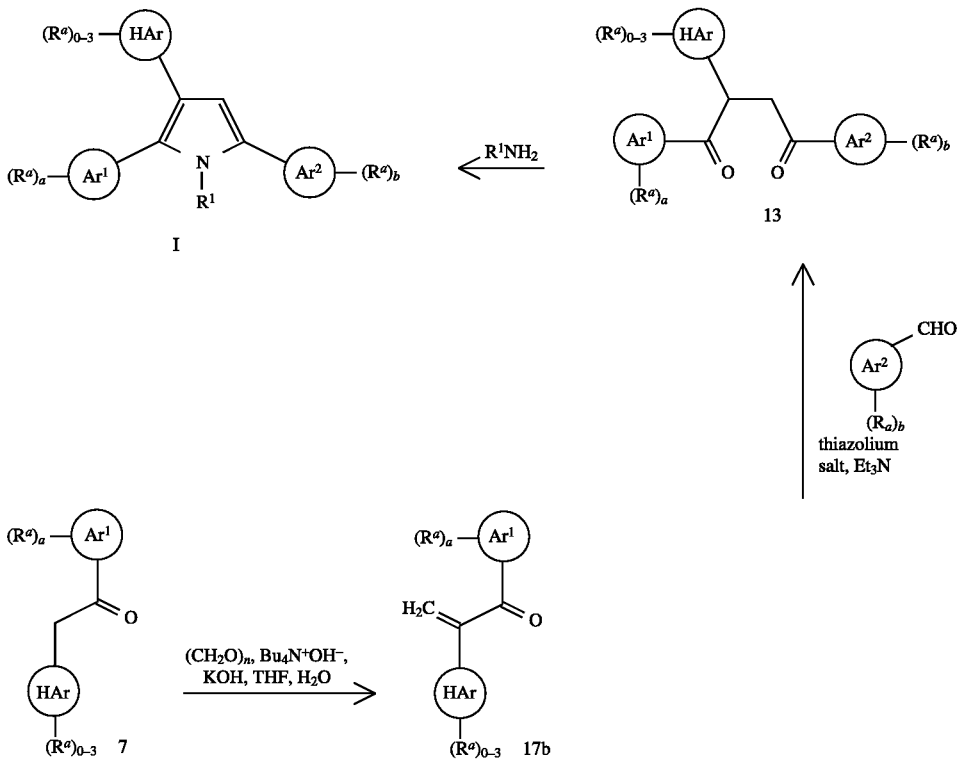

The 1,4 diketone 13 can also be prepared as described in Scheme IV. A heteroaryl aldehyde 14 is condensed with a methyl ketone 15 to provide an α,β-unsaturated ketone 16. In the presence of a catalyst such as cyanide or a thiazolium salt the aryl aldehyde 17 reacts with 16 to give 13 (Stetter, H. J. et al Heterocyclic Chem. 14, 573, 1977 and Stetter, H. et. al. Organic Reactions, Vol. 40, 407–496). Condensation of 13 with an amine provides compounds of formula I. Alternatively, variations of $Ar^2$ may be introduced by addition of $Ar^2$ aldehydes to alkenes 17b that are readily available from the ketones 7 described above.

SCHEME V

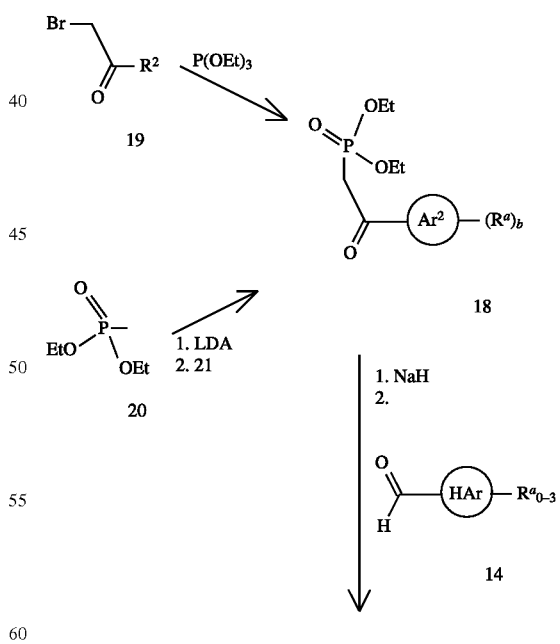

-continued
SCHEME V

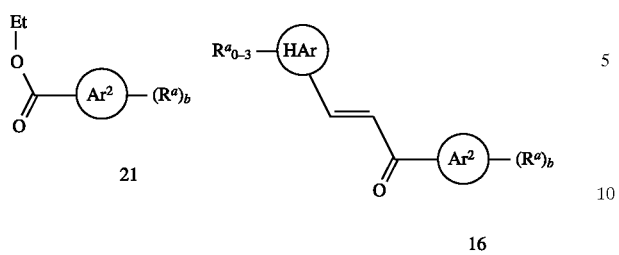

Intermediate 16 may be prepared by a Horner-Emmons reaction of the anion of 18 with the heteroaryl aldehyde 14. The reagent 18 may be prepared by reaction of the bromoketone 19 and triethyl phosphite or by reaction of the lithium salt of diethyl methylphosphonate with an ester 21.

SCHEME VI

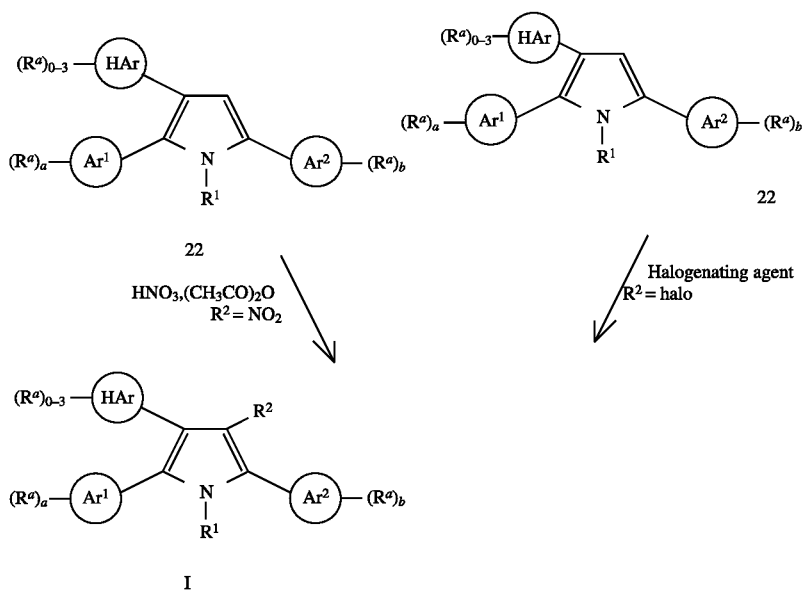

A nitro group may be introduced into the pyrrole nucleus at the 3 position (generic nomenclature-$R^2$) by electrophilic nitration of a compound such as 22 (or a less advanced intermediate) in the presence of fuming nitric acid and acetic anhydride.

Halogens may be introduced by electrophilic halogation with reagents such as $XeF_2$ ($R^2$=F), N-chlorosuccinimide in DMF ($R^2$=Cl), N-bromosuccinimide in DMF ($R2^3$=Br), $I_2$ in KI ($R^2$=I). Other reagents are available to carry out this conversion, the choice of reagent being dependent on the presence of functional groups that may be sensitive to the reagent being utilized. See e.g., Pyrroles Part 1, R. Alan Jones, ed., *Heterocyclic Compounds*, Vol 48 Part 1, John Wiley, New York, 1990. Pages 348–391.

SCHEME VII

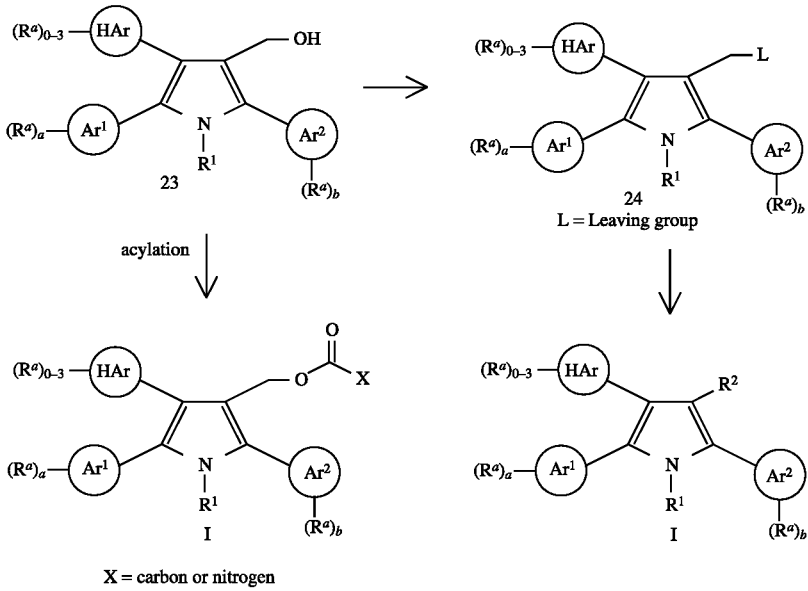

X = carbon or nitrogen

Introduction of alkyl and heterocyclyl alkyl groups at the 3 position is described. Direct introduction is possible as described in the use of 1,4 diketone 6 as a precursor of compounds of formula I. The preparation of the pyrrole 23 containing a hydroxy methyl group at position 3 ($R^2$) provides an intermediate that is readily elaborated into compounds of formula I.

Acylation of the hydroxyl group with activated acids or isocyanates provides esters and carbamates respectively of formula I. Conversion of the hydroxy group into a leaving group 24 (for example Br, I, Cl, triflate, etc.) enables the introduction of alkyl, heterocyclyl and amines and thiol groups by displacement with a nucleophile. Suitable nucleophiles include for example, an alkyl or heterocyclyl anion, a primary or secondary amine or a thiol.

SCHEME VIII

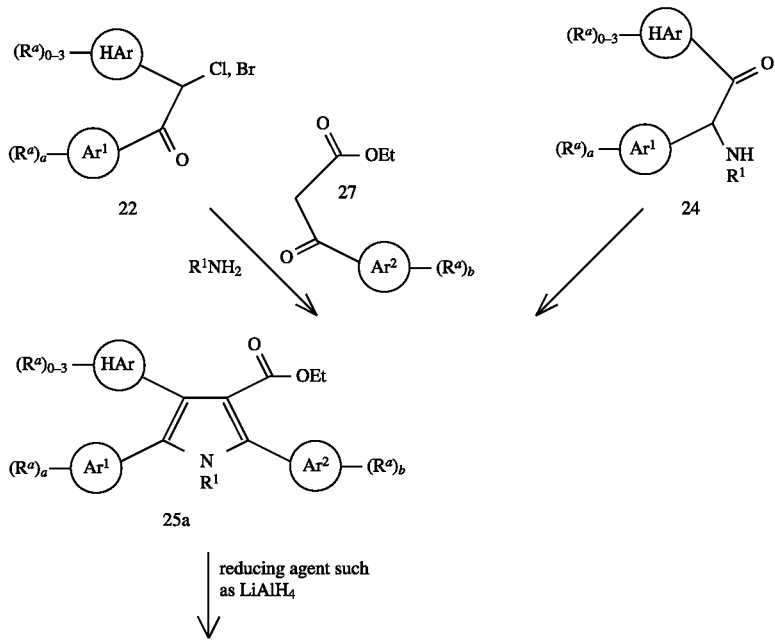

SCHEME VIII -continued

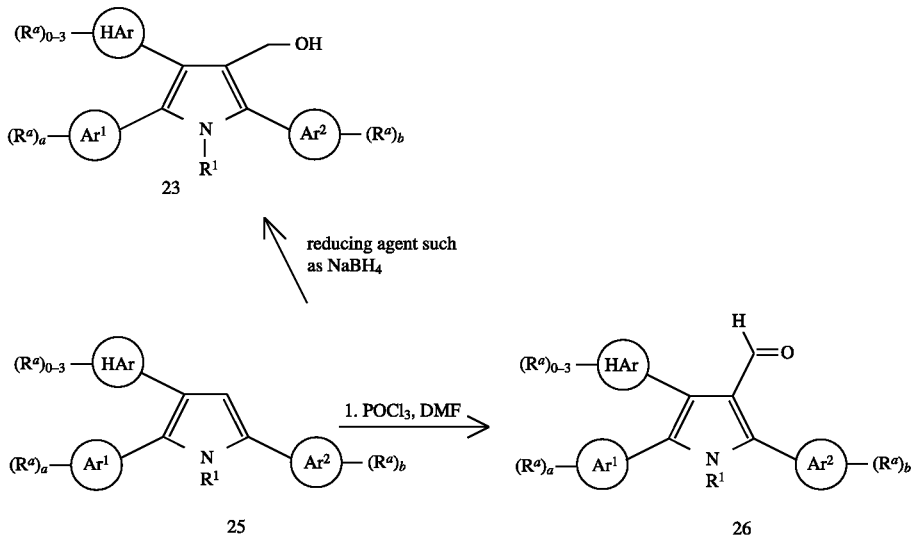

Hydroxy methyl substituted pyrroles 23 may be prepared by reduction of esters 25a through the reaction with a reducing agent such as lithium aluminum hydride. The ester 25a may be prepared by treatment of 1,2-disubstituted-2 halo ketones 22 with 3-keto esters 27 and ammonia or an amine, producing ester 25a (Hantzsch. Ber. Dtsch. Chem. Ges. 23, 1474, 1890). Alternatively, a 2-amino ketone 24 reacts with a 3-keto ester 27 to produce 25.

A further method of synthesis of 23 is via reduction of the aldehyde 26 with a reducing agent such as sodium borohydride. The aldehyde may be prepared by treatment of the $R^3$-unsubstituted pyrrole 25 with the Villsmeyer reagent ($POCl_3$/DMF).

SCHEME IX

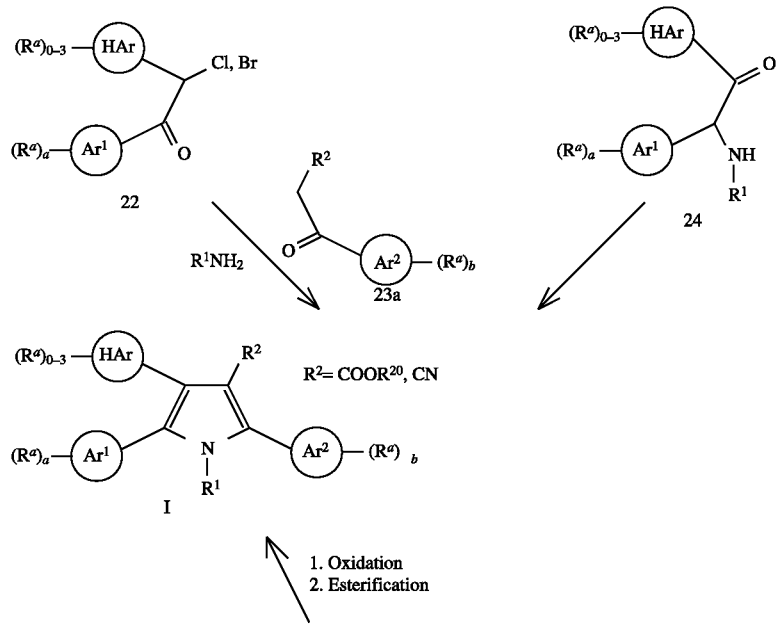

SCHEME IX -continued

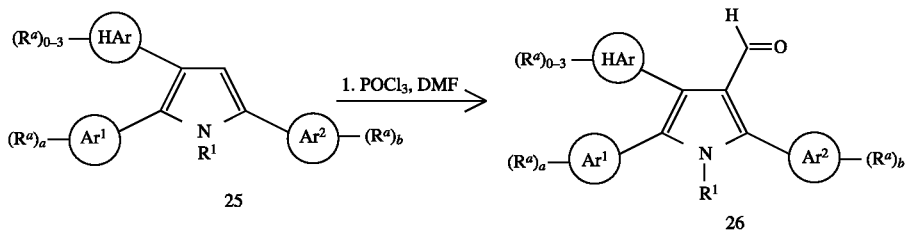

The ester and nitrile of formula I may be prepared as shown in Scheme IX by treatment of halo ketones 22 with keto esters or keto nitriles 23a with ammonia or an amine producing ester I (Hantzsch. Ber. Dtsch. Chem. Ges. 23, 1474, 1890). Alternatively a 2-amino ketone 24 reacts with a 3-keto ester 23a to produce I. A further method of synthesis of Compounds of formula I is by oxidation and esterification of aldehyde 26. The aldehyde is prepared by treatment of the pyrrole 25 with the Villsmeyer reagent ($POCl_3$/DMF).

SCHEME X

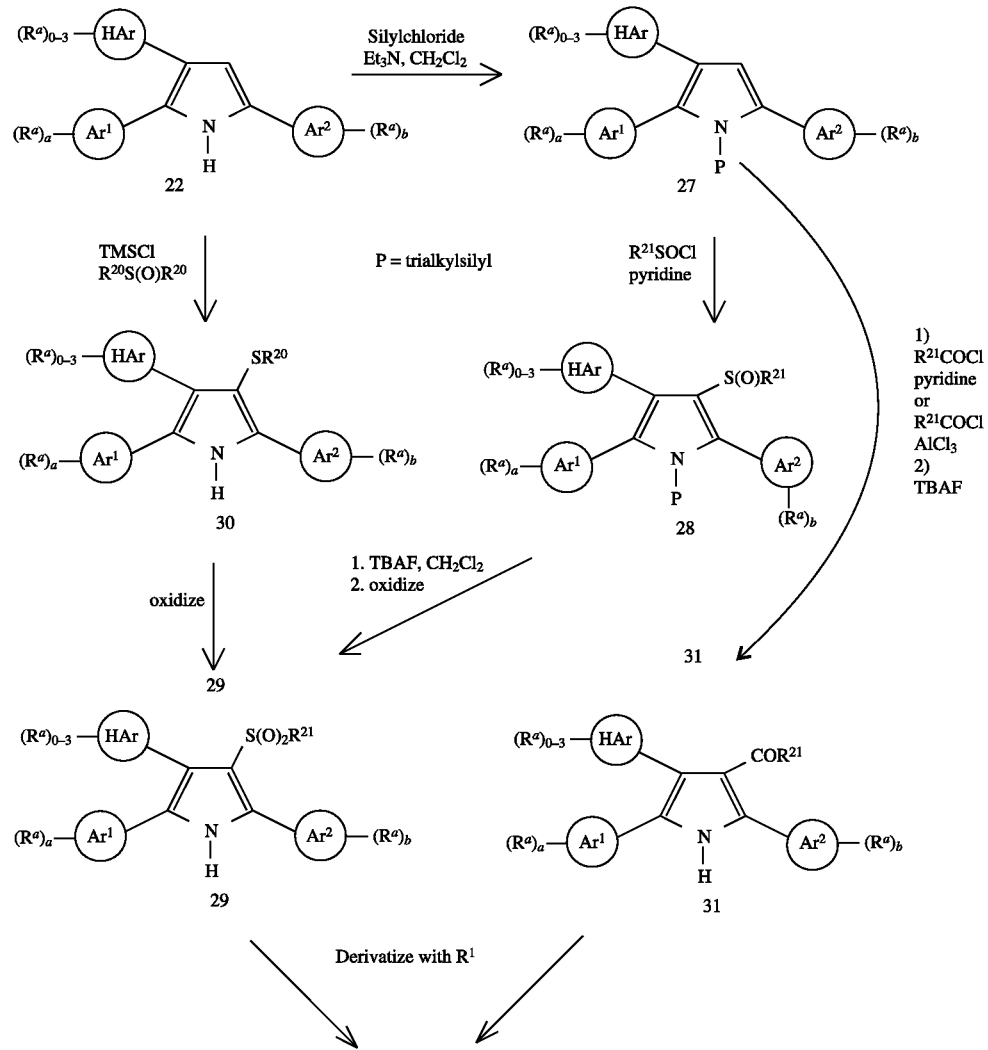

-continued
SCHEME X

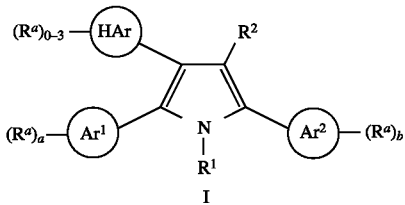

The pyrrole 22 prepared as described herein may be silylated on the nitrogen atom to give 27 by treatment with a silyl chloride and base in a solvent such as methylene chloride. The pyrrole 27 may then be sulphenylated with a sulphenylchloride under basic conditions to provide 28 (J. Org. Chem. 6317 1990). Oxidation of 28 with a reagent such as m-chloroperoxybenzoic acid will give the sulphone 29. Removal of the silyl group and derivatization of the pyrrole will give compounds of Formula I. Compound 22 may also be converted to the sulphide 30 by reaction of 22 with a symmetrical sulfoxide in the presence of trimethylsilylchloride (TMSCl) to give 30. Oxidation of 30 with a reagent such as m-chloroperoxybenzoic acid will give 29. The silyl pyrrole 27 may also be acylated with an acid chloride to give the ketone 31.

Removal of the silyl group from 29 and 31 and derivatization of the pyrrole will give compounds of formula I. Pyrroles such as 22 may also be sulfinylated directly without N-protection, by treatment with sulphinyl chloride in a solvent such as dichloromethane at 0° C. (J. Org. Chem. 5336, 1980). Oxidation as described above thus provides pyrroles of formula I where $R^3$ is $SO_2R^{21}$.

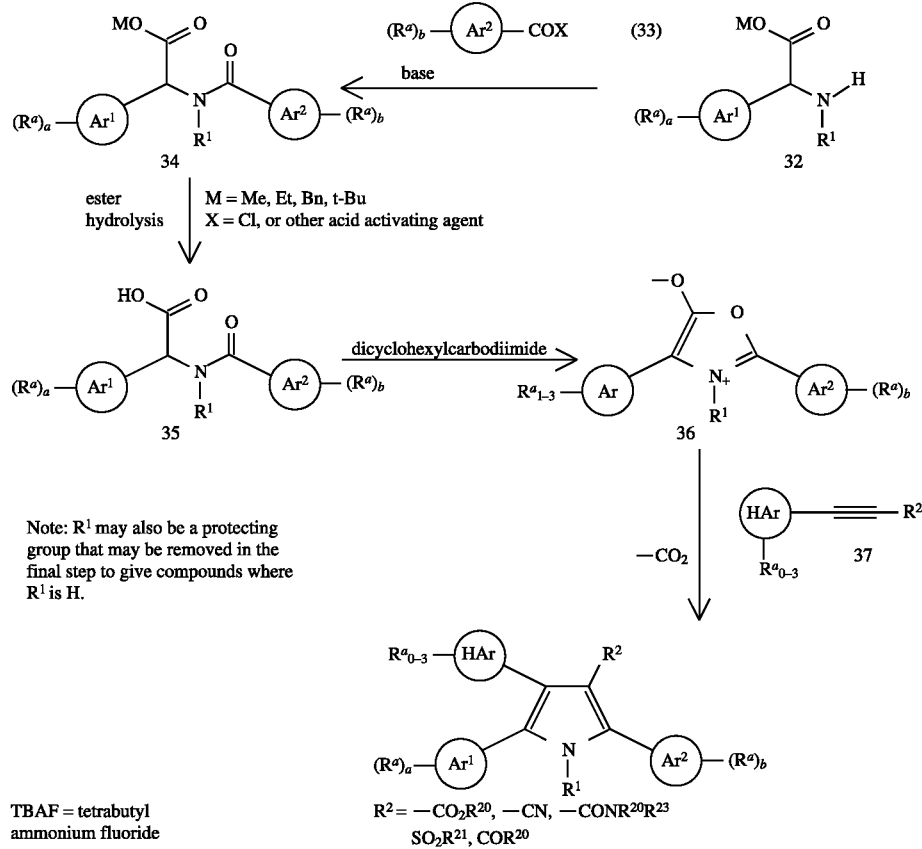

The amino acid ester 32 may be acylated with an acid 33 that is suitably activated (acid chloride or other activating group used in amide coupling reactions) to give 34 (Scheme XI). Hydrolysis of the ester protecting group will provide 35. Cyclization by treatment with an acid activating group such as dicyclohexylcarbodiimide (DCC) will give the oxazolium species 36. Addition of an alkyne 37 to 36 may give a pyrrole of Formula I via a 3+2 cycloaddition followed by loss of carbon dioxide. Various R³ groups may be incorporated in this manner.

SCHEME XII

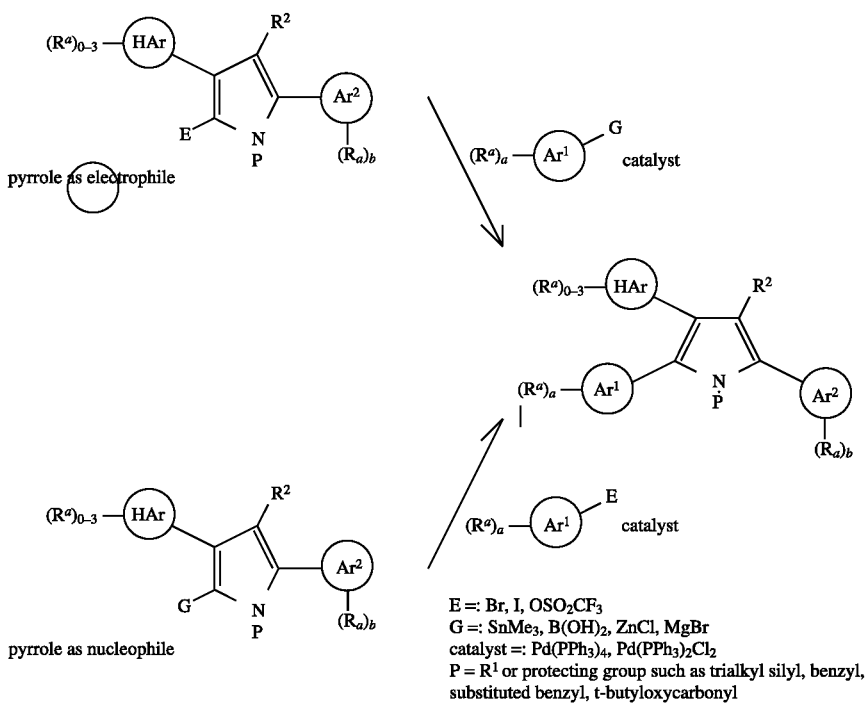

Aryl and heteroaryl rings may also be appended to the pyrrole ring system by utilization of organometallic coupling technology (Kalinin, V. *Synthesis* 413 1991). See Scheme XIII. The pyrrole ring may function as an electrophile or as a nucleophile.

Any of the three appended aromatic or heteroaromatic rings may be attached to the pyrrole ring system (Alvarez, A. J. et al. *J. Org. Chem.* 1653, 1992 (use of boronic acid and tributyl stannanes for coupling to aromatic and heteroaromatic rings)). Attachment of pyrrole pendant groups may be carried out with or without other Ar, HAr, R² or R³ groups attached.

The synthesis of pyrroles containing nucleophilic groups for coupling reactions depends on the pyrrole substitution pattern. Lithium anions are prepared by metalation of a regioselectively halogenated pyrrole, or the regioselective deprotonation of the pyrrole preferably by the use of a directing functional group. The resulting anion may then be trapped by a trialkyl stannyl halide or a trialkyl borate or transmetalated to magnesium or zinc by treatment with appropriate halide salts. A further method used to incorporate a trialkyl stannyl group is the coupling of a bromo, iodo or triflate substituted pyrrole with hexalkylditin in the presence of a palladium catalyst.

The synthesis of pyrroles incorporating electrophilic groups may be carried out by the regioselective halogenation of a pyrrole (Pyrroles Part 1, R. Alan Jones, ed., *Heterocyclic Compounds* Vol 48 Part 1, John Wiley, New York, 349–391, 1990). The regioselectivity of halogenation will depend on the size, nature and substitution position on the pyrrole ring as well as the presence or absence of the N-alkyl protecting group. Triflates may be prepared by acylation of hydroxy pyrroles with triflic anhydride.

The reaction conditions used will depend on the nature of the coupling species. In the case of magnesium, zinc and stannyl coupling reactions the solvent employed is toluene, or DMF under anhydrous conditions. In the case of boronic acid couplings, a heterogenous system is used of water, toluene, and dimethoxyethane, or ethanol in the presence of a base such as sodium carbonate, or bicarbonate. In general, the reaction takes place at an elevated temperature (80°–100° C.,). The catalysts used will most likely depend on the structure of the components to be coupled as well as the functional groups and belong to the group consisting of tetrakistriphenylphosphinepalladium (O), or palladium bis triphenyl phosphine dichloride.

Coupling of alkenes or alkynes with 4-halo pyrroles (Heck reaction, see Kalinin, V. Synthesis 413 1991 for a review) will give rise to R² (generic nomenclature) alkenyl and alkynyl substituted pyrroles that may be reduced or otherwise modified to provide compounds of formula I.

Functional groups such as halogens, sulfides, nitro groups, ethers and other groups stable to the reaction conditions used in the linear synthesis of the pyrroles are incorporated in the initial steps of the reaction sequence. Sulfides may be oxidized to sulfoxides and sulfones with reagents such as m-chloroperbenzoic acid. Sulfides may also be converted to sulfonyl chlorides by oxidation and chlorination by chlorine in water.

Primary amines are prepared from nitro groups by catalytic (Pd/C, $H_2$ or Raney Nickel, $H_2$) or chemical means ($CoCl_2$, $NaBH_4$). Alkylation of amines to give secondary and tertiary amines is achieved by reductive alkylation (aldehyde, $NaCNBH_4$) or alkylation with an alkyl group substituted with a leaving group in the presence of a base such as $K_2CO_3$. Tertiary amines may, alternatively, be carried through the reaction sequence to the pyrroles. Acylation of primary or secondary amines with activated acids, chloroformates, isocyanates and chlorosulfonates will give rise to amides, carbamates, ureas and sulfonamides, respectively.

Other methods of preparing amides and ureas are useful; such as for example, treatment of the amine with phosgene, or an equivalent thereof, followed by acylation of an alcohol or amine with the intermediate activated chloroformamide.

Carboxylic acids are best introduced as esters early in the synthesis. Saponification will provide carboxylic acids. Transesterification or esterification of the acids will give esters. Carboxylic acids may be converted to amides by activation and reaction with amines. Phenols are best introduced in a protected form early in the synthetic sequence to the pyrrole. Removal of the protecting group provides a phenol which may subsequently be alkylated in the presence of an alkylating agent and base to give an ether, or acylated with an isocyanate to give carbamates. Phenols may be converted to aryl ethers by reaction with an aryl bismethane in the presence of copper II acetate.

Aryl and heteroaryl groups may be attached to pyrrole pendant aryl and heteroaryl groups by application of coupling chemistry technology as outlined above.

The sequence and conditions of the reaction steps is dependent on the structure and functional groups present. Protecting groups may be necessary and may be chosen with reference to Greene, T. W., et al., *Protective Groups in Organic Synthesis*, John Wiley & Sons, Inc., 1991. The blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable hydroxyl protecting groups are: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl, and allyloxycarbonyl. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethoylsilyl, t-butldiphenylsilyl, 2-(trimethylsilyl)ethyl, phenacyl, p-methoxybenzyl, acetonyl, p-methoxyphenyl, 4-pyridylmethyl and t-butyl.

The following examples are illustrative and are not limiting of the compounds of this invention.

PREPARATIVE EXAMPLE 1

4-Fluoro-2-(4-pyridyl)acetophenone (1)

To a solution of lithium diisopropylamide (Aldrich Chemical Co. 2.0M in heptane, THF and ethylbenzene) 3.1 mL (6.3 mmol) in 6 mL of anhydrous THF at −78° C. under nitrogen was added 0.5 g (5.3 mmol) of 4-picoline dropwise. The reaction mixture was stirred for 20 minutes and then treated with a solution of 0.9 g (5.3 mmol) of 4-fluoro-(N-methyl-N-methoxy)-benzamide in THF. The reaction mixture was warmed to 0° C. and quenched by addition of 10 mL of brine. The mixture was extracted with ethyl acetate (3×10 mL) and the combined organic phases were dried over MgSO$_4$. The mixture was filtered and the filtrate was concentrated in vacuo to give an orange solid (4-Fluoro-2-(4-pyridyl) acetophenone). H$^1$ NMR (CDCl$_3$ 300 MHz): 4.23 s (d, 2H), 7.1–7.18 m (4H), 8.02 (dd, 2H), 8.55 (dd, 2H).

PREPARATIVE EXAMPLE 2

4-Fluoro-2-(2-pyridyl)acetophenone (2)

To a solution of lithium diisopropylamide (Aldrich Chemical Co. 2.0M in heptane,THF ethylbenzene) 5.2 mL (10.5 mmol) in 6 mL of anhydrous THF at −78° C. under nitrogen was added 0.93 g (10 mmol) of 2-picoline dropwise. The reaction mixture was stirred for 20 minutes and then treated with a solution of 1.71 g (5.3 mmol) of 4-fluoro-(N-methyl-N-methoxy)-benzamide in THF. The reaction mixture was warmed to 0° C. and quenched by addition of 10 mL of brine. The mixture was extracted with ethyl acetate (3×10 mL) and the combined organic phases were dried over MgSO$_4$. The mixture was filtered and the filtrate was concentrated in vacuo to give a solid. H$^1$ NMR (CDCl$_3$ 300 MHz): 4.49 (s); 6.0 (s); 6.97 (m); 7.-3-7.12 (m); 7.62 (m); 7.82 (m); 8.10 (dd); 8.28 (bd); 8.57 (bd). The compound exists in a keto/enol equilibrium as determined by H$^1$-NMR. FAB ms:216 (M$^+$+1).

PREPARATIVE EXAMPLES 3–10

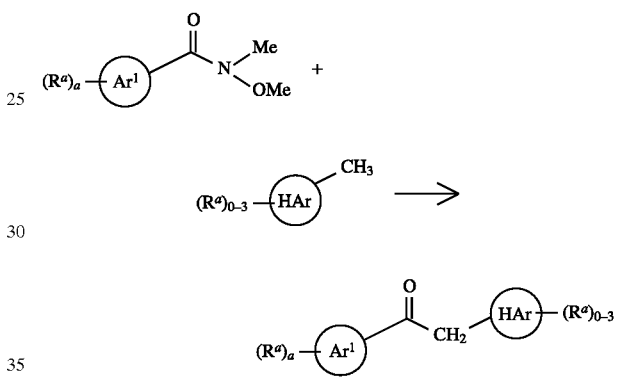

The following compounds are prepared in the manner described above:

TABLE I

| Prep Ex # | (R$^a$)$_a$—Ar$^1$ | HAr$^2$—(R$^a$)$_{0-3}$ |
|---|---|---|
| 3 | phenyl | 4-pyridyl |
| 4 | phenyl-4-F | 4-(3-methyl)-pyridyl |
| 5 | phenyl-4-F | 4-quinolinyl |
| 6 | phenyl-3-Cl | 4-pyridyl |
| 7 | phenyl-2-Cl | 4-pyridyl |
| 8 | phenyl-4-F | 4-pyrimidinyl |
| 9 | phenyl-4-F | 4-(2-Me)-pyridyl |
| 10 | phenyl-3,4-di-F | 4-pyridyl |

Purified by chromatography from the side product formed from alkylation of the 2-methyl group of 2,4-dimethylpyridine.

PREPARATIVE EXAMPLE 11 (Method 1)

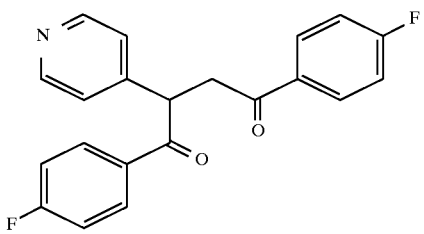

PREPARATIVE EXAMPLE 12 (Method 2)

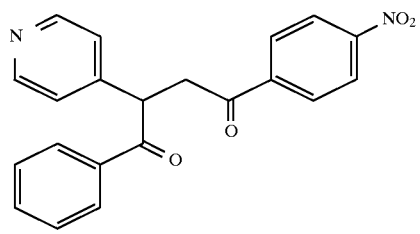

To a solution of 0.14 g (0.67 mmol) of 4-fluoro-2-(4-pyridyl)acetophenone (1) from Preparative Example 1 in 2 mL of anhydrous DMSO under nitrogen at room temperature was added 0.67 mL of a 1.0M solution of sodium hexamethyl disilazide in THF. After 15 minutes a solution of 4-fluoro-bromoacetophenone 0.14 g (0.67 mmol) in DMSO was added dropwise. The reaction mixture was diluted with 5 mL of water after 30 minutes and extracted with ethyl acetate (3×10 mL). The combined organic extracts were washed with brine and dried over $MgSO_4$. The mixture was filtered and the filtrate was concentrated in vacuo to give an oil. $H^1$ NMR ($CDCl_3$ 300 MHz): 3.26 (dd, 1H); 4.12 (dd, 1H); 5.23 (dd, 1H); 7.04–7.13 (m, 4H); 7.27 (dd, 2H); 7.95–8.05 (m, 4H); 8.51 (d, 2H).

0.2 g (1.02 mM) of the product of Preparative Example 3 in 3 mL of dry DMF under nitrogen was treated with 48.7 mg of 60% sodium hydride dispersion in oil. The reaction mixture was stirred at room temperature for one hour. 298 mg (1.22 mM) of 2-bromo-4'-nitroacetophenone dissolved in 1 mL of DMF was added dropwise. The reaction mixture was stirred at room temperature for 2 hours and was then treated with water and 10% citric acid solution. Ethyl acetate was added and the layers were separated and the aqueous phase was extracted with ethyl acetate. the organic phase was dried over $MgSO_4$, filtered and was concentrated in vacuo. The residue was purified by flash chromatography over silica gel eluting with 25–50% EtOAc/Hexanes to give the desired product.

PREPARATIVE EXAMPLES 13–37

The compounds of preparative examples 13–37 were prepared using starting materials from the preparative examples above.

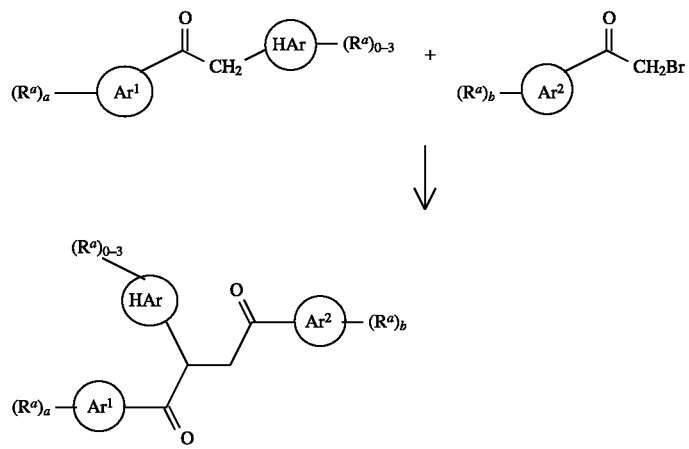

TABLE II

| Prep. Example # | $(R^a)_a$—Ar¹ | Ar²—$(R^a)_b$ | HAr²—$(R^a)_{0-3}$ | Method |
|---|---|---|---|---|
| 13 | Ph-4-F | Ph-4-OMe | 4-Pyridyl | 1 |
| 14 | Ph-4-F | Ph-2,5-di-OMe | 4-Pyridyl | 1 |

TABLE II-continued

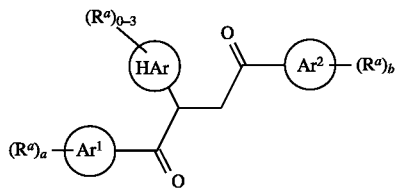

| Prep. Example # | (Rᵃ)ₐ—Ar¹ | Ar²—(Rᵃ)ᵦ | HAr²—(Rᵃ)₀₋₃ | Method |
|---|---|---|---|---|
| 15 | Ph-4-F | Ph-4-Br | 4-Pyridyl | 1 |
| 16 | Ph-4-F | Ph-4-Cl | 4-Pyridyl | 1 |
| 17 | Ph-4-F | Ph-4-SMe | 4-Pyridyl | 1 |
| 18 | Ph-4-F | Ph-4-OMe | 2-Pyridyl | 1 |
| 19 | Ph-4-F | Ph-4-Br | 2-Pyridyl | 1 |
| 20 | Ph-4-F | Ph-4-Cl | 2-Pyridyl | 1 |
| 21 | Ph-4-F | Ph-2,5-di-OMe | 2-Pyridyl | 1 |
| 22 | Ph | Ph-4-OMe | 4-Pyridyl | 1 |
| 23 | Ph | Ph-4-Cl | 4-Pyridyl | 1 |
| 24 | Ph | Ph-2,5-di-OMe | 4-Pyridyl | 1 |
| 25 | Ph | Ph-4-F | 4-Pyridyl | 1 |
| 26 | Ph | Ph-4-COOEt | 4-Pyridyl | 2 |
| 27 | Ph | Ph-2-F | 4-Pyridyl | 2 |
| 28 | Ph | Ph-3-NO₂ | 4-Pyridyl | 1 |
| 29 | Ph-4-F | Ph-4-SMe | 4-(3-Me)-pyridyl | 1 |
| 30 | Ph | Ph-3-F | 4-Pyridyl | 2 |
| 31 | Ph | Ph-2-NO₂ | 4-Pyridyl | 2 |
| 32 | Ph-4-F | Ph-4-SMe | 4-quinolinyl | 1 |
| 33 | Ph-2-Cl | Phenyl | 4-Pyridyl | 1 |
| 34 | Ph-3-Cl | Ph-4-SMe | 4-Pyridyl | 1 |
| 35 | Ph-4-F | Phenyl | 4-pyrimidinyl | 1 |
| 36 | Ph-4-F | Ph-4-SMe | 4-(2-Me)-pyridyl | 1 |
| 37 | Ph-3,4-F | Ph-4-SMe | 4-Pyridyl | 1 |

PREPARATIVE EXAMPLE 38

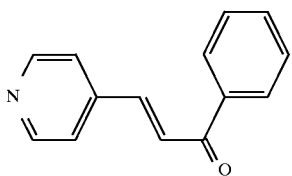

To 4.4 mL of dry pyridine under nitrogen was added 2.14 g (0.02 mol) of pyridine-4-carboxaldehyde followed by 2.4 g (0.02 mol) acetophenone and 1.46 g (0.02 mol) diethylamine. The solution was refluxed for 2.5 hours, cooled to room temperature and poured into 100 mL of ice water containing 10 mL of concentrated hydrochloric acid. The resulting solution was adjusted to pH 5.0 by addition of 1N NaOH solution while stirring rapidly. The mixture was filtered and the residue was washed with 15 mL of water. The solid was dried in vacuo to give the product.

$H^1$ NMR (CDCl₃ 300 MHz): 7.42–7.56 (m, 3H); 7.59–7.65 (m, 1H); 7.68 (d, 2H); 8.11 (dt, 2H); 8.69 (bd, 2H).

PREPARATIVE EXAMPLE 39

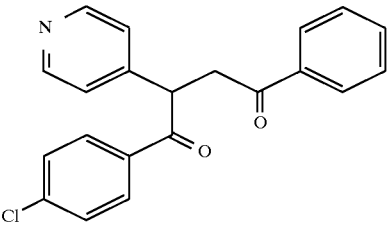

1-(4-chlorophenyl)-4-phenyl-2-(4-pyridyl)-butan-1,4-dione

To 0.019 g (0.039 mMol) of sodium cyanide in 2 ml of dry DMF at 30° C. was added a solution of 4-chlorobenzaldehyde in 1.5 mL of DMF over 20 minutes. A thick slurry formed. After 30 minutes a solution of the product of preparative example 38 in 1.5 mL of DMF was added dropwise. The mixture was agitated and stirred for 3 hours. The mixture was diluted with 30 ml of water and extracted with ethyl acetate (2×15 mL). The organic phase was washed with brine (1×15 mL) and dried over MgSO₄. The mixture was filtered and the filtrate was concentrated in vacuo to give the title compound as an oil.

PREPARATIVE EXAMPLE 40

4-phenyl-2-(4-pyridyl)-1-(4-trifluoromethylphenyl)-butan-1,4-dione

A solution of 0.15 g (0.71 mMol) of 1-phenyl-3-(4-pyridyl)-ethene-1-one (Preparative Example 38), 0.14 g (7.8 mMol) of 4-trifluoromethylbenzaldehyde, 0.035 g (0.35 mMol) of triethylamine and 20 mg (0.07 mMol) of 3,4-dimethyl-5-(2-hydroxyethyl)-thiazolium iodide in 3 mL on ethanol was heated at 80° C. for 3 hours. The reaction mixture was cooled to room temperature, diluted with 10 mL of water and was washed with water and brine and dried over MgSO$_4$. The mixture was filtered and the filtrate was concentrated in vacuo and the residue was purified by MPLC over silica gel eluting with 2.5% MeOH/CH$_2$Cl$_2$ to give the desired product.

H$^1$ NMR (CDCl$_3$ 300 MHz): 7.42–7.56 (m, 3H); 7.59–7.65 (m, 1H); 7.68 (d, 2H); 8.11 (dt, 2H); 8.69 (bd, 2H).

PREPARATIVE EXAMPLES 41–60

Following the procedure described above the following compounds are prepared:

TABLE III

| Prep Ex. # | (R$^a$)$_a$—Ar$^1$ |
|---|---|
| 41 | 4-methylthio-Ph |
| 42 | 4-Me—Ph |
| 43 | 4-t-BuO—Ph |
| 44 | 3,4-dichloro-Ph |
| 45 | 3,4-diberizyloxy-Ph |
| 46 | 2-thiophenyl |
| 47 | 3-furoyl |
| 48 | 3-Cl—Ph |
| 49 | 2-pyridyl |
| 50 | 4-CN—Ph |
| 51 | 4-methoxycarbonyl-Ph |
| 52 | 5-Me-2-thiophenyl |
| 53 | 3-Me-2-thiophenyl |
| 54 | 3-gumolinyl |
| 55 | 3-Pyridyl |
| 56 | 4-Pyridyl |
| 57 | 4-F-Ph |
| 58 | 2,4-di-F-Ph |
| 59 | 3-CN—Ph |
| 60 | 3,4-di-F-Ph |

PREPARATIVE EXAMPLE 61

To a 2 liter 3 neck flask equipped with a mechanical stirrer under N$_2$ was added 54.6 g (0.59 m) diisopropylethylamine and 150 mL of THF. The solution was cooled to –20° C. and treated with 268 ml (0.67 m) of 2.5M butyl lithium over 20 minutes. To the reaction mixture was added 125 g (0.56 mMol) of 4-(t-butyldimethysilyloxymethyl)pyridine in 100 ml of THF over 30 minutes. The reaction mixture was stirred for 1 hour at –15° and then treated with a solution of 108 g (0.59 mMol) of 4-fluoro-(N-methyl-N-methoxy)-benzamide dissolved in 100 mL of THF dropwise. The reaction was warmed to 0° C. and stirred for 1 hour and then was warmed to room temperature and was quenched by addition of 1 liter of 20% NH$_4$Cl solution. The aqueous phase was extracted with EtOAc (3×500 mL). The combined organic phases were washed with water (1×500 mL), 1×500 mL brine and were dried over MgSO$_4$. The mixture was filtered and the filtrate was concentrated in vacuo to give a dark oil. The product was purified by flash chromatography over silica gel eluting with 10–20% EtOAc/hexanes.

EXAMPLE 1

2-(4-fluorophenyl)-5-(4-fluorophenyl)-3-(4-pyridyl)-pyrrole

Method 1

To a solution of 0.35 g (0.99 mmol) of the compound of preparative example 11 in 15 mL of glacial acetic acid was added 0.35 g (4.7 mmol) ammonium acetate. The mixture was heated to 90°–110° C. over 10 hours at which time a further 1 g of ammonium acetate was added. Heating was continued at 110° C. for 6 hours. The reaction mixture was concentrated to 50% of the original volume, and 25 mL of water was gradually added. A solid formed, which was filtered and dried in vacuo to give the title compound. H$^1$ NMR (CDCl$_3$ 300 MHz): 6.61 (s, 1H); 6.98–7.05 (m, 4H); 7.20 (dd, 2H); 7.33 (dd, 2H); 7.53 (dd, 2H); 8.29 (d, 2H). FAB ms:333 (M$^+$+1).

Method 2

The condensation in method 1 is followed by an alternative work-up procedure. The reaction mixture was diluted with 5 mL of water and extracted with ethyl acetate (3×4 mL). The organic extracts are dried over MgSO$_4$, filtered and the filtrate concentrated in vacuo. The residue was purified by rotary chromatography to give the desired product.

EXAMPLES 2–43

0.15–0.2 g of the 1,4-diketone from Preparative Examples 13–37 and 39–60 is dissolved in 3 mL of acetic acid to which is added 1.0 g of ammonium acetate. The mixture is heated at 110° C. for 1.5–10 hours. The work-up of Method 1 or 2 is then utilized to isolate the compounds (Examples 2–50) listed below in Table IV.

TABLE IV

| Ex # | $(R^a)_a$—Ar$^1$ | Ar$^2$—$(R^a)_b$ | $(R^a)_{0-3}$—HAr | FAB ms |
|---|---|---|---|---|
| 2 | Ph-4-F | Ph-4-OMe | 4-Pyridyl | 345 |
| 3 | Ph-4-F | Ph-2,5-di-OMe | 4-Pyridyl | 375 |
| 4 | Ph-4-F | Ph-4-Br | 4-Pyridyl | 393/395 |
| 5 | Ph-4-F | Ph-4-Cl | 4-Pyridyl | 349 |
| 6 | Ph-4-F | Ph-4-OMe | 2-Pyridyl | 345 |
| 7 | Ph-4-F | Ph-4-Br | 2-Pyridyl | 393/395 |
| 8 | Ph-4-F | Ph-4-Cl | 2-Pyridyl | 349 |
| 9 | Ph-4-F | Ph-2,5-di-OMe | 2-Pyridyl | 375 |
| 10 | Ph | Ph-4-OMe | 4-Pyridyl | 327 |
| 11 | Ph | Ph-4-Cl | 4-Pyridyl | 331 |
| 12 | Ph | Ph-2,5-di-OMe | 4-Pyridyl | 357 |
| 13 | Ph | Ph-4-F | 4-Pyridyl | 315 |
| 14 | Ph-4-Cl | Ph | 4-Pyridyl | 331 |
| 15 | Ph-4-F | Ph-4-SMe | 4-Pyridyl | 361 |
| 16 | Ph-4-SMe | Ph | 4-Pyridyl | 325 |
| 17 | 4-CF3-Ph | Ph | 4-Pyridyl | 365 |
| 18 | 4-Me-Ph | Ph | 4-Pyridyl | 311 |
| 19 | 4-tBuO-Ph | Ph | 4-Pyridyl | 369 |
| 20 | 3,4-Cl-Ph | Ph | 4-Pyridyl | 366 |
| 21 | 3,4-di-(OBn)-Ph | Ph | 4-Pyridyl | 509 |
| 22 | 3-#-Ph | Ph | 4-pyridyl | 331 |
| 23 | 4-CN-Ph | Ph | 4-Pyridyl | 322 |
| 24 | 4-(COOMe)-Ph | Ph | 4-Pyridyl | 355 |
| 25 | Ph | 4-CO$_2$Et—Ph | 4-Pyridyl | 369 |
| 26 | Ph | 2-F-Ph | 4-Pyridyl | 315 |
| 27 | Ph | 3-NO$_2$—Ph | 4-Pyridyl | 342 |
| 28 | 5-Me-thiophen-2-yl | Ph | 4-Pyridyl | 317 |
| 29 | 3-Me-thiophen-2-yl | Ph | 4-Pyridyl | 317 |
| 30 | 4-F-Ph | 4-SMe—Ph | 4-(3-Me)-Pyridyl | 375 |
| 31 | Ph | 2-NO$_2$—Ph | 4-Pyridyl | 342 |
| 32 | Ph | 3-F-Ph | 4-Pyridyl | 315 |
| 33 | Ph | 4-NO$_2$—Ph | 4-Pyridyl | 342 |
| 34 | 4-F-Ph | Ph | 4-Pyridyl | 315 |
| 35 | 2,4-F-Ph | Ph | 4-Pyridyl | 333 |
| 36 | 3-CN-Ph | Ph | 4-Pyridyl | 322 |
| 37 | 3,4-F-Ph | Ph | 4-Pyridyl | 333 |
| 38 | 4-F-Ph | 4-(SMe)—Ph | 4-quinolinyl | 411 |
| 39 | 2-Cl—Ph | Ph | 4-pyridyl | 331 |
| 40 | 3-Cl—Ph | 4-(SMe)—Ph | 4-pyridyl | 377 |
| 41 | 4-F-Ph | Ph | 4-pyrimidinyl | 316 |
| 42 | 4-F-Ph | 4-(SMe)—Ph | 4-(2-methyl)-pyridyl | 375 |
| 43 | 3,4-4-F-Ph | 4-(SMe)—Ph | 4-pyridyl | 379 |

EXAMPLE 44

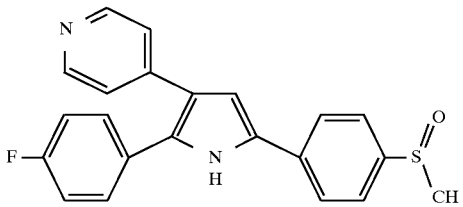

2-(4-fluorophenyl)-5-(4-methylsulfinylphenyl)-3-(4-pyridyl) pyrrole

To a solution of Example 15 (55.5 mg (0.15 mmol) in 2 ml of acetic acid and 1.4 ml of water was added potassium persulfate (50.0 mg (0.18 mmol). After stirring for 1.5 hours at room temperature the solution was neutralized by addition of ammonium hydroxide solution. The solid product was recovered by filtration and purified by flash chromatography eluting with 5% MeOH/CH$_2$Cl$_2$ to give the product. FAB ms: Calc.: 376 for C$_{22}$H$_{17}$N$_2$SOF; Obs.: 377 (M$^+$+1).

EXAMPLES 45–49

The following compounds are prepared using the procedures described above. An alternative work up was utilized wherein the reaction mixture was concentrated in vacuo and the residue was partitioned between ethyl acetate and water. The aqueous phase was extracted with ethyl acetate and the combined organic phases were dried over MgSO$_4$, filtered and purified by flash chromatography eluting with 5% MeOH/CH$_2$Cl$_2$ to give the product.

TABLE V

| Example # | Aryl$^1$ | Har | FAB ms |
|---|---|---|---|
| 45 | 4-F-phenyl | 4-(3-Me)-pyridyl | 391 |
| 46 | 4-F-phenyl | 4-guinolinyl | 427 |
| 47 | 3-Cl-phenyl | 4-pyridyl | 393 |
| 48 | 4-F-phenyl | 4-(2-Me)-pyridyl | 391 |
| 49 | 3,4-F-phenyl | 4-pyridyl | 395 |

EXAMPLE 50

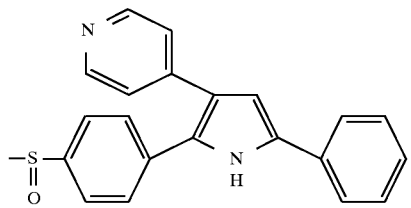

2-((4-methylsulfinylphenyl)-5-phenyl-3-(4-pyridyl) pyrrole

The title compound is prepared as in Example 44 using the product of Example 16 as the starting material. FAB ms: Calc.: 366 for C$_{23}$H$_{17}$N$_2$SO; Obs.: 367 (M$^+$+1).

EXAMPLE 51

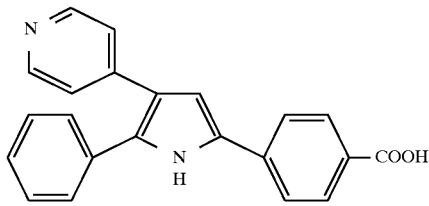

2-(phenyl)-5-(4-carboxyphenyl)-3-(4-pyridyl) pyrrole

To a solution of 25 mg (0.068 mmol) 2-phenyl-3-(4-pyridyl)-5-[(4-ethoxycarbonyl)phenyl]-1H-pyrrole (prepared according to Example 25) in 500 μL methanol and 500 μL THF was added 10 equivalents of a 5N NaOH solution. The reaction mixture was stirred at 60° C. for 16 hours. After the mixture was cooled to room temperature, volatiles were removed in vacuo. The residue was taken up in methanol and acidified to pH 2 using a 2N HCl solution. Volatiles were removed in vacuo. The residue was dissolved in a 1:1 mixture of THF/methanol and tritrated. The resulting mixture was centrifuged and filtered to remove sodium chloride. This process was repeated 3 times to ensure total removal of sodium chloride. Solvents were evaporated in vacuo to afford the desired product as a white glass, homogeneous by TLC (10% MeOH/CH$_2$Cl$_2$). FAB ms: Calc.: 340 for C$_{22}$H$_{16}$N$_2$O$_2$; Obs.: 341 (M$^+$+1).

EXAMPLE 52

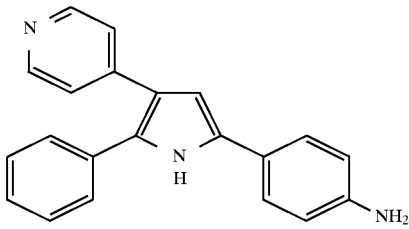

2-(phenyl)-5-(4-aminophenyl)-3-(4-pyridyl) pyrrole

To a suspension of 55 mg (0.161 mmol) 2-phenyl-3-(4-pyridyl)-5-[(4-nitro)phenyl]-1H-pyrrole (prepared according to Example 33) in 1.5 ml ethyl acetate and 1.5 ml ethanol was added 10 mg platinum (IV) oxide. The mixture was stirred under H$_2$ for 2 hours. The contents of flask were centrifuged, and the catalyst washed with ethyl acetate three times. The solvents were evaporated in vacuo to afford the desired product as a pale orange solid, homogeneous by TLC (5% MeOH/CH$_2$Cl$_2$). FAB ms: Calc.: 312 for C$_{21}$H$_{17}$N$_3$; Obs.: 313 (M$^+$+1).

EXAMPLE 53

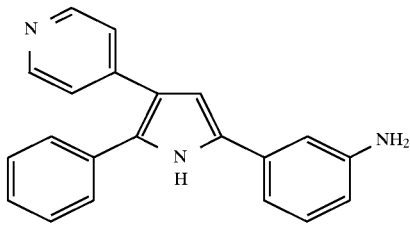

2-(phenyl)-5-(3-aminophenyl)-3-(4-pyridyl) pyrrole

The title compound is prepared as described above in Example 52 using the product of Example 27 as the starting material. FAB ms: Calc.: 312 for $C_{21}H_{17}N_3$; Obs.: 313 ($M^+$+1).

EXAMPLE 54

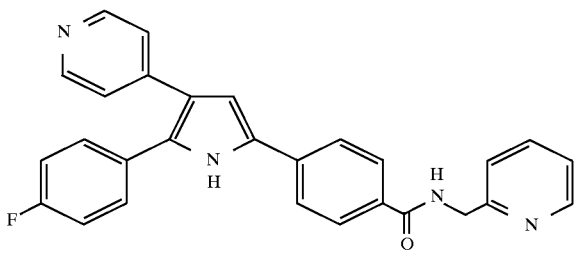

2-(4-fluorophenyl)-5-(4-(2-pyridylmethylaminocarbonyl)-phenyl)-3-(4-pyridyl)-pyrrole To a solution of 42 mg (0.124 mmol) 2-phenyl-3-(4-pyridyl)-5-[(4-carboxy)phenyl]-1H-pyrrole (prepared according to Example 51) in 800 uL DMF was added 1.5 equivalents BOP reagent (benzotriazol-1-yloxy-tris-(dimethylamino)phosphonium hexafluorophosphate), 1.2 equivalents 2-(aminomethyl)pyridine, and 2.5 equivalents triethylamine. The mixture was stirred at room temperature for 15 hours. The reaction was quenched by the addition of 5% $NaHCO_3$ solution and ethyl acetate (EtOAc). After separation of phases, the aqueous phase was re-extracted with EtOAc. The combined organic layers were washed with 5% $NaHCO_3$ solution, water, brine, and dried over $Na_2SO_4$. After filtration and concentration of the filtrate in vacuo, the crude product was flash chromatographed (gradient elution with 1.0%–5.0% $MeOH/CH_2Cl_2$) to the desired product as a cream-colored solid, homogeneous by TLC. FAB ms: Calc.: 430 for $C_{28}H_{22}N_4O$; Obs.: 431 ($M^+$+1).

EXAMPLES 55–63

This method is utilized to prepare the compounds listed below by coupling the appropriate amine to the acid derived from Example 51, or coupling an acid to the aniline formed in Example 52 or 53. The compounds are shown below in Table VI.

TABLE VI

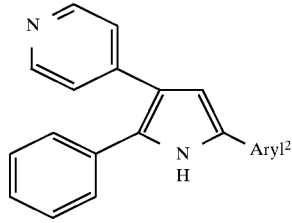

| Example # | Aryl² = | FAB ms |
|---|---|---|
| 55 | 4-(CONHCH₂-phenyl)-phenyl 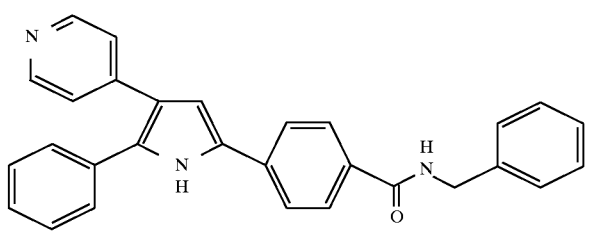 | 430 |

TABLE VI-continued
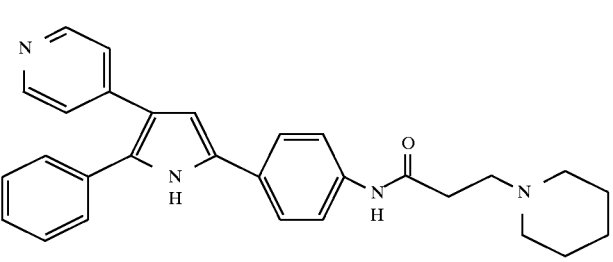
| Example # | Aryl² = | FAB ms |
|---|---|---|
| | 4-(NHCO(CH₂)₂-(1-piperidinyl))-phenyl | |
| 56 | 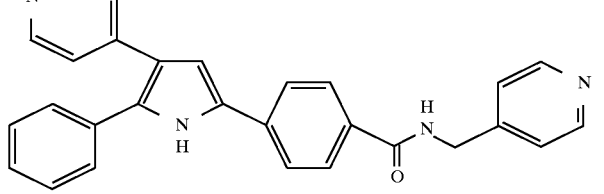 | 451 |
| | 4-(CONHCH₂-4-pyr)-phenyl | |
| 57 | 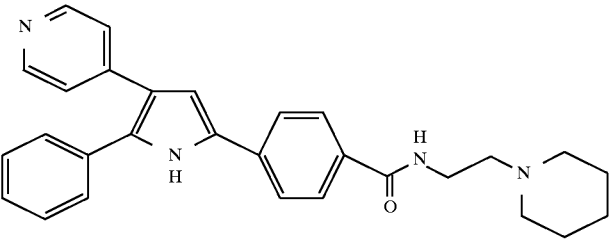 | 431 |
| | 4-(CONH(CH₂)₂-(1-piperidinyl))-phenyl | |
| 58 | 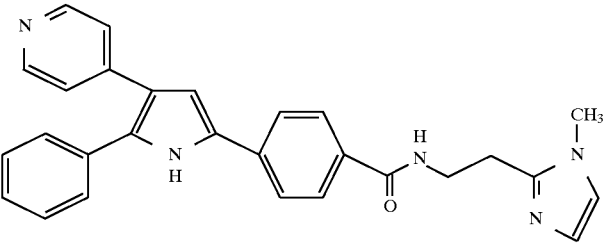 | 451 |
| | 4-(CONH(CH₂)₂-2-(N-methylimidazolyl)phenyl | |
| 59 | | 447 |

TABLE VI-continued

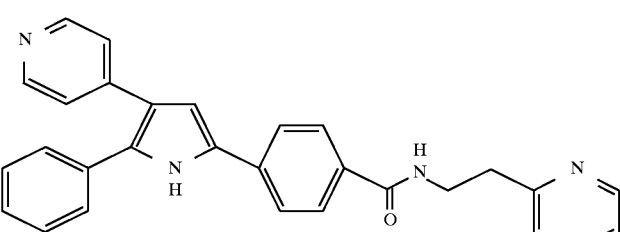

| Example # | Aryl² = | FAB ms |
|---|---|---|
| | 4-(CONH(CH₂)₂-(2-pyridyl))-phenyl | |
| 60 | 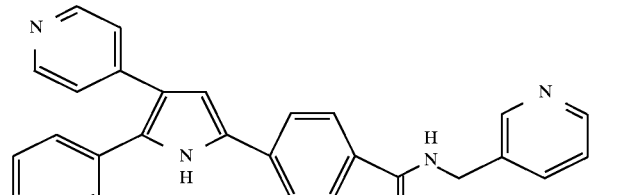 4-(CONHCH₂-(3-pyridyl))-phenyl | 445 |
| 61 | 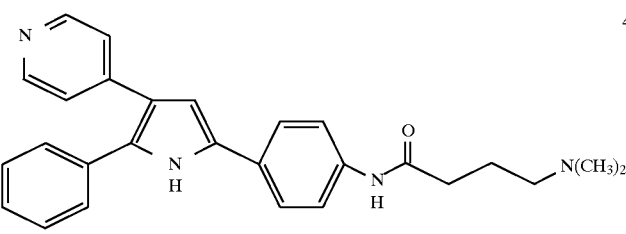 3-(NHCO(CH₂)₃-NMe₂)-phenyl | 431 |
| 62 | 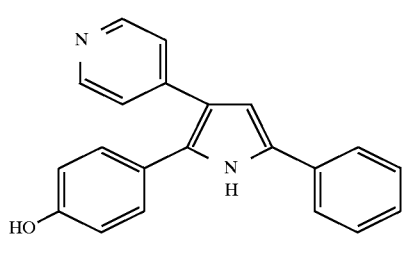 | 425 |

EXAMPLE 63

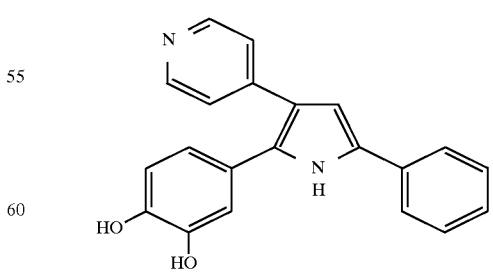

2-(4-hydroxyphenyl)-5-(phenyl)-3-(4-pyridyl) pyrrole 13.2 mg of the product of Example 19 was stirred for 2 hours in a mixture of 50% trifluoroacetic acid in methylene chloride. The reaction mixture was concentrated in vacuo to provide the desired product. FAB ms: Calc.: 312 for $C_{21}H_{16}N_2O$; Obs.: 313 (M⁺+1).

EXAMPLE 64

2-(3,4-dihydroxyphenyl)-5-(phenyl)-3-(4-pyridyl) pyrrole 20 mg of the product of Example 21 was dissolved in 1 mL of acetic acid and was hydrogenated at atmospheric pressure overnight in the presence of a catalytic amount of 10% Pd/C. The reaction mixture was concentrated in vacuo and the residue was purified by rotary chromatography over silica gel eluting with a gradient of 5 to 10% MeOH/CH$_2$Cl$_2$ to provide the desired product. FAB ms: Calc.: 328 for C$_{21}$H$_{16}$N$_2$O$_2$; Obs.: 329 (M$^+$+1).

EXAMPLE 65

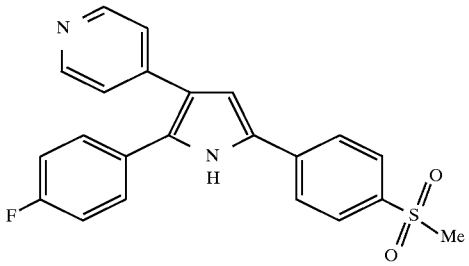

2-(4-fluorophenyl)-5-(4-methylsulfonylphenyl)-3-(4-pyridyl) pyrrole 0.5 g (1.4 mmol) of the product of Example 44 was dissolved in a mixture of 4 mL of methanol and 16 mL of ethyl acetate. The solution was treated 0.045 g sodium tungstate dihydrate and 0.63 mL (5.6 mmol) of 30% hydrogen peroxide solution while heating at reflux over a period of 4 hours. A further 0.3 mL (2.8 mmol) hydrogen peroxide was added. The mixture was refluxed overnight and then cooled to room temperature. A white solid was recovered by filtration and was washed with water to provide the desired product.

H$^1$-NMR (CDCl$_3$): 3.10 (s, 3H); 6.92 (d, 1H)Hz); 7.09 (t, 2H); 7.22 (m, 2H); 7.42 (dd, 2H); 7.72 (d, 2H); 7.95 (d, 2H); 8.45 (d, 2H), 8.95 (bs, 1H). FAB ms:Calc: 392 for C$_{22}$H$_{17}$N$_2$SO$_2$F; Obs.:393 (M$^+$+1).

EXAMPLE 66

2-(3-chlorophenyl)-5-(4-methylsulfonylphenyl)-3-(4-pyridyl) pyrrole

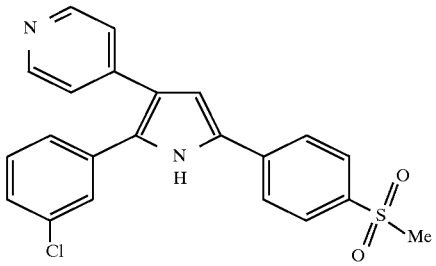

The product of Example 47 was converted to the desired sulfone as described in Example 65. A portion of the product may be isolated by filtration as described in Example 65. The balance of the product was recovered following washing of the reaction mixture with aqueous sodium sulfite, water and brine and drying over MgSO$_4$. The crude product was purified by crystallization from CH$_2$Cl$_2$/MeOH followed by recrystalization from isopropanol.

H$^1$-NMR (CD$_3$OD): 3.15 (s, 3H); 7.09 (d, 1H); 7.39 (m, 4H); 7.50 (s, 1H); 7.95 (s, 4H); 8.41 (d, 2H). FAB ms:Calc: 408 for C$_{22}$H$_{17}$N$_2$SO$_2$Cl1; Obs.:409 (M$^+$+1).

EXAMPLES 67–123

Using the procedures set forth above, the following compounds can be prepared, as set forth in Table VII.

TABLE VII

| Ex # | (R$^a$)$_a$—Ar$^1$ | Ar$^2$—(R$^a$)$_b$ | (R$^a$)$_{0-3}$—HAr | R$^2$ |
|---|---|---|---|---|
| 67 | Ph | Ph-4-F | 3-quinolinyl | H |
| 68 | Ph | Ph-4-F | 4-pyrimidinyl | H |
| 69 | Ph | Ph-4-F | 3-pyridazinyl | H |
| 70 | Ph | Ph-4-F | 2-pyrazinyl | H |
| 71 | Ph | Ph-4-CN | 4-pyridyl | H |
| 72 | Ph | Ph-2-OMe | 4-pyridyl | H |
| 73 | Ph | Ph-3-OMe | 4-pyridyl | H |
| 74 | Ph-3,4-di-F | Ph-4-S(O)-Me | 4-pyridyl | H |
| 75 | Ph | Ph-4-NMe$_2$ | 4-pyridyl | H |
| 76 | Ph | 4-(4-(N-COCH$_3$)piperazinyl)-Ph | 4-pyridyl | H |
| 77 | Ph | 4-(morpholinyl)-Ph | 4-pyridyl | H |
| 78 | Ph | Ph-2-Cl | 4-pyridyl | H |
| 79 | Ph | Ph-3-Cl | 4-pyridyl | H |
| 80 | Ph | Ph-4-CF$_3$ | 4-pyridyl | H |
| 81 | Ph | Ph-4-S-Me | 4-pyridyl | H |
| 82 | Ph | Ph-4-S(O)-Me | 4-pyridyl | H |
| 83 | Ph-4-F | (4-methyl)-2-thiophenyl | 4-pyridyl | H |
| 84 | Ph-4-F | (4-bromo)-2-thiophenyl | 4-pyridyl | H |
| 85 | Ph-4-F | Ph-4-F-3-Cl | 4-pyridyl | H |

TABLE VII-continued

| Ex # | (Rª)ₐ—Ar¹ | Ar²—(Rª)ᵦ | (Rª)₀₋₃—HAr | R² |
|---|---|---|---|---|
| 86 | Ph-4-F | 2-benzoxazolyl | 4-pyridyl | H |
| 87 | Ph-4-F | 2-benzofuranyl | 4-pyridyl | H |
| 88 | Ph-4-F | 4-(O(CH₂)₃NMe₂)-Ph | 4-pyridyl | H |
| 89 | Ph-4-F | 4-(O(CH₂)₂-piperidin-1-yl)-Ph | 4-pyridyl | H |
| 90 | Ph-4-Cl | Ph-4-F | 4-pyridyl | H |
| 91 | Ph-3-Cl | Ph-4-F | 4-pyridyl | H |
| 92 | Ph-2-Cl | Ph-4-F | 4-pyridyl | H |
| 93 | Ph-3,4-di-Cl | Ph-4-F | 4-pyridyl | H |
| 94 | Ph-3-CF₃ | Ph-4-F | 4-pyridyl | H |
| 95 | Ph-4-S-Me | Ph-4-F | 4-pyridyl | H |
| 96 | Ph-4-S(O)-Me | Ph-4-F | 4-pyridyl | H |
| 97 | Ph-2-OBn | Ph-4-F | 4-pyridyl | H |
| 98 | Ph-4-Br | Ph-4-F | 4-pyridyl | H |
| 99 | Ph-2-OMe | Ph-4-F | 4-pyridyl | H |
| 100 | Ph-3-OMe | Ph4-F | 4-pyridyl | H |
| 101 | Ph-4-OMe | Ph-4-F | 4-pyridyl | H |
| 102 | Ph-4-NO₂ | Ph-4-F | 4-pyridyl | H |
| 103 | Ph-4-NMe₂ | Ph-4-F | 4-pyridyl | H |
| 104 | Ph-4-(4-N-COCH₃)-piperazinyl | Ph-4-F | 4-pyridyl | H |
| 105 | Ph-4-morpholinyl | Ph-4-F | 4-pyridyl | H |
| 106 | 2-thiophenyl | Ph-4-F | 4-pyridyl | H |
| 107 | 3-thiophenyl | Ph-4-F | 4-pyridyl | H |
| 108 | 2-furoyl | Ph-4-F | 4-pyridyl | H |
| 109 | 3-furoyl | Ph-4-F | 4-pyridyl | H |
| 110 | Ph-3-Cl | Ph-4-S(O)Me | 4-(2-Me)-pyridyl | H |
| 111 | Ph-3,4-di-F | Ph-4-S(O)Me | 4-(2-Me)-pyridyl | H |
| 112 | Ph-3,4-di-F | Ph-4-S(O)Me | 4-pyridyl | F |
| 113 | Ph-3-CF₃ | Ph | 4-pyridyl | H |
| 114 | Ph-4-F | Ph-4-S(O)Me | 4-(2-aminobenzyl)pyridyl | H |
| 115 | 3-quinolinyl | Ph | 4-pyridyl | H |
| 116 | Ph-4-F | 4-(SMe)-Ph | 4-pyridyl | Br |
| 117 | Ph-3,4-di-F | Ph | 4-pyridyl | CO₂Et |
| 118 | Ph-3,4-di-F | Ph | 4-pyridyl | CN |
| 119 | 3-(CF₃)-Ph | Ph | 4-pyridyl | CO₂Et |
| 120 | 3-(CF₃)-Ph | Ph | 4-pyridyl | CN |
| 121 | Ph | Ph-4-F | 3-methyl-4-pyridyl | H |
| 122 | Ph-3-Cl | Ph-4-S(O)Me | 4-(2-amino)pyrimidinyl | H |
| 123 | Ph | Ph-4-F | 3,5-dimethyl-4-pyridyl | H |

Bn = benzyl,
Ph = phenyl,
Me = methyl
Et = ethyl

EXAMPLE 124

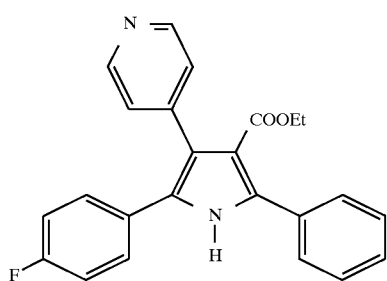

A mixture of ethyl 2-benzoyl-acetate (0.41 g (2.0 mmol), 0.5 g (1.44 mmol) of the product of Preparative Example 61 and 0.61 g (8 mmol) of ammonium acetate were heated in acetic acid at reflux until the benzoin was consumed. The reaction mixture was diluted with ethyl acetate and washed with water and brine and dried over MgSO₄. The mixture was filtered and the filtrate was concentrated in vacuo and the residue was purified by chromatography over silica gel to give the desired product. H¹-NMR (CDCl₃, 300 MHz): 0.92 (t, 3H); 4.01 (q, 2H); 6.94 (t, 2H); 7.12 (m, 4H); 7.41 (m, 4H); 7.61 (m, 2H); 8.10 (m, 1H); 9.20 (bs, 1H). FAB ms:C24H19N2O2F=386; Observed:387 (M⁺=1).

EXAMPLE 125

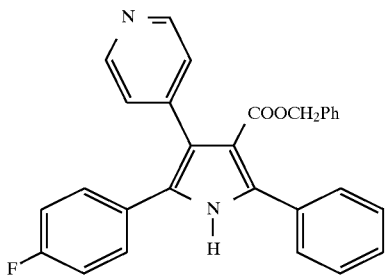

A mixture of benzyl 2-benzoyl-acetate (2.0 mmol), 0.5 g (1.44 mmol) of the product of Preparative Example 61 and 0.61 g (8 mmol) of ammonium acetate heated in acetic acid at reflux will provide the title compound after purification as recited in Example 124.

EXAMPLE 126

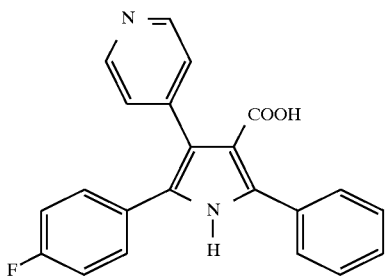

A mixture of benzyl 2-(4-fluorophenyl)-3-(4-pyridyl)-5-phenyl-pyrrole-4-carboxylate from Example 125 (1.0 mmol), 0.01 g of 10% Pd/C in 5 mL of EtOH will yield 2-(4-fluorophenyl)-3-(4-pyridyl)-5-phenyl-pyrrole-4-carboxylic acid after treatment with 40 psi $H_2$ followed by filtration.

EXAMPLE 127

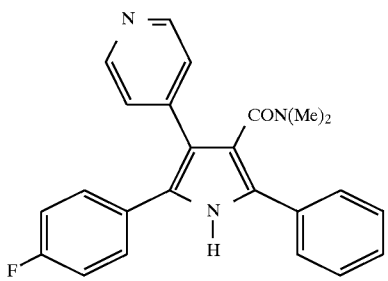

A mixture of 2-(4-fluorophenyl)-3-(4-pyridyl)-5-phenyl-pyrrole-4-carboxylic acid from Example 126 (1.0 mmol), EDC, Hunig's base and dimethylamine hydrochloride in DMF is stirred at room temperature overnight. The reaction mixture is diluted with water, adjusted to pH 7.0 and extracted with ethyl acetate. The organic extracts are washed with brine, dried over $MgSO_4$, filtered and concentrated in vacuo. The residue is purified by chromatography.

EXAMPLE 128

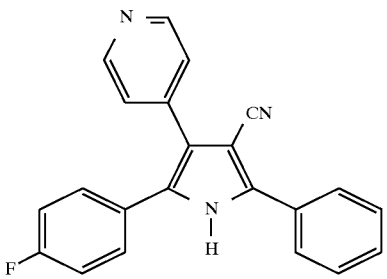

A mixture of benzoylacetonitrile 0.5 g (3.4 mmol), 1.17 g (3.4 mmol) of the product of Preparative Example 61 and 1.0 g (13.6 mmol) ammonium acetate are heated in acetic acid at reflux until the benzoin is consumed. The reaction mixture was diluted with ethyl acetate and washed with water and brine and dried over $MgSO_4$. The mixture is filtered and the filtrate is concentrated in vacuo. The residue is purified by chromatography over silica gel eluting with 5% MeOH/$CH_2Cl_2$ to give the desired product.

$H^1$-NMR (CDCl$_3$, 300 MHz): 7.0 (t, 2H); 7.24 (m, 2H); 7.32–7.48 (m, 5H); 7.74 (bd, 2H); 8.42 (bs, 1H). FAB ms:$C_{22}H_{14}N_3F$=339; Observed: 340 (M$^+$=1).

EXAMPLE 129

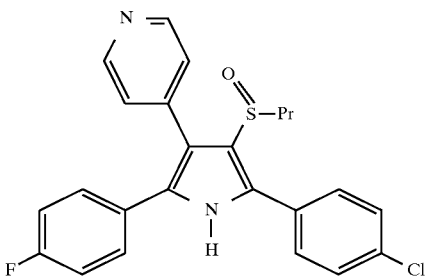

The product of Example 5 is dissolved in methylene chloride and treated with 1.05 equivalents of n-propylsulfinyl chloride at 0° C. under nitrogen. After 30 minutes triethylamine is added to neutralize the reaction mixture. The reaction mixture is diluted with ethyl acetate and washed with water and brine and dried over $MgSO_4$. The mixture is filtered and the filtrate is concentrated in vacuo. The residue is purified by chromatography over silica gel to give the desired product.

EXAMPLE 130

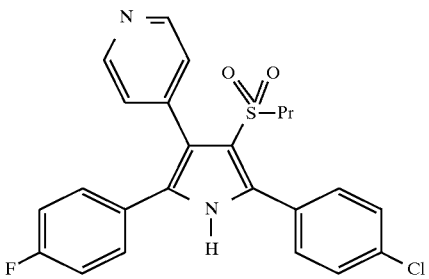

The product of Example 129 is reacted with 1.05 equivalents of meta-chloroperoxybenzoic acid in $CH_2Cl_2$ at 0° C.

The reaction mixture is stirred overnight at room temperature. The solution is diluted with EtOAc and washed with saturated sodium bicarbonate solution followed by brine. The solution is dried over MgSO$_4$, filtered and concentrated in vacuo. The residue is purified by silica gel chromatography to produce the desired product.

EXAMPLE 131

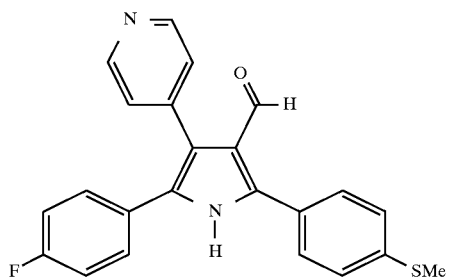

To 5 ml of DMF at room temperature under nitrogen is added 0.3 g (2 mmol) of POCl$_3$ dropwise. After 15 minutes a solution of 0.37 g (0.86 mmol) of the product of Example 15 is added dropwise. The solution was warmed at 60° C. until the starting material had been consumed. The reaction mixture was cooled to room temperature and then poured into ice water (20 ml). The mixture was made basic by addition of saturated sodium carbonate solution and then stirred in the presence of 20 ml of chloroform. The chloroform phase was separated and the aqueous phase was extracted with chloroform (2×10 ml). The combined organic phase is washed with water and brine and dried over MgSO$_4$. The mixture is filtered and the filtrate is concentrated in vacuo; the residue is purified by chromatography over silica gel to give the desired product.

EXAMPLE 132

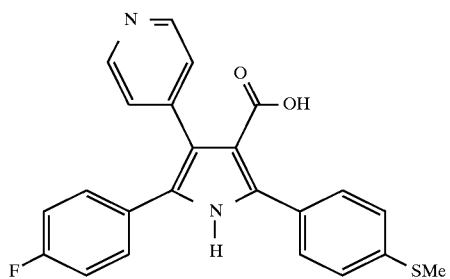

The product of Example 131 is dissolved in t-butyl alcohol and methyl-2-butene (6:1 ratio). The solution is then treated with 1.5 eq of monobasic sodium phosphate and an aqueous solution of sodium chlorate. The reaction mixture is stirred at room temperature until the starting material is consumed. The pH is adjusted to 5.5 with dilute HCl. The product is extracted with ethyl acetate and the combined organic phase is washed with water and brine, and dried over MgSO$_4$. The mixture is filtered and the filtrate is concentrated in vacuo to give the desired product.

EXAMPLE 133

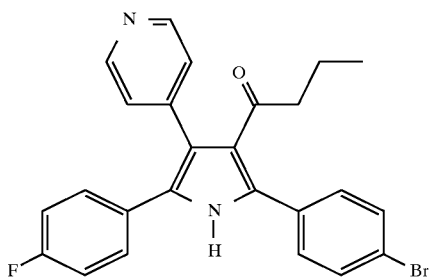

To 5 ml of N,N-dimethylbutyramide at room temperature under nitrogen is added 0.3 g (2 mmol) of POCl$_3$ dropwise. After 15 minutes, a solution of 0.37 g (0.86 mmol) of the product of Example 4 is added dropwise. The solution is warmed at 60° C. until the starting material is consumed. The reaction mixture is cooled to room temperature and then poured into ice water (20 ml). The mixture is made basic by addition of saturated sodium carbonate solution and then stirred in the presence of 20 mL of chloroform. The chloroform phase is separated and the aqueous phase extracted with chloroform (2×10 ml). The combined organic phase is washed with water and brine and dried over MgSO$_4$. The mixture is filtered and the filtrate is concentrated in vacuo. The residue is purified by chromatography over silica gel to give the desired product.

EXAMPLES 134–203

Using the procedures set forth above, the compounds shown in Table VIII can be prepared.

TABLE VIII

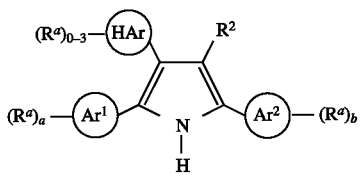

| Ex. | (R$^a$)$_a$—(Ar$^1$) | (Ar$^2$)—(R$^a$)$_b$ | (R$^a$)$_{0-3}$—(HAr) | R$^2$ |
|---|---|---|---|---|
| 134 | Ph-4-F | Ph-4-OMe | 4-pyridyl | C(O)Me |
| 135 | Ph-4-F | Ph-2,5-di-OMe | 4-pyridyl | C(O)Me |

TABLE VIII-continued

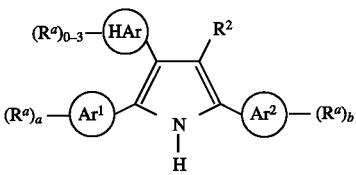

| Ex. | (R$^a$)$_a$—Ar$^1$ | Ar$^2$—(R$^a$)$_b$ | (R$^a$)$_{0-3}$—HAr | R$^2$ |
|---|---|---|---|---|
| 136 | Ph-4-F | Ph-4-Br | 4-pyridyl | C(O)Propyl |
| 137 | Ph-4-F | Ph-4-Cl | 4-pyridyl | C(O)Ethyl |
| 138 | Ph-4-F | Ph-4-OMe | 2-pyridyl | C(O)Me |
| 139 | Ph-4-F | Ph-4-Br | 2-pyridyl | C(O)Me |
| 140 | Ph-4-F | Ph-2,5-di-OMe | 2-pyridyl | C(O)Me |
| 141 | Ph | Ph-4-OMe | 4-pyridyl | C(O)Me |
| 142 | Ph | Ph-4-Cl | 4-pyridyl | C(O)Me |
| 143 | Ph | Ph-2,5-di-OMe | 4-pyridyl | C(O)Me |
| 144 | Ph | Ph-4-F | 4-pyridyl | C(O)Me |
| 145 | Ph-4-Cl | Ph | 4-pyridyl | C(O)Me |
| 146 | Ph-4-F | Ph-4-SMe | 4-pyridyl | C(O)Me |
| 147 | Ph-4-SMe | Ph | 3-methyl-4-pyridyl | C(O)Me |
| 148 | Ph-4-F | Ph-4-SMe | 3-methyl-4-pyridyl | CN |
| 149 | Ph-4-F | Ph-4-S(O)Me | 3-methyl-4-pyridyl | CN |
| 150 | Ph-3-Cl | Ph-4-Cl | 4-quinolyl | CN |
| 151 | Ph-4-F | Ph-4-Cl | 2-methyl-4-pyridyl | CN |
| 152 | Ph | Ph-4-F | 3,5-dimethyl-4-pyridyl | CN |
| 153 | Ph | Ph-4-F | 3-quinolinyl | CN |
| 154 | Ph | Ph-4-F | 4-quinolinyl | CN |
| 155 | Ph | Ph-4-F | 2-quinolinyl | CN |
| 156 | Ph | Ph-4-F | 2-pyrimidinyl | CN |
| 157 | Ph | Ph-4-F | 4-pyrimidinyl | CN |
| 158 | Ph | Ph-4-F | 3-pyridazinyl | CN |
| 159 | Ph | Ph-4-F | 2-pyrazinyl | CN |
| 160 | Ph | Ph-4-F | 2-pyrimidinyl | CN |
| 161 | Ph | Ph-4-F | 4-pyrimidinyl | CN |
| 162 | Ph | Ph-4-F | 2-imidazo-(4,5-b)-pyridinyl | CN |
| 163 | Ph | Ph-4-F | 7-imidazo-(4,3-b)-pyridinyl | CN |
| 164 | Ph | Ph-4-F | 4-pyridyl | COMe |
| 165 | Ph | Ph-4-F | 4-pyridyl | SO$_2$Me |
| 166 | Ph | Ph-4-CN | 4-pyridyl | COMe |
| 167 | Ph | Ph-2-OMe | 4-pyridyl | COMe |
| 168 | Ph | Ph-3-OMe | 4-pyridyl | CN |
| 169 | Ph | Ph-4-OMe | 4-pyridyl | CO$_2$Et |
| 170 | Ph | Ph-4-NO$_2$ | 4-pyridyl | CN |
| 171 | Ph | Ph-4-NMe$_2$ | 4-pyridyl | CN |
| 172 | Ph | 4-(4-(N-COCH$_3$)-piperazinyl)-Ph | 4-pyridyl | CN |
| 173 | Ph | 4-(morpholinyl)-Ph | 4-pyridyl | CN |
| 174 | Ph | Ph-2-Cl | 4-pyridyl | CN |
| 175 | Ph | Ph-3-Cl | 4-pyridyl | C(O)Me |
| 176 | Ph | Ph-4-CF$_3$ | 4-pyridyl | SO$_2$Me |
| 177 | Ph | Ph-4-S-Me | 4-pyridyl | CN |
| 178 | Ph | Ph-4-S(O)-Me | 4-pyridyl | CN |
| 179 | Ph-4-F | (4-methyl)thiopen-2yl | 4-pyridyl | CN |
| 180 | Ph-4-F | (3-methyl)thiophen-2yl | 4-pyridyl | C(O)Me |
| 181 | Ph-4-F | (4-bromo)thiophen-2yl | 4-pyridyl | SO$_2$Me |
| 182 | Ph-4-F | (5-methyl)thiophen-2yl | 4-pyridyl | CN |
| 183 | Ph-4-F | Ph-4-F-3-Cl | 4-pyridyl | CN |
| 184 | Ph-4-F | 2-benzoxazolyl | 4-pyridyl | CN |
| 185 | Ph-4-F | 2-benzofuranyl | 4-pyridyl | CN |
| 186 | Ph-4-F | 4-(O(CH$_2$)$_3$NMe$_2$)-Ph | 4-pyridyl | CN |
| 187 | Ph-4-F | 4-(O(CH$_2$)$_2$N-piperidinyl)-Ph | 4-pyridyl | CN |
| 188 | Ph-4-Cl | Ph-4-F | 4-pyridyl | CN |
| 189 | Ph-3-Cl | Ph-4-F | 4-pyridyl | CN |
| 190 | Ph-2-Cl | Ph-4-F | 4-pyridyl | CN |
| 191 | Ph-3,4-di-Cl | Ph-4-F | 4-pyridyl | CN |
| 192 | Ph-3-CF$_3$ | Ph-4-F | 4-pyridyl | CN |
| 193 | Ph-4-S-Me | Ph-4-F | 4-pyridyl | CN |
| 194 | Ph-4-S(O)-Me | Ph-4-F | 4-pyridyl | CN |
| 195 | Ph-2-OBn | Ph-4-F | 4-pyridyl | CN |
| 196 | Ph-4-Br | Ph-4-F | 4-pyridyl | CN |
| 197 | Ph-2-OMe | Ph-4-F | 4-pyridyl | CN |
| 198 | Ph-3-OMe | Ph-4-F | 4-pyridyl | CN |
| 199 | Ph-4-OMe | Ph-4-F | 4-pyridyl | CN |
| 200 | Ph-4-NO$_2$ | Ph-4-F | 4-pyridyl | CN |
| 201 | Ph-4-NMe$_2$ | Ph-4-F | 4-pyridyl | CN |

TABLE VIII-continued

| Ex. | $(R^a)_a$—Ar¹ | Ar²—$(R^a)_b$ | $(R^a)_{0-3}$—HAr | R² |
|---|---|---|---|---|
| 202 | 4-(4-(N-COCH₃)-piperazinyl-Ph | Ph-4-F | 4-pyridyl | CN |
| 203 | 4-(morpholinyl)-Ph | Ph-4-F | 4-pyridyl | CN |

Me = methyl,
Et = ethyl,
Ph = phenyl,
Bn = benzyl,

BIOLOGICAL ASSAYS

The ability of compounds of the present invention to inhibit cytokines can be demonstrated by the following in vitro assays.

Lipopolysaccharide mediated production of cytokines

Human peripheral blood mononuclear cells (PBMC) are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2\times10^6$ cell/mL in RPMI (cell culture medium) containing 10% fresh autologous human serum, penicillin streptomycin (10 U/mL) and 0.05% DMSO. Lipopolysaccharide (Salmonella type Re545; Sigma Chemicals) is added to the cells to a final concentration of 100 ng/mL. An aliquot (0.1 mL) of the cells is quickly dispensed into each well of a 96 well plate containing 0.1 mL of the test compound, at the appropriate dilution, and incubated for 24 hours. at 37° C. in 5% $CO_2$. At the end of the culture period, cell culture supernatants are assayed for IL-1β, TNF-α, IL-6 and $PGE_2$ production using specific ELISA.

IL-1 mediated cytokine production

Human peripheral blood mononuclear cells are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2\times10^6$ cell/mL in RPMI containing 10% fresh autologous human serum, penicillin streptomycin (10 U/mL) and 0.05% DMSO. Endotoxin free recombinant human IL-1β is then added to a final concentration of 50 pMolar. An aliquot (0.1 mL) of the cells is quickly dispensed into each well of a 96 well plate containing 0.1 mL of the compound at the appropriate dilution. and are incubated for 24 hours at 37° C. in 5% $CO_2$. At the end of the culture period, cell culture supernatants are assayed for TNF-α, IL-6 and $PGE_2$ synthesis using specific ELISA.

Determination of IL-1β, TNF-α, IL-6 and prostanoid production from LPS or IL-1 stimulated PBMC's

IL-1β ELISA

Human IL-1β can be detected in cell-culture supernatants or whole blood with the following specific trapping ELISA. Ninety-six well plastic plates (Immulon 4; Dynatech) are coated for 12 hours at 4° C. with 1 mg/mL protein-A affinity chromatography purified mouse anti-human IL-1b monoclonal antibody (purchased as an ascites preparation from LAO Enterprise, Gaithersburg Md.) diluted in Dulbecco's phosphate-buffered saline (—$MgCl_2$, —$CaCl_2$). The plates are washed with PBS (phosphate buffered saline)-Tween (Kirkegaard and Perry) then blocked with 1% BSA diluent and blocking solution (Kirkegaard and Perry) for 60 minutes at room temperature followed by washing with PBS Tween.

IL-1β standards are prepared from purified recombinant IL-1β produced from *E. coli*. The highest concentration begins at 10 ng/mL followed by 11 two-fold serial dilutions. For detection of IL-1β from cell culture supernatants or blood plasma, 10–25 mL of supernatant is added to each test well with 75–90 mL of PBS Tween. Samples are incubated at room temperature for 2 hours then washed 6 times with PBS Tween on an automated plate washer (Dennly). Rabbit anti-human IL-1β polyclonal antisera diluted 1:500 in PBS-Tween is added to the plate and incubated for 1 hour at room temperature followed by six washes with PBS-Tween. Detection of bound rabbit anti-IL-1β IgG is accomplished with Fab' fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color intensity on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-α ELISA

Immulon 4 (Dynatech) 96-well plastic plates are coated with a 0.5 mg/mL solution of mouse anti-human TNF-α monoclonal antibody. The secondary antibody is a 1:2500 dilution of a rabbit anti-human TNF-α polyclonal serum purchased from Genzyme. All other operations are identical to those described above for IL-1b. The standards are prepared in PBS-Tween+10% FBS (fetal bovine serum) or HS (human serum). Eleven 2 fold dilutions are made beginning at 20 ng/mL TNF-α.

IL-6 ELISA

Levels of secreted human IL-6 are also determined by specific trapping ELISA as described previously in Chin and Kostura, *J. Immunol.* 151, 5574–5585 (1993). (Dynatech) ELISA plates are coated with mouse anti-human IL-6 monoclonal antibody diluted to 0.5 mg/ml in PBS. The secondary antibody, a rabbit anti-human IL-6 polyclonal antiserum, is diluted 1:5000 with PBS-Tween. All other operations are identical to those described above for IL-1β. The standards are prepared in PBS-Tween+10% FBS or HS. Eleven 2 fold dilutions are made beginning at 50 ng/mL IL-6.

$PGE_2$ Production

Prostaglandin $E_2$ is detected in cell culture supernatants from LPS or IL-1 stimulated PBMC's using a commercially available enzyme immunoassay. The assay purchased from the Cayman Chemical (Catalogue number 514010) and is run exactly according to the manufacturers instructions.

Interleukin8 (IL-8)

The present compounds can also be assayed for IL-8 inhibitory activity as discussed below. Primary human umbilical cord endothelial cells (HUVEC) (Cell Systems, Kirland, Wash.) are maintained in culture medium supplemented with 15% fetal bovine serum (FBS) and 1% CS-HBGF (cell culture additive) consisting of aFGF (acid fibroblast growth factor) and heparin. The cells are then diluted 20-fold before being plated (250 μl) into gelatin coated 96-well plates. Prior to use, culture medium is replaced with fresh medium (200 μl). Buffer or test compound (25 μl, at appropriate concentrations) is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/ml) of multiple samples based on the standard curve. $IC_{50}$ values where appropriate are generated by non-linear regression analysis.

The following compounds are found to inhibit cytokines at $IC_{50}$ concentrations of less than 100 μM.

TABLE IX

| $R^1$ | $(R^a)_a$—Ar$^1$ | Ar$^2$—$(R^a)_b$ | $(R^a)_{0-3}$—HAr | $R^2$ |
|---|---|---|---|---|
| H | 4-F-Ph | 4-F-Ph | 4-Pyr | H |
| H | 4-F-Ph | 4-OMe—Ph | 4-Pyr | H |
| H | 4-F-Ph | 2,5-di-(OMe)—Ph | 4-Pyr | H |
| H | 4-F-Ph | 4-Br—Ph | 4-Pyr | H |
| H | 4-F-Ph | 4-Cl—Ph | 4-Pyr | H |
| H | Ph | 4-OMe—Ph | 4-Pyr | H |
| H | Ph | 4-Cl—Ph | 4-Pyr | H |
| H | Ph | 2,5-di-(OMe)—Ph | 4-Pyr | H |
| H | Ph | 4-F-Ph | 4-Pyr | H |
| H | 4-F-Ph | 4-SMe—Ph | 4-Pyr | H |
| H | 4-F-Ph | 4-S(O)Me—Ph | 4-Pyr | H |
| H | 4-Cl—Ph | Ph | 4-Pyr | H |
| H | 4-SMe—Ph | Ph | 4-Pyr | H |
| H | 4-S(O)Me-Ph-4-Pyr | Ph | H | Ph |
| H | 4-$CF_3$—Ph | Ph | 4-Pyr | H |
| H | 4-Me—Ph | Ph | 4-Pyr | H |
| H | 4-OH—Ph | Ph | 4-Pyr | H |
| H | 3,4-di-Cl—Ph | Ph | 4-Pyr | H |
| H | 3,4-di-OH—Ph | Ph | 4-Pyr | H |
| H | 4-F-Ph | Ph | 4-Pyr | $CO_2Et$ |
| H | 3-Cl—Ph | Ph | 4-pyr | H |
| H | 4-CN—Ph | Ph | 4-Pyr | H |
| H | Ph | 4-$CO_2$Et-Ph | 4-Pyr | H |
| H | Ph | 2-F-Ph | 4-Pyr | H |
| H | Ph | 3-$NO_2$-Ph | 4-Pyr | H |
| H | 5-Me-thiophen-2-yl | Ph | 4-Pyr | H |
| H | 3-Me-thiophen-2-yl | Ph | 4-Pyr | H |
| H | 3-quinolinyl | Ph | 4-Pyr | H |
| H | 4-F-Ph | Ph | 4-Pyr | CN |
| H | 4-F-Ph | 4-(SMe)-Ph | 4-(3-Me)-Pyr | H |

TABLE IX-continued

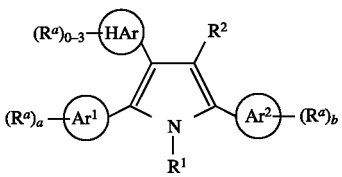

| R¹ | (Rᵃ)ₐ—Ar¹ | Ar²—(Rᵃ)ᵦ | (Rᵃ)₀₋₃—HAr | R² |
|---|---|---|---|---|
| H | 4-F-Ph | 4-(SMe)-Ph | 4-(3-Me)-Pyr | H |
| H | Ph | 2-(NO₂)-Ph | 4-Pyr | H |
| H | Ph | 3-F-Ph | 4-Pyr | H |
| H | Ph | 4-CO₂H—Ph | 4-Pyr | H |
| H | Ph | 3-NH₂—Ph | 4-Pyr | H |
| H | Ph | 4-NO₂—Ph | 4-Pyr | H |
| H | 4-F-Ph | Ph | 4-Pyr | H |
| H | 2,4-di-F-Ph | Ph | 4-Pyr | H |
| H | 3-CN—Ph | Ph | 4-Pyr | H |
| H | 3,4-di-F-Ph | Ph | 4-Pyr | H |
| H | Ph | 4-NH₂—Ph | 4-Pyr | H |
| H | 4-F-Ph | 4-S(O)Me—Ph | 4-quinolinyl | H |
| H | 4-F-Ph | 4-SMe—Ph | 4-pyr | Br |
| H | 4-F-Ph | 4-SMe—Ph | 4-quinolinyl | H |
| H | Ph | 4-(CONHCH₂-phenyl)-Ph | 4-pyr | H |
| H | Ph | 4-(NHCO(CH₂)₃-NMe₂-Ph | 4-pyr | H |
| H | Ph | 4-(CONHCH₂-4-pyr-Ph | 4-pyr | H |
| H | Ph | 4-(CONH(CH₂)₂-(1-piperidinyl))-Ph | 4-pyr | H |
| H | Ph | 4-(CONH(CH₂)₂-2-(N-methylimidazolyl)-Ph | 4-pyr | H |
| H | Ph | 4-(CONH(CH₂)₂-pyridyl))-Ph | 4-pyr | H |
| H | Ph | 4-(CONHCH₂-(3-pyridyl))-Ph | 4-pyr | H |
| H | Ph | 3-(NHCO(CH₂)3NMe₂)-Ph | 4-pyr | H |
| H | Ph | 4-(NHCO(CH₂)₂-(1-piperidyl))-Ph | 4-pyr | H |
| H | 2-Cl—Ph | Ph | 4-pyr | H |
| H | 3-Cl—Ph | 4-SMe—Ph | 4-pyr | H |
| H | 4-F-Ph | Ph | 4-pyrimidinyl | F |
| H | 4-F-Ph | 4-SMe—Ph | 4-(2-methyl)-pyr | H |
| H | 3-Cl—Ph | 4-S(O)Me—Ph | 4-pyr | H |
| H | 4-F-Ph | 4-S(O)Me—Ph | 4-(2-methyl)-pyr | H |
| H | 3,4-di-F-Ph | 4-SMe—Ph | 4-pyr | H |
| H | 3,4-di-F-Ph | 4-S(O)Me—Ph | 4-Pyr | H |
| H | 4-F-Ph | 4-SO₂Me—Ph | 4-pyr | H |
| H | 3,4-di-F-Ph | Ph | 4-pyr | CO₂Et |
| H | 3,4-di-F-Ph | Ph | 4-pyr | CN |
| H | 3-CF₃—Ph | Ph | 4-pyr | CO₂Et |
| H | 3-CF₃—Ph | Ph | 4-pyr | CN |
| H | 3-Cl—Ph | 4-SO₂Me—Ph | 4-pyr | H |

What is claimed is:

1. A compound represented by formula I:

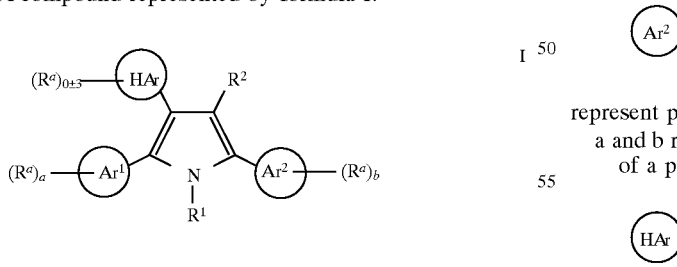

or a pharmaceutically acceptable salt thereof, wherein:

Ar¹ and

Ar² represent phenyl;

a and b represents integers, 0, 1, 2 or 3, such that the sum of a plus b is 1, 2, 3 or 4;

HAr represents pyridyl, unsubstituted or substituted with 0–3 $R^a$ groups;

each $R^a$ independently represents a member selected from the group consisting of: halo; CN, $NO_2$, $R^{21}$; $OR^{23}$; $SR^{23}$; $S(O)R^{21}$; $SO_2R^{21}$; $NR^{20}R^{23}$; $NR^{20}COR^{21}$; $NR^{20}CO_2R^{21}$; $NR^{20}CONR^{20}R^{23}$; $NR^{20}SO_2R^{21}$; $NR^{20}C(NR^{20})NHR^{20}$, $CO_2R^{23}$; $CONR^{20}R^{23}$;

$SO_2NR^{20}R^{23}$; $SO_2NR^{20}COR^{21}$; $SO_2NR^{20}CONR^{20}R^{23}$; $SO_2NR^{20}CO_2R^{21}$; $OCONR^{20}R^{23}$; $OCONR^{20}SO_2R^{20}$; $C(O)OCH_2OC(O)R^{20}$; $C(NR^{20})NR^{20}R^{23}$ and $CONR^{20}SO_2R^{21}$;

$R^1$ is selected from the group consisting of: H, aryl, $C_{1-15}$ alkyl, $C_{3-15}$ alkenyl and $C_{3-15}$ alkynyl, said alkyl, aryl, alkenyl and alkynyl being optionally substituted with from one to three members selected from the group consisting of: aryl, $OR^{20}$, $SR^{20}$, $N(R^{20})_2$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$; $OCONR^{20}R^{23}$ and $C(O)OCH_2OC(O)R^{20}$;

$R^2$ is selected from the group consisting of: H, $C_{1-15}$ alkyl, $C_{2-15}$ alkenyl, $C_{2-15}$ alkynyl, halo, $NO_2$, CN, $S(O)R^{21}$, $SO_2R^{21}$, $SO_2N(R^{20})_2$, $SO_2NR^{20}COR^{21}$, $SO_2NR^{20}CON(R^{20})_2$, $COR^{20}$, $CO_2R^{20}$, $CONR^{20}R^{23}$, $CONR^{20}SO_2R^{21}$ and $SO_2NR^{20}CO_2R^{21}$, said alkyl, alkenyl and alkynyl being optionally substituted with from one to three members selected from the group consisting of: halo, CN, aryl, $R^{20}$, $OR^{20}$, $SR^{20}$, $NR^{20}R^{23}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $NR^{20}C(NR^{20})NHR^{20}$, $CO_2R^{20}$, $CONR^{20}R^{23}$, $CONR^{20}SO_2R^{22}$, $NR^{20}SO_2R^{21}$, $SO_2NR^{20}CO_2R^{22}$, $OCONR^{20}SO_2R^{21}$ and $OCONR^{20}R^{23}$;

$R^{20}$ represents a member selected from the group consisting of: H, $C_{1-15}$ alkyl, $C_{2-15}$ alkenyl, $C_{2-15}$ alkynyl and aryl, said alkyl, alkenyl, alkynyl and aryl being optionally substituted with 1–3 groups selected from halo and aryl;

$R^{21}$ represents a member selected from the group consisting of: $C_{1-15}$ alkyl, $C_{2-15}$ alkenyl, $C_{2-15}$ alkynyl, and aryl, such alkyl, alkenyl and alkynyl being optionally interrupted with oxo and/or 1–2 heteroatoms selected from O, S, S(O), $SO_2$ and $NR^{20}$, said alkyl, alkenyl, alkynyl and aryl being optionally substituted with from 1–3 of halo, aryl, CN, $OR^{20}$, $O((CH_2)_nO)_mR^{20}$, $NR^{20}((CH_2)_nO)_mR^{20}$ wherein n represents an integer of from 2 to 4, and m represents an integer of from 1 to 3; $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}OC(O)R^{20}$, $C(O)OCH_2OC(O)R^{20}$ and $OCON(R^{20})_2$;

$R^{22}$ is selected from the group consisting of: $C_{1-15}$ alkyl, $C_{2-15}$ alkenyl, $C_{2-15}$ alkynyl and aryl, said alkyl, alkenyl, and alkynyl being optionally substituted with 1–3 halo or aryl groups;

$R^{23}$ is $R^{21}$ or H, and $R^{24}$ is selected from $COR^{22}$, $CO_2R^{22}$, $CON(R^{20})_2$, $SO_2R^{22}$ and $R^{23}$.

2. A compound in accordance with claim 1 wherein $R^1$ is hydrogen.

3. A compound in accordance with claim 1 wherein $R^1$ is substituted or unsubstituted $C_{1-15}$ alkyl.

4. A compound in accordance with claim 1 wherein $R^2$ represents a member selected from the group consisting of:
a) H;
b) $C_{1-6}$ alkyl;
c) halo;
d) CN;
e) $C(O)C_{1-6}$ alkyl;
f) $C(O)C_{1-6}$ alkylphenyl;
g) $CO_2H$;
h) $CO_2C_{1-6}$ alkyl;
i) $CO_2C_{1-6}$ alkylphenyl;
j) $CONH_2$;
k) $CONHC_{1-6}$ alkyl;
l) $C(O)N(C_{1-hd\ 6}$ alkyl$)_2$;
m) $SO_2NH_2$;
n) $SO_2NHC_{1-6}$ alkyl and
o) $SO_2N(C_{1-6}$ alkyl$)_2$.

5. A compound in accordance with claim 1 wherein:
$(R^a)_a$—$Ar^1$ is selected from the group consisting of:
a) phenyl,
b) 4-fluorophenyl,
c) 4-chlorophenyl,
d) 3-fluorophenyl,
e) 3-chlorophenyl,
f) 3-methylphenyl,
g) 3,4-dichlorophenyl,
h) 3-hydroxyphenyl,
i) 4-hydroxyphenyl,
j) 3,4-dihydroxyphenyl,
k) 4-carboxymethylphenyl,
l) 3-cyanophenyl,
m) 4-cyanophenyl,
n) 4-methylsulfinylphenyl,
o) 4-trifluoromethylphenyl,
p) 3-trifluoromethylphenyl,
q) 4-methylphenyl,
r) 4-t-butoxyphenyl,
s) 3,4-dibenzyloxyphenyl,
t) 2,4-difluorophenyl,
u) 3,4-difluorophenyl,
v) 4-methylsulfinylphenyl,
w) 4-methylsulfonylphenyl,
x) 2-methoxyphenyl,
y) 3-methoxyphenyl,
z) 4-nitrophenyl,
aa) 4-aminomethylphenyl, and
bb) 2-chlorophenyl;
$(R^a)_b$—$Ar^2$ is selected from the group consisting of:
a) 4-(methylthio)-phenyl,
b) 4-(ethylthio)-phenyl,
c) 3-(methylthio)-phenyl,
d) 2-(methylthio)-phenyl,
e) 3-(ethylthio)-phenyl,
f) 4-methylsulfonylphenyl,
g) 4-ethylsulfonylphenyl,
h) 3-methylsulfonylphenyl,
i) 2-methylsulfonylphenyl,
j) 4-methylsulfinylphenyl,
k) 4-ethylsulfonylphenyl,
l) 3-methylsulfinylphenyl,
m) 4-(N-methyl-N-benzyl)aminomethylphenyl, n) 3-(N-methyl-N-benzyl)aminomethylphenyl,
o) 4-methoxyphenyl,
p) 4-hydroxyphenyl,
q) 3-methoxyphenyl,
r) 2-benzyloxyphenyl,
s) 4-acetylaminophenyl,
t) phenyl,
u) 4-aminomethylphenyl,
v) 4-cyanophenyl,
w) 4-fluorophenyl,
x) 4-chlorophenyl,
y) 4-bromophenyl,
z) 4-carboxyethylphenyl,
aa) 2-fluorophenyl,
bb) 3-nitrophenyl,
cc) 4-nitrophenyl,
dd) 3-fluorophenyl,
ee) 4-carboxyphenyl,
ff) 4-aminophenyl,
gg) 3-aminophenyl,
hh) 4-(O(CH$_2$)$_3$NMe$_2$)-phenyl,
ii) 2-methoxyphenyl,
jj) 3-chlorophenyl,
kk) 4-trifluoromethylphenyl,
with the proviso that when (R$^a$)$_a$—Ar$^1$ is a), (R$^a$)$_b$—Ar$^2$ is one of a)–s) and u)–kk);
(R$^a$)$_{0-3}$—HAr is selected from the group consisting of:
  a) 4-pyridyl,
  b) 4-(2-methylpyridyl),
  c) 4-(2-aminopyridyl),
  d) 4-(2-methoxypyridyl),
  e) 4-(3-methylpyridyl),
  f) 2-pyridyl,
  g) 3,5-dimethyl-4-pyridyl, and
  h) 4-(2-aminobenzyl)pyridyl;
R$^1$ is:
  H; and
R$^2$ is selected from the group consisting of:
  a) H,
  b) F,
  c) Cl,
  d) Br,
  e) CN,
  f) C(O)C$_{1-6}$ alkyl,
  g) C(O)C$_{1-6}$ alkylphenyl,
  h) CO$_2$H,
  i) CO$_2$C$_{1-6}$ alkyl,
  j) CO$_2$C$_{1-6}$ alkylphenyl,
  k) CONH$_2$,
  l) CONHC$_{1-6}$ alkyl,
  m) C(O)N(C$_{1-6}$ alkyl)$_2$,
  n) SO$_2$NH$_2$,
  o) SO$_2$NHC$_{1-6}$ alkyl,
  p) SO$_2$N(C$_{1-6}$ alkyl)$_2$,
  q) CHO and
  r) S(O)$_{1-2}$ C$_{1-6}$ alkyl.
6. A compound in accordance with claim 1 wherein:
R$^a$)$_a$—Ar$^1$ is selected from the group consisting of:
  a) phenyl,
  b) 4-fluorophenyl,
  c) 4-chlorophenyl,
  d) 3-fluorophenyl,
  e) 3-chlorophenyl,
  f) 3-methylphenyl,
  g) 3,4-dichlorophenyl,
  h) 3-hydroxyphenyl,
  i) 4-hydroxyphenyl,
  j) 3,4-dihydroxyphenyl,
  k) 4-carboxymethylphenyl,
  l) 3-cyanophenyl,
  m) 4-cyanophenyl,
  n) 4-methylsulfinylphenyl,
  o) 4-trifluoromethylphenyl,
  p) 3-trifluoromethylphenyl,
  q) 4-methylphenyl,
  r) 4-t-butoxyphenyl,
  s) 3,4-dibenzyloxyphenyl,
  t) 2,4-difluorophenyl,
  u) 3,4-difluorophenyl,
  v) 4-methylsulfinylphenyl,
  w) 4-methylsulfonylphenyl,
  x) 2-methoxyphenyl,
  y) 3-methoxyphenyl,
  z) 4-nitrophenyl,
  aa) 4-aminomethylphenyl,
  bb) 2-chlorophenyl,
  cc) 4-thiomethyl-phenyl,
  dd) 2-benzyloxy-phenyl,
  ee) 4-bromophenyl,
  ff) 4-methoxyphenyl and
  gg) 4-dimethylaminophenyl;
(R$^a$)$_b$—Ar$^2$ is selected from the group consisting of:
  a) 4-(methylthio)-phenyl,
  b) 4-(ethylthio)-phenyl,
  c) 3-(methylthio)-phenyl,
  d) 2-(methylthio)-phenyl,
  e) 3-(ethylthio)-phenyl,
  f) 4-methylsulfonylphenyl,
  g) 4-ethylsulfonylphenyl,
  h) 3-methylsulfonylphenyl,
  i) 2-methylsulfonylphenyl,
  j) 4-methylsulfinylphenyl,
  k) 4-ethylsulfonylphenyl,
  l) 3-methylsulfinylphenyl,
  m) 4-(N-methyl-N-benzyl)aminomethylphenyl,
  n) 3-(N-methyl-N-benzyl)aminomethylphenyl,
  o) 4-methoxyphenyl,
  p) 4-hydroxyphenyl,
  q) 3-methoxyphenyl,
  r) 2-benzyloxyphenyl,
  s) 4-acetylaminophenyl,
  t) phenyl,
  u) 4-aminomethylphenyl,
  v) 4-cyanophenyl, w) 4-fluorophenyl,
x) 4-chlorophenyl,
y) 4-bromophenyl,
z) 4-carboxyethylphenyl,
aa) 2-fluorophenyl,
bb) 3-nitrophenyl,
cc) 4-nitrophenyl,
dd) 3-fluorophenyl,
ee) 4-carboxyphenyl,
ff) 4-aminophenyl,
gg) 3-aminophenyl,
hh) 4-(O(CH$_2$)$_3$NMe$_2$)-phenyl,
ii) 2-methoxyphenyl,
jj) 3-chlorophenyl,
kk) 4-trifluoromethylphenyl,
ll) 2,5-dimethoxy-phenyl,
mm) 2-nitrophenyl,
nn) 4-dimethylaminophenyl,
oo) 2-chlorophenyl,
pp) 4-fluoro-3-chloro-phenyl,
qq) 4-(CONHCH$_2$-phenyl)-phenyl,
rr) 4-(NHCO(CH$_2$)$_3$NMe$_2$)-phenyl and
ss) 3-(NHCO(CH$_2$)$_3$-NMe$_2$)-phenyl
with the proviso that when $(R^a)_a$—Ar$^1$ is a), $(R^a)_b$—Ar$^2$ is one of a)–s) and u)–ss);
$(R^a)_{0-3}$—HAr is selected from the group consisting of:
a) 4-pyridyl,
b) 4-(2-methylpyridyl),
c) 4-(2-aminopyridyl),
d) 4-(2-methoxypyridyl),
e) 4-(3-methylpyridyl),
f) 2-pyridyl,
g) 3,5-dimethyl-4-pyridyl and
h) 4-(2-aminobenzyl)pyridyl;
R$^1$ is substituted or unsubstituted C$_{1-15}$ alkyl; and
R$^2$ is selected from the group consisting of:
a) H;
b) F;
c) Cl;
d) Br;
e) CN;
f) C(O)C$_{1-6}$ alkyl;
g) C(O)C$_{1-6}$ alkylphenyl;
h) CO$_2$H;
i) CO$_2$C$_{1-6}$ alkyl;
j) CO$_2$C$_{1-6}$ alkylphenyl;
k) CONH$_2$;
l) CONHC$_{1-6}$ alkyl;
m) C(O)N(C$_{1-6}$ alkyl)$_2$;
n) SO$_2$NH$_2$;
o) SO$_2$NHC$_{1-6}$ alkyl;
p) SO$_2$N(C$_{1-6}$ alkyl)$_2$;
r) CHO and
s) S(O)$_{1-2}$C$_1$–C$_6$alkyl.

7. A method of treating inflammation mediated by excess production of prostaglandins in a human in need of such treatment, which comprises administering to said human an effective cytokine interfering amount of a compound of claim 1.

8. A pharmaceutical composition comprising a compound according to claim 1 in combination with a pharmaceutically acceptable carrier.

9. A pharmaceutical composition made by combining a compound according to claim 1 and a pharmaceutically acceptable carrier.

10. A method of treating a cytokine mediated disease in a mammal in need of such treatment, which comprises administering to said mammal an effective cytokine interfering amount of a compound of claim 1.

11. The method according to claim 10 wherein the cytokine inhibited is IL-1.

12. The method according to claim 10 wherein the cytokine inhibited is IL-6.

13. The method according to claim 10 wherein the cytokine inhibited is TNF.

14. The method according to claim 10 wherein the cytokine inhibited is IL-8.

15. The method according to claim 10 wherein the cytokine mediated disease is septic shock, endotoxic shock, gram negative sepsis or toxic shock syndrome.

16. The method according to claim 10 wherein the cytokine mediated disease is bone resorption disease, graft versus host reaction, atherosclerosis, arthritis, osteoarthritis, rheumatoid arthritis, gout, psoriasis or a topical inflammatory disease state.

17. The method according to claim 10 wherein the cytokine mediated disease is adult respiratory distress syndrome, asthma or chronic pulmonary inflammatory disease.

18. The method according to claim 10 wherein the cytokine mediated disease is cardiac or renal reperfusion injury, thrombosis or glomerulonephritis.

19. The method according to claim 10 wherein the cytokine mediated disease is Crohn's disease, ulcerative colitis or inflammatory bowel disease.

20. The method according to claim 10 wherein the cytokine mediated disease is cachexia.

21. The method according to claim 10 wherein the cytokine mediated disease is a viral infection.

22. A compound represented by formula I:

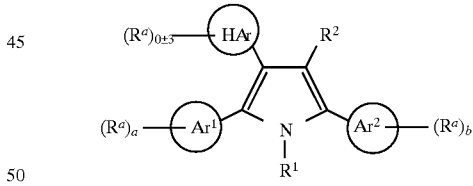

wherein:

and

each represent phenyl;

a and b represents integers, 0, 1, 2 or 3, such that the sum of a plus b is 1, 2, 3 or 4;

represents pyridyl, unsubstituted or substituted with 1—3 $R^a$ groups;

each $R^a$ independently represents a member selected from the group consisting of: halo; CN, $NO_2$, $R^{21}$; $OR^{23}$; $SR^{23}$; $S(O)R^{21}$; $SO_2R^{21}$; $NR^{20}R^{23}$; $NR^{20}COR^{21}$; $NR^{20}CO_2R^{21}$; $NR^{20}CONR^{20}R^{23}$; $NR^{20}SO_2R^{21}$; $NR^{20}C(NR^{20})NHR^{20}$, $CO_2R^{23}$; $CONR^{20}R^{23}$; $SO_2NR^{20}R^{23}$; $SO_2NR^{20}COR^{21}$; $SO_2NR^{20}CONR^{20}R^{23}$; $SO_2NR^{20}CO_2R^{21}$; $OCONR^{20}R^{23}$; $OCONR^{20}SO_2R^{20}$; $C(O)OCH_2OC(O)R^{20}$ and $C(NR^{20})NR^{20}R^{23}$;

$R^1$ is selected from the group consisting of: H, aryl, $C_{1-15}$ alkyl, $C_{2-15}$ alkenyl and $C_{2-15}$ alkynyl, said alkyl, aryl, alkenyl and alkynyl being optionally substituted with from one to three members selected from the group consisting of: aryl, $OR^{20}$, $SR^{20}$, $N(R^{20})_2$, $S(O)R^{21}$, $SO_2R^{21}$, $SO_2N(R^{20})_2$, $SO_2NR^{20}COR^{21}$, $SO_2NR^{20}CON(R^{20})_2$, $NR^{20}COR^{21}$, $NR^{20}CO_2R^{21}$, $NR^{20}CON(R^{20})_2$, $N(R^{20})C(NR^{20})NHR^{20}$, $CO_2R^{20}$, $CON(R^{20})_2$, $CONR^{20}SO_2R^{21}$, $NR^{20}SO_2R^{21}$, $SO_2NR^{20}CO_2R^{21}$, $OCON(R^{20})_2$, $OCONR^{20}SO_2R^{21}$ and $OCONR^{20}R^{23}$;

$R^2$ is selected from the group consisting of: H, $C_{1-15}$ alkyl, $C_{2-15}$ alkenyl, $C_{2-15}$ alkynyl, halo and $NO_2$, said alkyl, alkenyl and alkynyl being optionally substituted with from one to three members selected from the group consisting of: halo, CN, aryl, $R^{20}$, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$ and $OCONR^{20}R^{23}$;

$R^{20}$ represents a member selected from the group consisting of: H, $C_{1-15}$ alkyl, $C_{2-15}$ alkenyl, $C_{2-15}$ alkynyl and aryl, said alkyl, alkenyl and alkynyl being optionally substituted with 1–3 groups selected from halo and aryl;

$R^{21}$ represents a member selected from the group consisting of: $C_{1-15}$ alkyl, $C_{2-15}$ alkenyl, $C_{2-15}$ alkynyl and aryl, said alkyl, alkenyl, alkynyl and aryl being optionally substituted with from 1–3 of halo, aryl, CN, $OR^{20}$, $O((CH_2)_nO)_mR^{20}$, $NR^{20}((CH_2)_nO)_mR^{20}$ wherein n represents an integer of from 2 to 4, and m represents an integer of from 1 to 3, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}OC(O)R^{20}$, $C(O)OCH_2OC(O)R^{20}$ and $OCON(R^{20})_2$;

$R^{22}$ is selected from the group consisting of: $C_{1-15}$ alkyl, $C_{2-15}$ alkenyl, $C_{2-15}$ alkynyl and aryl, said alkyl, alkenyl, and alkynyl being optionally substituted with 1–3 halo or aryl groups;

$R^{23}$ is $R^{21}$ or H, and $R^{24}$ is selected from $COR^{22}$, $CO_2R^{22}$, $CON(R^{20})_2$, $SO_2R^{22}$ and $R^{23}$.

23. A compound according to claim 22 wherein $(R^a)_a$—$Ar^1$ is selected from the group consisting of:

a) phenyl,
b) 4-fluorophenyl,
c) 4-chlorophenyl,
d) 3-fluorophenyl,
e) 3-chlorophenyl,
f) 3-methyl phenyl,
g) 3,4 dichlorophenyl and
h) 3-hydroxyphenyl;

$Ar^2$—$(R^a)_b$ is selected from the group consisting of:

a) 4-(methylthio)-phenyl,
b) 4-(ethylthio)-phenyl,
c) 3-(methylthio)-phenyl,
d) 2-(methylthio)-phenyl,
e) 3-(ethylthio)-phenyl,
f) 4-methylsulfonylphenyl,
g) 4-ethylsulfonylphenyl,
h) 3-methylsulfonylphenyl,
i) 2-methylsulfonylphenyl,
j) 4-methylsulfinylphenyl,
k) 4-ethylsulfonylphenyl,
l) 3-methylsulfinylphenyl,
m) 4-(N-methyl-N-benzyl)aminomethylphenyl,
n) 3-(N-methyl-N-benzyl)aminomethylphenyl,
o) 4-methoxyphenyl,
p) 4-hydroxyphenyl,
q) 3-methoxyphenyl,
r) 2-benzyloxyphenyl and
s) 4-acetylaminophenyl;

HAr is selected from the group consisting of:

a) 4-pyridyl,
b) 4-(2-methylpyridyl),
c) 4-(2-aminopyridyl),
d) 4-(2-methoxypyridyl) and
i) 4-(3-methylpyridyl);

$R^1$ is:

H and $R^2$ is selected from the group consisting of:

a) H,
b) F,
c) Cl and
d) Br.

24. A compound in accordance with claim 1 selected from one of the following tables:

TABLE IV

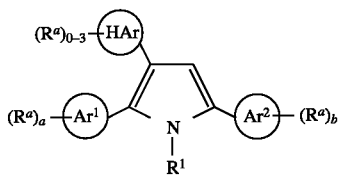

| Ex # | $(R^a)_a$—Ar¹ | Ar²—$(R^a)_b$ | $(R^a)_{0-3}$—HAr |
|---|---|---|---|
| 2 | Ph-4-F | Ph-4-OMe | 4-Pyridyl |
| 3 | Ph-4-F | Ph-2,5-di-OMe | 4-Pyridyl |
| 4 | Ph-4-F | Ph-4-Br | 4-Pyridyl |
| 5 | Ph-4-F | Ph-4-Cl | 4-Pyridyl |
| 6 | Ph-4-F | Ph-4-OMe | 2-Pyridyl |

TABLE IV-continued

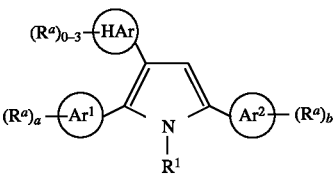

| Ex # | (Rᵃ)ₐ—Ar¹ | Ar²—(Rᵃ)ᵦ | (Rᵃ)₀₋₃—HAr |
|---|---|---|---|
| 7 | Ph-4-F | Ph-4-Br | 2-Pyridyl |
| 8 | Ph-4-F | Ph-4-Cl | 2-Pyridyl |
| 9 | Ph-4-F | Ph-2,5-di-OMe | 2-Pyridyl |
| 10 | Ph | Ph-4-OMe | 4-Pyridyl |
| 11 | Ph | Ph-4-Cl | 4-Pyridyl |
| 12 | Ph | Ph-2,5-di-OMe | 4-Pyridyl |
| 13 | Ph | Ph-4-F | 4-Pyridyl |
| 14 | Ph-4-Cl | Ph | 4-Pyridyl |
| 15 | Ph-4-F | Ph-4-SMe | 4-Pyridyl |
| 16 | Ph-4-SMe | Ph | 4-Pyridyl |
| 17 | 4-CF₃—Ph | Ph | 4-Pyridyl |
| 18 | 4-Me—Ph | Ph | 4-Pyridyl |
| 19 | 4-tBuO—Ph | Ph | 4-Pyridyl |
| 20 | 3,4-Cl—Ph | Ph | 4-Pyridyl |
| 21 | 3,4-di-(OBn)-Ph | Ph | 4-Pyridyl |
| 22 | 3-Cl—Ph | Ph | 4-pyridyl |
| 23 | 4-CN—Ph | Ph | 4-Pyridyl |
| 24 | 4-(COOMe)—Ph | Ph | 4-Pyridyl |
| 25 | Ph | 4-CO₂Et—Ph | 4-Pyridyl |
| 26 | Ph | 2-F-Ph | 4-Pyridyl |
| 27 | Ph | 3-NO₂—Ph | 4-Pyridyl |
| 30 | 4-F-Ph | 4-SMe—Ph | 4-(3-Me)-Pyridyl |
| 31 | Ph | 2-NO₂—Ph | 4-Pyridyl |
| 32 | Ph | 3-F-Ph | 4-Pyridyl |
| 33 | Ph | 4-NO₂—Ph | 4-Pyridyl |
| 34 | 4-F-Ph | Ph | 4-Pyridyl |
| 35 | 2,4-di-F-Ph | Ph | 4-Pyridyl |
| 36 | 3-CN-Ph | Ph | 4-Pyridyl |
| 37 | 3,4-F-Ph | Ph | 4-Pyridyl |
| 39 | 2-Cl—Ph | Ph | 4-pyridyl |

TABLE IV-continued

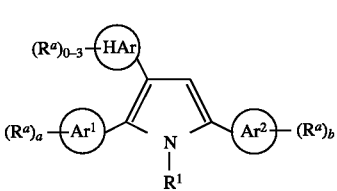

| Ex # | (Rᵃ)ₐ—Ar¹ | Ar²—(Rᵃ)ᵦ | (Rᵃ)₀₋₃—HAr |
|---|---|---|---|
| 40 | 3-Cl—Ph | 4-(SMe)—Ph | 4-pyridyl |
| 42 | 4-F-Ph | 4-(SMe)—Ph | 4-(2-methyl)-pyridyl |
| 43 | 3,4-di-F-Ph | 4-(SMe)—Ph | 4-pyridyl |

TABLE V

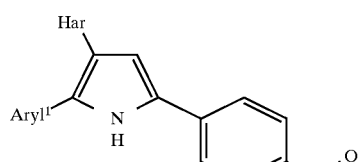

| Example # | Aryl¹ | Har |
|---|---|---|
| 45 | 4-F-phenyl | 4-(3-Me)-pyridyl |
| 47 | 3-Cl-phenyl | 4-pyridyl |
| 48 | 4-F-phenyl | 4-(2-Me)-pyridyl |
| 49 | 3,4-F-phenyl | 4-pyridyl |

TABLE VI

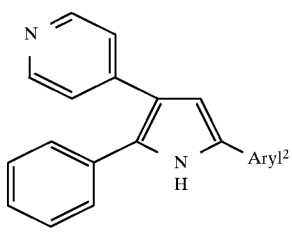

| Example # | Aryl² = |
|---|---|
| | 4-(CONHCH₂-phenyl)-phenyl |

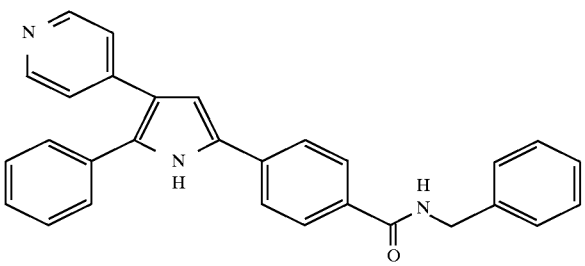

TABLE VI-continued

| Example # | Aryl² = |
|---|---|
| | 3-(NHCO(CH₂)₃-NMe₂)-phenyl |
| 62 | 4-(NHCO(CH₂)₃-N(CH₃)₂)-phenyl |

TABLE VII

| Ex # | (Rᵃ)ₐ-Ar¹ | Ar²-(Rᵃ)ᵦ | (Rᵃ)₀₋₃-HAr | R² |
|---|---|---|---|---|
| 71 | Ph | Ph-4-CN | 4-pyridyl | H |
| 72 | Ph | Ph-2-OMe | 4-pyridyl | H |
| 73 | Ph | Ph-3-OMe | 4-pyridyl | H |
| 74 | Ph-3,4-di-F | Ph-4-S(O)-Me | 4-pyridyl | H |
| 75 | Ph | Ph-4-NMe₂ | 4-pyridyl | H |
| 78 | Ph | Ph-2-Cl | 4-pyridyl | H |
| 79 | Ph | Ph-3-Cl | 4-pyridyl | H |
| 80 | Ph | Ph-4-CF₃ | 4-pyridyl | H |
| 81 | Ph | Ph-4-S-Me | 4-pyridyl | H |
| 82 | Ph | Ph-4-S(O)-Me | 4-pyridyl | H |
| 85 | Ph-4-F | Ph-4-F-3-Cl | 4-pyridyl | H |
| 88 | Ph-4-F | 4-(O(CH₂)₃NMe₂)-Ph | 4-pyridyl | H |
| 90 | Ph-4-Cl | Ph-4-F | 4-pyridyl | H |
| 91 | Ph-3-Cl | Ph-4-F | 4-pyridyl | H |
| 92 | Ph-2-Cl | Ph-4-F | 4-pyridyl | H |
| 93 | Ph-3,4-di-Cl | Ph-4-F | 4-pyridyl | H |
| 94 | Ph-3-CF₃ | Ph-4-F | 4-pyridyl | H |
| 95 | Ph-4-S-Me | Ph-4-F | 4-pyridyl | H |
| 96 | Ph-4-S(O)-Me | Ph-4-F | 4-pyridyl | H |
| 97 | Ph-2-OBn | Ph-4-F | 4-pyridyl | H |
| 98 | Ph-4-Br | Ph-4-F | 4-pyridyl | H |
| 99 | Ph-2-OMe | Ph-4-F | 4-pyridyl | H |
| 100 | Ph-3-OMe | Ph-4-F | 4-pyridyl | H |
| 101 | Ph-4-OMe | Ph-4-F | 4-pyridyl | H |
| 102 | Ph-4-NO₂ | Ph-4-F | 4-pyridyl | H |
| 103 | Ph-4-NMe₂ | Ph-4-F | 4-pyridyl | H |
| 110 | Ph-3-Cl | Ph-4-S(O)Me | 4-(2-Me)-pyridyl | H |
| 111 | Ph-3,4-di-F | Ph-4-S(O)Me | 4-(2-Me)-pyridyl | H |
| 112 | Ph-3,4-di-F | Ph-4-S(O)Me | 4-pyridyl | F |
| 113 | Ph-3-CF₃ | Ph | 4-pyridyl | H |
| 114 | Ph-4-F | Ph-4-S(O)Me | 4-(2-aminobenzyl)pyridyl | H |
| 116 | Ph-4-F | 4-(SMe)-Ph | 4-pyridyl | Br |

TABLE VII-continued
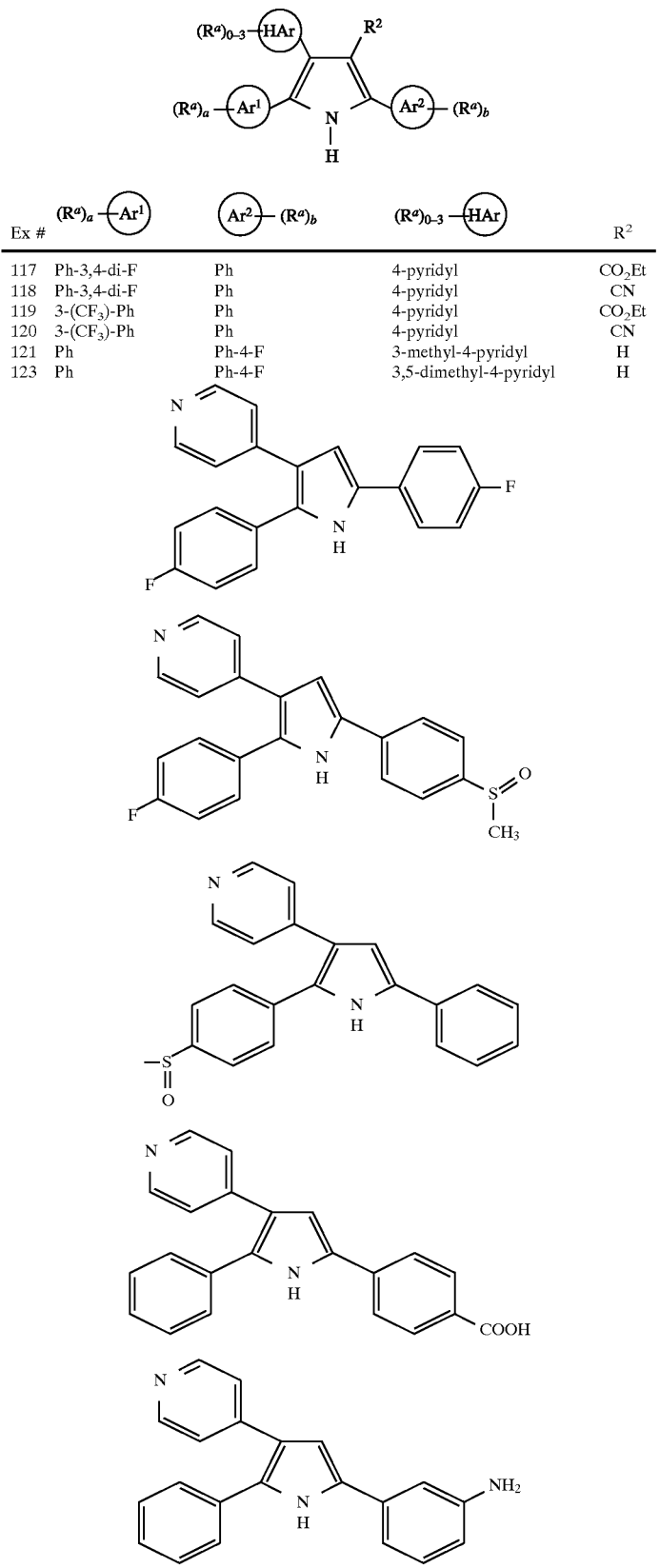
| Ex # | (Rᵃ)ₐ—Ar¹ | Ar²—(Rᵃ)ᵦ | (Rᵃ)₀₋₃—HAr | R² |
|---|---|---|---|---|
| 117 | Ph-3,4-di-F | Ph | 4-pyridyl | CO₂Et |
| 118 | Ph-3,4-di-F | Ph | 4-pyridyl | CN |
| 119 | 3-(CF₃)-Ph | Ph | 4-pyridyl | CO₂Et |
| 120 | 3-(CF₃)-Ph | Ph | 4-pyridyl | CN |
| 121 | Ph | Ph-4-F | 3-methyl-4-pyridyl | H |
| 123 | Ph | Ph-4-F | 3,5-dimethyl-4-pyridyl | H |

TABLE VII-continued

TABLE VII-continued
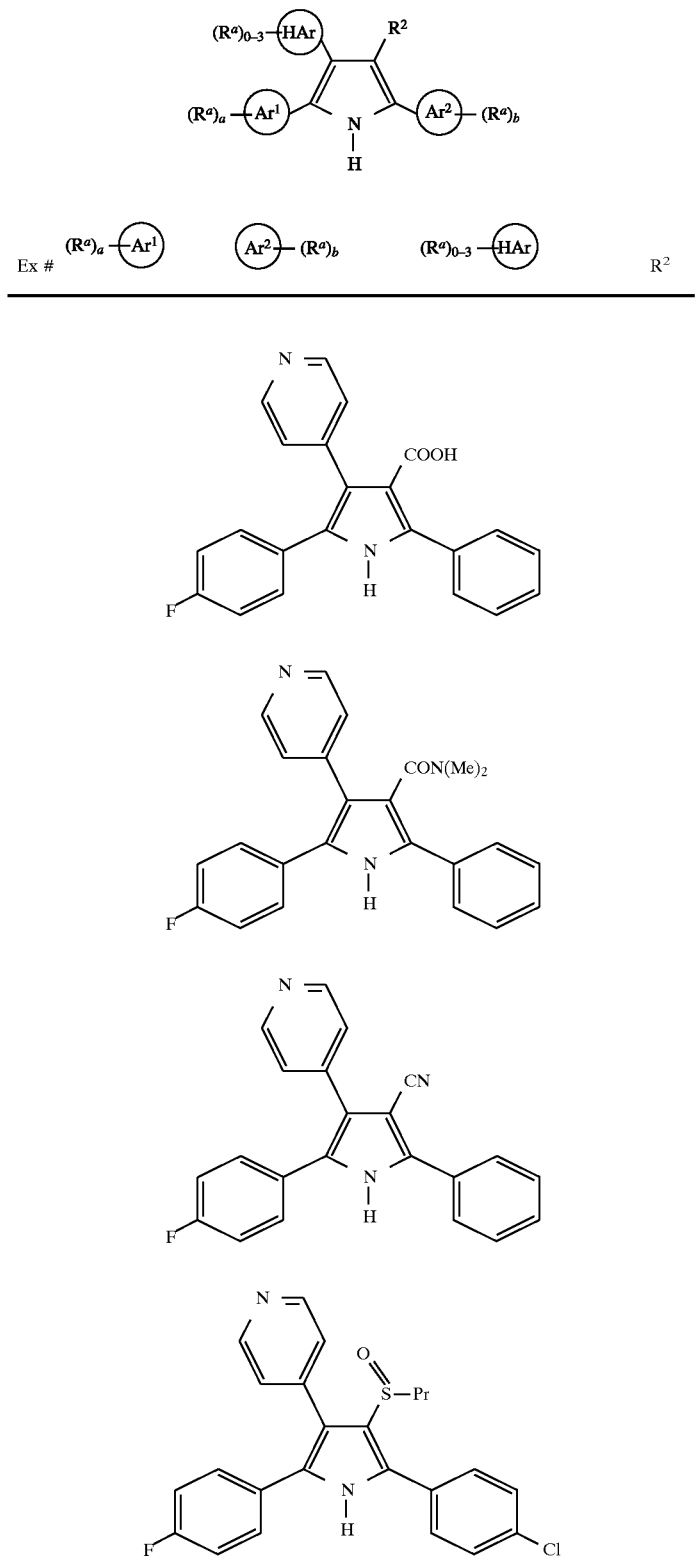

TABLE VII-continued
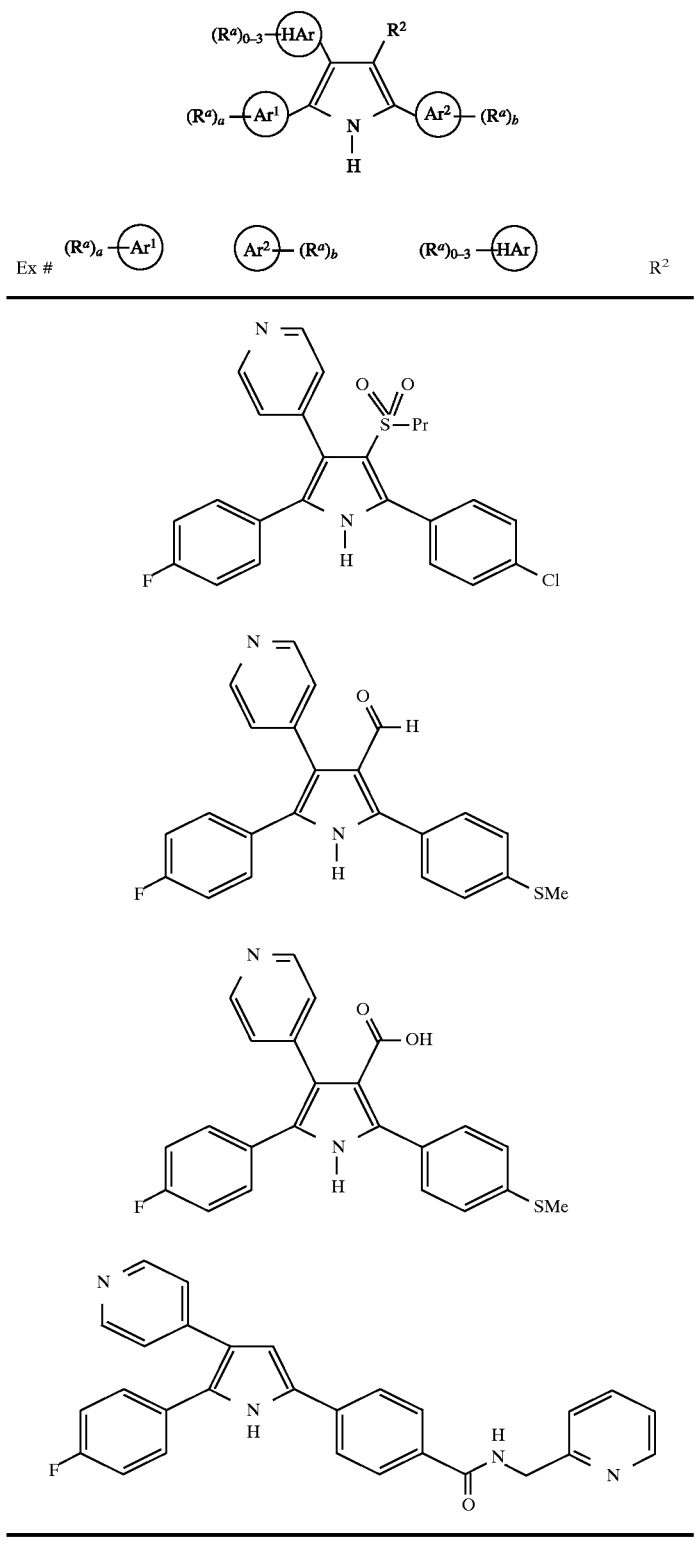

TABLE VIII

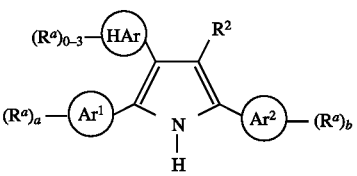

| Ex. | (Rᵃ)ₐ—Ar¹ | Ar²—(Rᵃ)ᵦ | (Rᵃ)₀₋₃—HAr | R² |
|---|---|---|---|---|
| 134 | Ph-4-F | Ph-4-OMe | 4-pyridyl | C(O)Me |
| 135 | Ph-4-F | Ph-2,5-di-OMe | 4-pyridyl | C(O)Me |
| 136 | Ph-4-F | Ph-4-Br | 4-pyridyl | C(O)Propyl |
| 137 | Ph-4-F | Ph-4-Cl | 4-pyridyl | C(O)Ethyl |
| 138 | Ph-4-F | Ph-4-OMe | 2-pyridyl | C(O)Me |
| 139 | Ph-4-F | Ph-4-Br | 2-pyridyl | C(O)Me |
| 140 | Ph-4-F | Ph-2,5-di-OMe | 2-pyridyl | C(O)Me |
| 141 | Ph | Ph-4-OMe | 4-pyridyl | C(O)Me |
| 142 | Ph | Ph-4-Cl | 4-pyridyl | C(O)Me |
| 143 | Ph | Ph-2,5-di-OMe | 4-pyridyl | C(O)Me |
| 144 | Ph | Ph-4-F | 4-pyridyl | C(O)Me |
| 145 | Ph-4-Cl | Ph | 4-pyridyl | C(O)Me |
| 146 | Ph-4-F | Ph-4-SMe | 4-pyridyl | C(O)Me |
| 147 | Ph-4-SMe | Ph | 3-methyl-4-pyridyl | C(O)Me |
| 148 | Ph-4-F | Ph-4-SMe | 3-methyl-4-pyridyl | CN |
| 149 | Ph-4-F | Ph-4-S(O)Me | 3-methyl-4-pyridyl | CN |
| 151 | Ph-4-F | Ph-4-Cl | 2-methyl-4-pyridyl | CN |
| 152 | Ph | Ph-4-F | 3,5-dimethyl-4-pyridyl | CN |
| 164 | Ph | Ph-4-F | 4-pyridyl | COMe |
| 165 | Ph | Ph-4-F | 4-pyridyl | SO₂Me |
| 166 | Ph | Ph-4-CN | 4-pyridyl | COMe |
| 167 | Ph | Ph-2-OMe | 4-pyridyl | COMe |
| 168 | Ph | Ph-3-OMe | 4-pyridyl | CN |
| 169 | Ph | Ph-4-OMe | 4-pyridyl | CO₂Et |
| 170 | Ph | Ph-4-NO₂ | 4-pyridyl | CN |
| 171 | Ph | Ph-4-NMe₂ | 4-pyridyl | CN |
| 174 | Ph | Ph-2-Cl | 4-pyridyl | CN |
| 175 | Ph | Ph-3-Cl | 4-pyridyl | C(O)Me |
| 176 | Ph | Ph-4-CF₃ | 4-pyridyl | SO₂Me |
| 177 | Ph | Ph-4-S-Me | 4-pyridyl | CN |
| 178 | Ph | Ph-4-S(O)-Me | 4-pyridyl | CN |
| 183 | Ph-4-F | Ph-4-F-3-Cl | 4-pyridyl | CN |
| 186 | Ph-4-F | 4-(O(CH₂)₃-NMe₂)-Ph | 4-pyridyl | CN |
| 188 | Ph-4-Cl | Ph-4-F | 4-pyridyl | CN |
| 189 | Ph-3-Cl | Ph-4-F | 4-pyridyl | CN |
| 190 | Ph-2-Cl | Ph-4-F | 4-pyridyl | CN |
| 191 | Ph-3,4-di-Cl | Ph-4-F | 4-pyridyl | CN |
| 192 | Ph-3-CF₃ | Ph-4-F | 4-pyridyl | CN |
| 193 | Ph-4-S-Me | Ph-4-F | 4-pyridyl | CN |
| 194 | Ph-4-S(O)-Me | Ph-4-F | 4-pyridyl | CN |
| 195 | Ph-2-OBn | Ph-4-F | 4-pyridyl | CN |
| 196 | Ph-4-Br | Ph-4-F | 4-pyridyl | CN |
| 197 | Ph-2-OMe | Ph-4-F | 4-pyridyl | CN |
| 198 | Ph-3-OMe | Ph-4-F | 4-pyridyl | CN |
| 199 | Ph-4-OMe | Ph-4-F | 4-pyridyl | CN |
| 200 | Ph-4-NO₂ | Ph-4-F | 4-pyridyl | CN |
| 201 | Ph-4-NMe₂ | Ph-4-F | 4-pyridyl | CN |

TABLE IX

| R¹ | (Rᵃ)ₐ—Ar¹ | Ar²—(Rᵃ)ᵦ | (Rᵃ)₀₋₃—HAr | R² |
|---|---|---|---|---|
| H | 4-F-Ph | 4-F-Ph | 4-Pyr | H |
| H | 4-F-Ph | 4-OMe—Ph | 4-Pyr | H |
| H | 4-F-Ph | 2,5-di-(OMe)—Ph | 4-Pyr | H |
| H | 4-F-Ph | 4-Br—Ph | 4-Pyr | H |
| H | 4-F-Ph | 4-Cl—Ph | 4-Pyr | H |
| H | Ph | 4-OMe—Ph | 4-Pyr | H |
| H | Ph | 4-Cl—Ph | 4-Pyr | H |
| H | Ph | 2,5-di-(OMe)—Ph | 4-Pyr | H |
| H | Ph | 4-F-Ph | 4-Pyr | H |
| H | 4-F-Ph | 4-SMe—Ph | 4-Pyr | H |
| H | 4-F-Ph | 4-S(O)Me—Ph | 4-Pyr | H |
| H | 4-Cl—Ph | Ph | 4-Pyr | H |
| H | 4-SMe—Ph | Ph | 4-Pyr | H |
| H | 4-CF₃Ph | Ph | 4-Pyr | H |
| H | 4-Me—Ph | Ph | 4-Pyr | H |
| H | 4-OH—Ph | Ph | 4-Pyr | H |
| H | 3,4-di-Cl—Ph | Ph | 4-Pyr | H |
| H | 3,4-di-OH—Ph | Ph | 4-Pyr | H |
| H | 4-F-Ph | Ph | 4-Pyr | CO₂Et |
| H | 3-Cl—Ph | Ph | 4-pyr | H |
| H | 4-CN—Ph | Ph | 4-Pyr | H |
| H | Ph | 4-CO₂Et—Ph | 4-Pyr | H |
| H | Ph | 2-F-Ph | 4-Pyr | H |
| H | Ph | 3-NO₂—Ph | 4-Pyr | H |
| H | 4-F-Ph | Ph | 4-Pyr | CN |
| H | 4-F-Ph | 4-(SMe)—Ph | 4-(3-Me)-Pyr | H |
| H | 4-F-Ph | 4-(SMe)—Ph | 4-(3-Me)-Pyr | H |
| H | Ph | 2-(NO₂)-Ph | 4-Pyr | H |
| H | Ph | 3-F-Ph | 4-Pyr | H |
| H | Ph | 4-CO₂H—Ph | 4-Pyr | H |
| H | Ph | 3-NH₂—Ph | 4-Pyr | H |
| H | Ph | 4-NO₂—Ph | 4-Pyr | H |
| H | 4-F-Ph | Ph | 4-Pyr | H |
| H | 2,4-di-F-Ph | Ph | 4-Pyr | H |
| H | 3-CN—Ph | Ph | 4-Pyr | H |
| H | 3,4-di-F-Ph | Ph | 4-Pyr | H |
| H | Ph | 4-NH₂—Ph | 4-Pyr | H |
| H | 4-F-Ph | 4-SMe—Ph | 4-pyr | Br |
| H | Ph | 4-(CONHCH₂-phenyl)-Ph | 4-pyr | H |
| H | Ph | 4-(NHCO(CH₂)₃-NMe₂-Ph | 4-pyr | H |
| H | Ph | 3-(NHCO(CH₂)3NMe₂)-Ph | 4-pyr | H |
| H | 2-Cl—Ph | Ph | 4-pyr | H |
| H | 3-Cl—Ph | 4-SMe—Ph | 4-pyr | H |
| H | 4-F-Ph | 4-SMe—Ph | 4-(2-methyl)-pyr | H |
| H | 3-Cl—Ph | 4-S(O)Me—Ph | 4-pyr | H |
| H | 4-F-Ph | 4-S(O)Me—Ph | 4-(2-methyl)-pyr | H |
| H | 3,4-di-F-Ph | 4-SMe—Ph | 4-pyr | H |
| H | 3,4-di-F-Ph | 4-S(O)Me—Ph | 4-Pyr | H |
| H | 4-F-Ph | 4-SO₂Me—Ph | 4-pyr | H |
| H | 3,4-di-F-Ph | Ph | 4-pyr | CO₂Et |
| H | 3,4-di-F-Ph | Ph | 4-pyr | CN |
| H | 3-CF₃—Ph | Ph | 4-pyr | CO₂Et |
| H | 3-CF₃—Ph | Ph | 4-pyr | CN |
| H | 3-Cl—Ph | 4-SO₂Me—Ph | 4-pyr | H |

25. A compound in accordance with claim 1 which is:
2-(4-fluorophenyl)-5-(4-methylsulfonylphenyl)-3-(4-pyridyl) pyrrole;
2-(3-chlorophenyl)-5-(4-methylsulfonylphenyl)-3-(4-pyridyl) pyrrole;
2,5-bis-(4-fluorophenyl)-3-(4-pyridyl)-pyrrole;
2-(4-fluorophenyl)-5-(4-methylsulfinylphenyl)-3-(4-pyridyl)-pyrrole;
2-(4-methylsulfinyl phenyl)-5-(phenyl)-3-(4-pyridyl)-pyrrole;
2-(4-phenyl)-5-(4-carboxyphenyl)-3-(4-pyridyl)-pyrrole;
2-(4-phenyl)-5-(4-aminophenyl)-3-(4-pyridyl)-pyrrole;
2-(4-phenyl)-5-(3-aminophenyl)-3-(4-pyridyl)-pyrrole;
2-(4-hydroxyphenyl)-5-(phenyl)-3-(4-pyridyl)-pyrrole or
2-(3,4-(OH)₂-phenyl)-5-(phenyl)-3-(4-pyridyl)-pyrrole.

* * * * *

UNITED STATES PATENT AND TRADEMARK OFFICE
CERTIFICATE OF CORRECTION

PATENT NO. : 5,837,719
DATED : November 17, 1998
INVENTOR(S) : Stephen E. de Laszlo, Nigel J. Liverton, Gerald S. Ponticello, Harold G. Selnick and Nathan B. Mantlo It is certified that error appears in the above-identified patent and that said Letters Patent is hereby corrected as shown below:

(1) In column 69 at line 50, please delete the structure and replace it with the following:

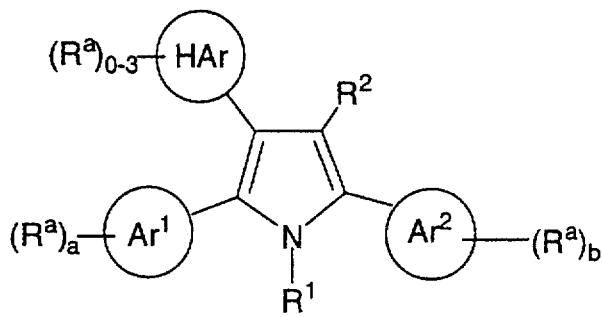

(2) In column 72, line 12, delete "l) $C(O)N(C_{1-hd\,6}$ alkyl$)_2$; " and insert:

-- l) $C(O)N(C_{1-6}$ alkyl$)_2$; --

UNITED STATES PATENT AND TRADEMARK OFFICE
CERTIFICATE OF CORRECTION

PATENT NO. : 5,837,719
DATED : November 17, 1998
INVENTOR(S) : Stephen E. de Laszlo, Nigel J. Liverton, Gerald S. Ponticello, Harold G. Selnick and Nathan B. Mantlo It is certified that error appears in the above-identified patent and that said Letters Patent is hereby corrected as shown below:

(3) In column 76, line 43, please delete the structure and replace it with the following:

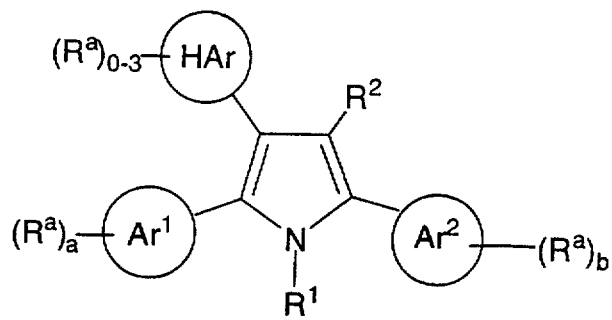

Signed and Sealed this

Twentieth Day of July, 1999

Q. TODD DICKINSON

*Attest:*

*Attesting Officer*    Acting Commissioner of Patents and Trademarks